(12) United States Patent
Aneja et al.

(10) Patent No.: US 11,607,421 B2
(45) Date of Patent: *Mar. 21, 2023

(54) ETHANOLAMINE-BASED LIPID BIOSYNTHETIC COMPOUNDS, METHOD OF MAKING AND USE THEREOF

(71) Applicant: Metanoi Therapeutics, Inc., Atlanta, GA (US)

(72) Inventors: Ritu Aneja, Lilburn, GA (US); Venkata Subba Rao Mukkavilli, Decatur, GA (US)

(73) Assignee: Metanoi Therapeutics, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,289

(22) Filed: Feb. 19, 2019

(65) Prior Publication Data

US 2019/0262366 A1 Aug. 29, 2019

Related U.S. Application Data

(63) Continuation of application No. 15/468,815, filed on Mar. 24, 2017, now Pat. No. 10,213,448.

(60) Provisional application No. 62/313,417, filed on Mar. 25, 2016.

(51) Int. Cl.
| | |
|---|---|
| *A61K 31/133* | (2006.01) |
| *A61K 9/48* | (2006.01) |
| *A61K 31/685* | (2006.01) |
| *A61K 9/00* | (2006.01) |

(52) U.S. Cl.
CPC .......... *A61K 31/685* (2013.01); *A61K 9/0014* (2013.01); *A61K 9/0019* (2013.01); *A61K 9/0043* (2013.01); *A61K 9/48* (2013.01); *A61K 31/133* (2013.01)

(58) Field of Classification Search
CPC ................................ A61K 31/133; A61K 9/48
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,927,623 A | 5/1990 | Long, Jr. | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,036 A | 12/1991 | Long, Jr. | |
| 5,077,211 A | 12/1991 | Yarosh | |
| 5,114,703 A | 5/1992 | Wolf et al. | |
| 5,171,755 A | 12/1992 | Kaufman et al. | |
| 5,264,618 A | 11/1993 | Felgner et al. | |
| 5,304,325 A | 4/1994 | Kaufman et al. | |
| 5,350,571 A | 9/1994 | Kaufman et al. | |
| 5,393,524 A | 2/1995 | Quay | |
| 5,403,575 A | 4/1995 | Kaufman et al. | |
| 5,690,907 A | 11/1997 | Lanza et al. | |
| 5,780,010 A | 7/1998 | Lanza et al. | |
| 5,958,371 A | 9/1999 | Lanza et al. | |
| 5,989,520 A | 11/1999 | Lanza et al. | |
| 2004/0185028 A1* | 9/2004 | Hu | A01N 33/12 424/78.27 |
| 2007/0154559 A1 | 7/2007 | Pai et al. | |
| 2008/0051463 A1 | 2/2008 | Gerlach et al. | |
| 2010/0104645 A1 | 4/2010 | Ali et al. | |
| 2014/0256804 A1* | 9/2014 | Iwata | A61K 9/1652 514/456 |
| 2015/0150822 A1 | 6/2015 | Perumal et al. | |
| 2015/0329832 A1 | 11/2015 | Senda et al. | |
| 2016/0074322 A1 | 3/2016 | Radhakrishnan et al. | |

OTHER PUBLICATIONS

Cosmetic Ingredient Review, Assessment of Ethanolamine and Ethanolamine Salts as used in Cosmetics, 2012, pp. 1-18.*
Hellwig et al. Fundam. Appl. Toxicol., 1997, vol. 40, No. 1, Abstract.*
Kulthanan et al. Asia Pac. Allergy, 2013, vol. 3, pp. 155-160.*
Kathpalia et al. J. Adv. Pharm. Edu & Research, 2014, vol. 4, No. 2, pp. 165-177.*
Hellwig et al. Fundam. Appl. Toxicol., 1997, vol. 40, No. 1, pp. 158-162.*
Gerbrach et al. Arch. Toxicology, 1998, vol. 72, pp. 319-329.*
Ferreira, A. K. et al., "Anticancer Effects of Synthetic Phosphoethanolamine on Ehrlich Ascites Tumor: An Experimental Study", Anticancer Research, 2012, vol. 32, pp. 95-104.
Ledford, H., "Brazilian courts tussle over unproven cancer treatment", Nature, 2015, vol. 527, pp. 420-421.
Le Mercier, I., et al., "Beyond CTLA-4 and PD-1, the Generation Z of Negative Checkpoint Regulators," Frontiers in Immunology, Aug. 2015, vol. 6, Article 418, pp. 1-15.
Kyi, C., et al., "Checkpoint Blocking Antibodies in Cancer Immunotherapy," FEBS Letters, Jan. 2014, vol. 588, Issue 2, pp. 368-376.
Marin-Hernandez, A., et al., "HIF-1alpha Modulates Energy Metabolism in Cancer Cells by Inducing Over-Expression of specific glycolytic isoforms. Mini Rev Med Chem", 2009. 9(9): pp. 1084-1101.

(Continued)

*Primary Examiner* — Samira J Jean-Louis
(74) *Attorney, Agent, or Firm* — Thomas | Horstemeyer, LLP

(57) ABSTRACT

A method for treating cancer is disclosed. The method comprises administering to a subject in need thereof, an effective amount of a pharmaceutical composition comprising monoethanolamine, its prodrug or hybrid molecule or a pharmaceutically acceptable salt thereof, and a pharmaceutically effective carrier. Also disclosed is a composition comprising monoethanolamine or a pharmaceutically acceptable salt thereof and a pharmaceutically effective carrier, wherein the pharmaceutical composition is formulated for oral, intravenous, intraperitoneal, subcutaneous, dermal, or intranasal administration.

3 Claims, 23 Drawing Sheets

(56) References Cited

OTHER PUBLICATIONS

Munoz-Pinedo, C., et al., "Cancer Metabolism: Current Perspectives and Future Directions," Cell Death and Disease, 2012. vol. 3, e248, pp. 1-10.
Gohil, V.M., et al., "Meclizine Inhibits Mitochondrial Respiration through Direct Targeting of Cytosolic Phosphoethanolamine Metabolism," The Journal of Biological Chemistry, 2013, vol. 288, No. 49, pp. 35387-35395.
Modica-Napolitano, J.S., et al., "Ethanolamine and Phosphoethanolamine Inhibit Mitochondrial Function in Vitro: Implications for Mitochondrial Dysfunction Hypothesis in Depression and Bipolar Disorder," Biological Psychiatry, 2004, vol. 55, Issue 3, pp. 273-277.
File History of U.S. Appl. No. 15/468,815, filed Mar. 24, 2017.
U.S. Appl. No. 15/468,518, filed Mar. 24, 2017, Pending.

\* cited by examiner

ETHANOLAMINE-BASED LIPID BIOSYNTHETIC COMPOUNDS, METHOD OF MAKING AND USE THEREOF

This application is a Divisional of U.S. application Ser. No. 15/468,815, filed Mar. 24, 2017, which claims priority to U.S. Provisional Patent Application Ser. No. 62/313,417, filed Mar. 25, 2016. The entirety of the aforementioned application is incorporated herein by reference.

FIELD

This application generally relates to phosphatidylethanolamine (PE) lipid biosynthetic compounds for treating cancer. More specifically, this application relates to a method for treating cancer with a pharmaceutical composition comprising monoethanolamine.

BACKGROUND

Toxicity and drug resistance are major impediments underlying the limited therapeutic success of currently available mono-targeted therapies. One approach to address these problems is to exploit the biochemical and metabolic pathways that are reprogrammed in cancer cells to develop superior, less-toxic, and well-tolerated cancer therapies. Altered lipid metabolism is emerging as one of the hallmarks of cancer. Thus cellular lipids and enzymes involved in lipid biosynthesis may serve as promising anticancer targets. A few studies have examined lipids and their precursor-based formulations as attractive anticancer drug candidates. For example, alkylphospholipids (ALPs) exert cytotoxic effects by targeting cell membranes instead of conventional targets, such as DNA or microtubules. These ALPs affect a variety of cellular processes such as lipid raft function, PI3K/Akt signaling, phosphatidylcholine (PC) synthesis and generation of reactive oxygen species (ROS). ALP-induced modulation of lipid rafts has been found to enhance recruitment and activation of the death receptor Fas/CD95 to induce apoptosis. Lipid precursors such as omega-3 polyunsaturated fatty acids (ω-3 PUFA) have been implicated in reducing cancer risk with lower cancer prevalence in population with higher dietary intake of ω-3 PUFA. Several long chain ω-3 PUFA exhibit antiproliferative activity against multiple cancer types including colon and prostate.

Another lipid precursor, phosphoethanolamine (PhosE), has recently been a subject of active laboratory research for its anticancer role. PhosE is a biosynthetic precursor of phosphatidylethanolamine (PE) lipids, which constitute the second most abundant lipid class in cells. PhosE is synthesized in the first step of Kennedy pathway of PE lipid biosynthesis through ATP-dependent phosphorylation of monoethanolamine (Etn). See FIG. 1. PhosE has been shown to exhibit antitumor activity in various in vitro and in vivo models of cancer by affecting cell-cycle progression, angiogenesis, macrophage activation and multiple signaling pathways that induce apoptosis. PhosE inhibits murine melanoma by downregulation of Bax/Bad protein. The present inventors have surprisingly found that the key precursor with anticancer activity in the PE lipid pathway is not PhosE, but rather Etn.

In view of the limited success in addressing toxicities and drug resistance in current anticancer strategies, there is a need for effective, less-toxic and better-tolerated cancer therapies.

SUMMARY

One aspect of the present application relates to compositions and methods for treating cancer with Etn. In one embodiment, a method for treating cancer comprises orally administering to a subject in need thereof, an effective amount of a pharmaceutical composition comprising Etn, or a pharmaceutically acceptable salt thereof, and a pharmaceutically effective carrier.

In certain embodiments, the subject has a cancer selected from the group consisting of prostate, breast, lung, kidney, liver, ovarian, pancreatic and gastrointestinal. In a preferred embodiment, the subject has prostate cancer.

In some embodiments, the composition is formulated in an oral dosage form. Oral dosage forms may include a solid formulation, a liquid formulation, or a combination thereof.

In some embodiments, the composition alternatively includes, or additionally includes one or more compounds in the PE lipid biosynthesis pathway.

In certain embodiments, the composition comprises PhosE in an amount that is 20% (w/w) or less of the amount of Etn.

In other embodiments, the composition does not contain PhosE.

Figure 12:
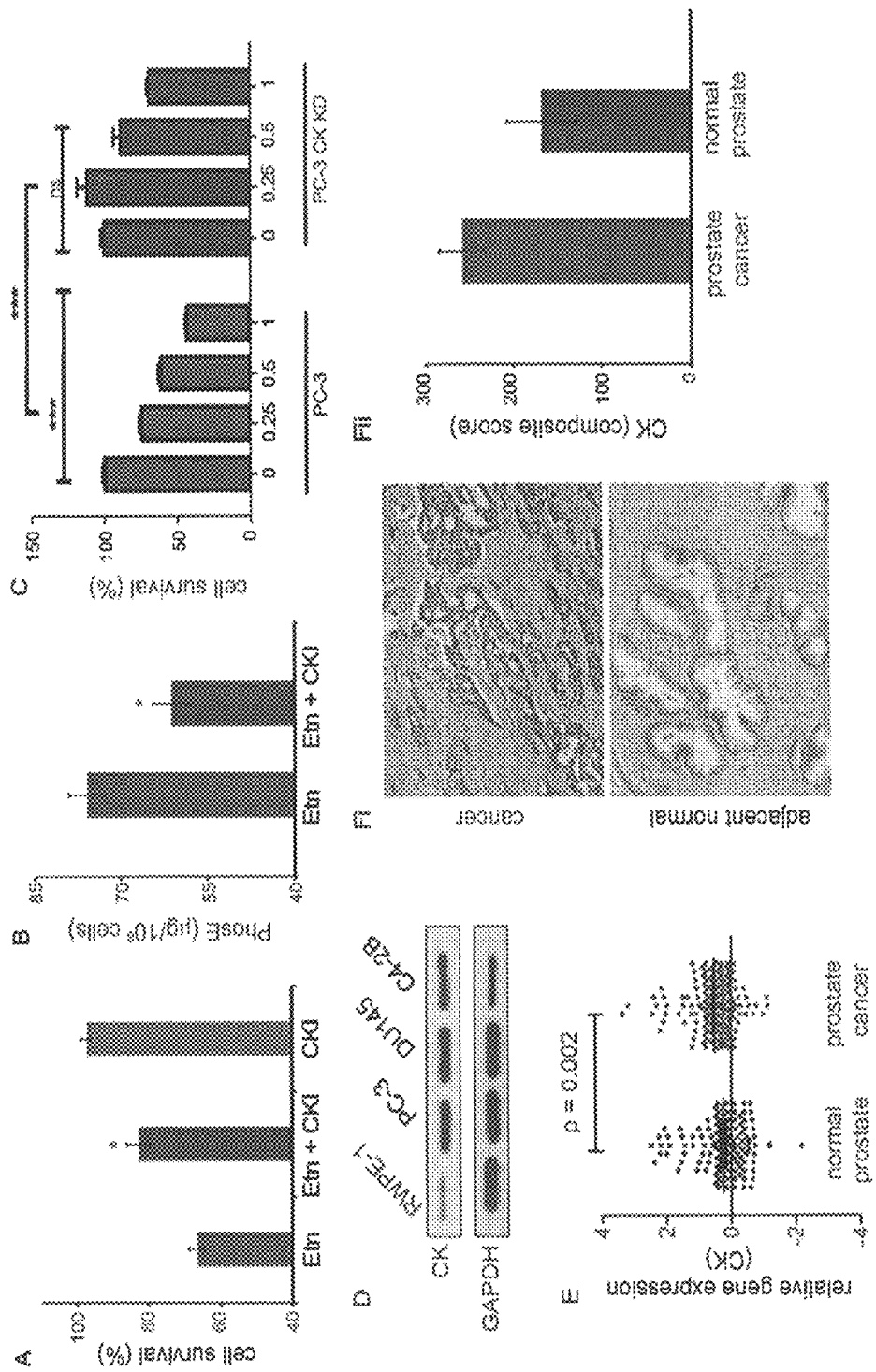

FIG. 12 shows the effect of choline kinase inhibition on Etn induced inhibition of cell growth and intracellular levels of PhosE in PC-3 cells. (Panel A) Proliferation of PC-3 cells upon Etn treatment in the presence and absence of choline kinase inhibitor (CKI). PC-3 cells were treated with 1 mg/ml Etn in the presence and absence of 1 µM CKI for 48 h at pH 7.4 and cell survival was estimated by MTT assay. Choline kinase inhibition significantly abrogated Etn-induced cell death in PC-3 cells. (Panel B) Intracellular levels of PhosE upon Etn treatment of PC-3 cells in the presence and absence of CKI. Choline kinase inhibition resulted in reduced conversion of Etn into PhosE in PC-3 cells. (Panel C) Effect of Etn on cellular viability of PC-3 cells with CK knock down (KD) using siRNA approach. CK KD PC-3 cells were treated with 0.25, 0.5 and 1 mg/ml Etn for 48 h at pH 7.4 followed by estimation of cell survival by MTT assay. (Panel D) Choline kinase expression in prostate cancer cell lines (PC-3, DU145 and C42B) and normal prostate cell line (RWPE-1). GAPDH was used as a loading control. (Panel E) Scatter-plot comparing choline kinase expression in normal and cancer tissue from prostate cancer patients (p=0.002). The p value for statistical significance was set up as 0.05, while the fold change was defined as mean of all individual data points of analyzed datasets. (Panel Fi) Micrographs showing immunohistochemical staining of choline kinase enzyme in normal and cancer tissue from prostate cancer patients. (Panel Fii) Quantification (composite score) of choline kinase expression in normal and cancer tissue from prostate cancer patient. Five normal and five cancer tissue cases on TMA were scored for choline kinase staining percentage and intensity and composite scores were calculated using two parameters. As shown in these figures, choline kinase enzyme is highly expressed in cancer tissue as opposed to normal tissue. Values and error bars shown in the figure represent mean and SE, respectively from three independent experiments (*, $p<0.05$ compared with Etn; ***, $p<0.0001$ compared with control).

Figure 13A:
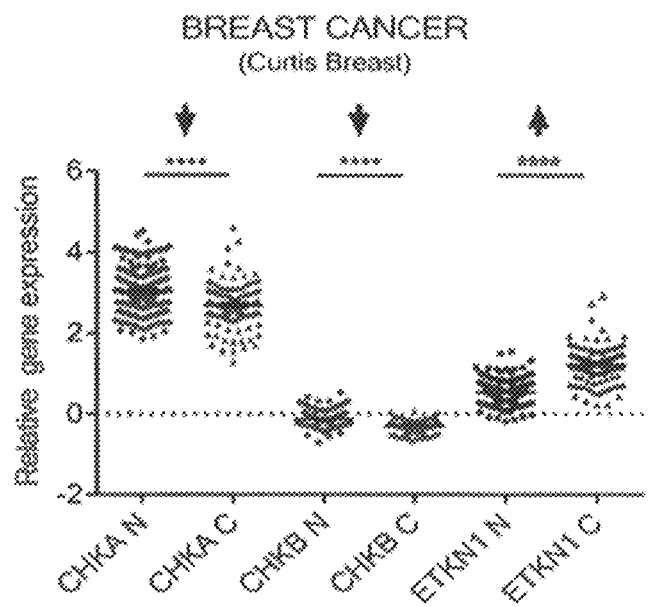
Figure 13B:
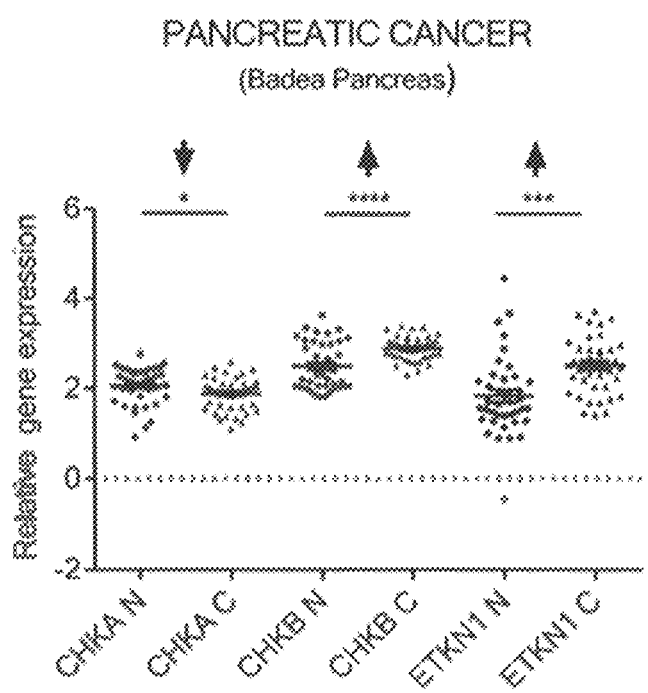
Figure 13C:
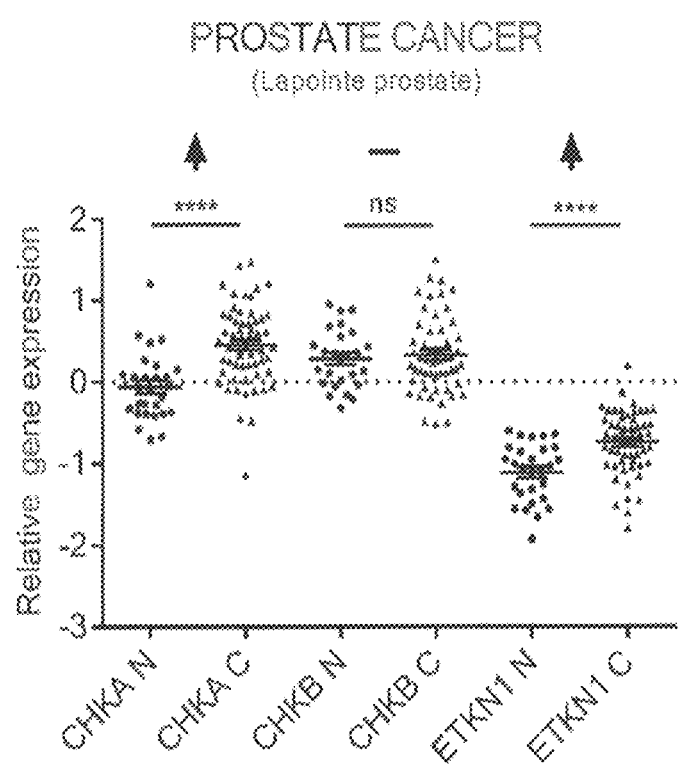

FIGS. 13A-13C shows In silico analysis of CK expression in breast cancer (FIG. 13A), pancreatic cancer (FIG. 13B) and prostate cancer (FIG. 13C). Expression level of CK-A, CK-B, EKI-1 in cancer tissue was analyzed using Oncomine (https://www.oncomine.org/resource/login.html). Reporter ID and platform for datasets used were as follows: gene rank CHKA-13786/19574, CHKB-4945/19574, ETNKI-5290/19574 analyzed on Human Genome U133 Plus2.0 Array.

Figure 14:
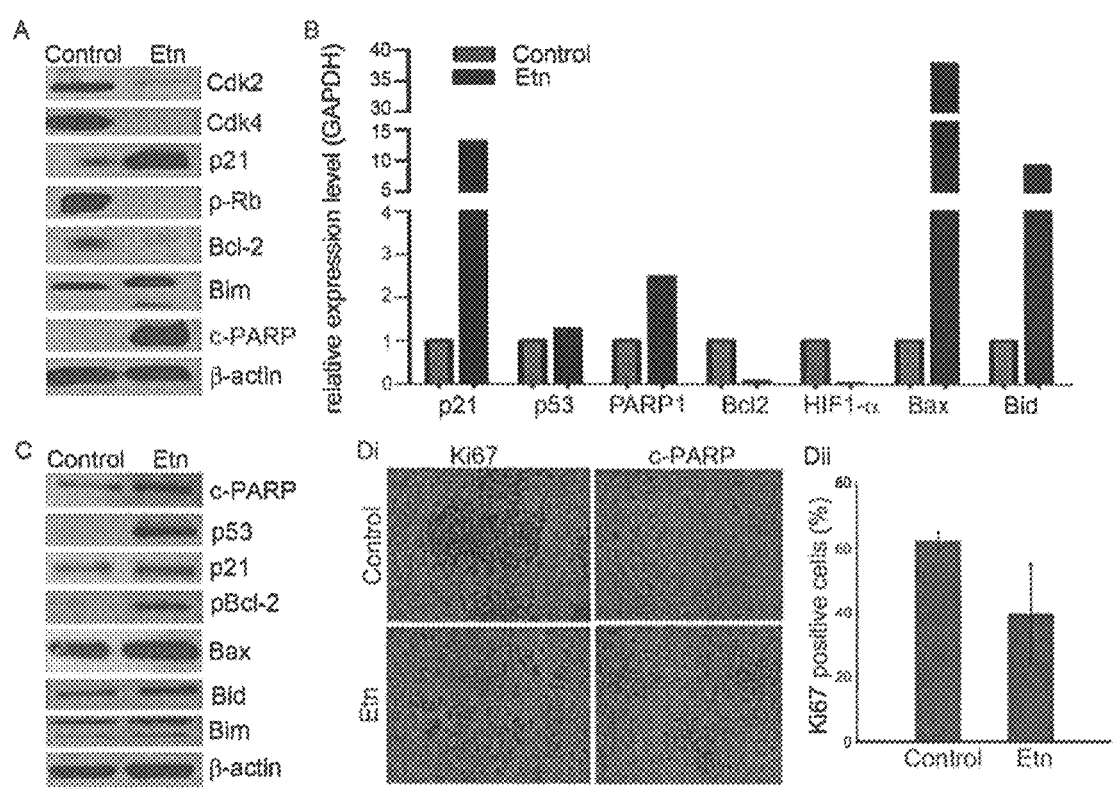
Figure 14:
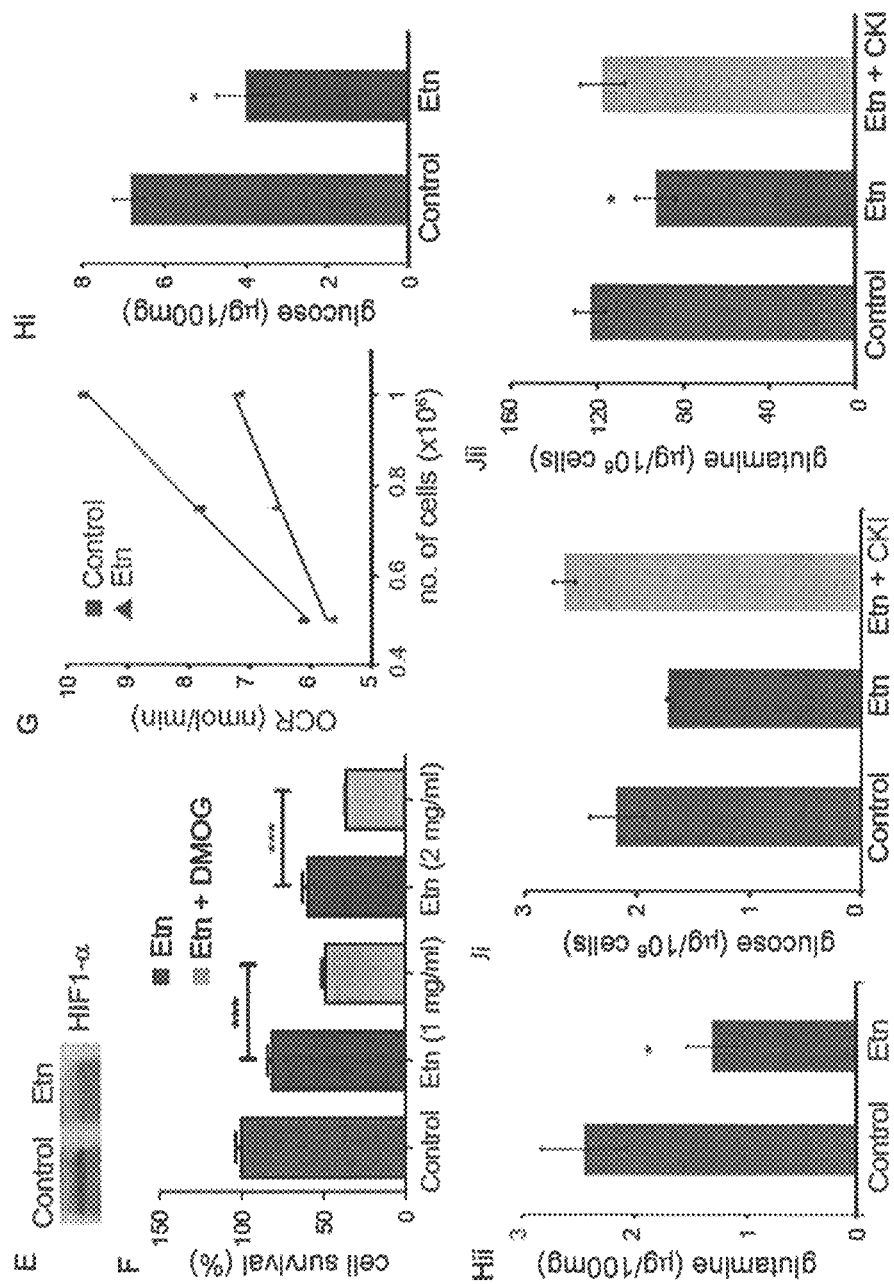

FIG. 14 shows that Etn activates mitochondrially-mediated death pathways and affects oxygen consumption rate (OCR) and cellular metabolism in cancer cells. (Panels A) Immunoblots of control and Etn-treated (2 mg/ml for 48 h) PC-3 cell lysates for molecular regulators of cell-cycle (pRb, Cdk4, Cdk2, p21) and apoptosis (c-PARP, Bim, and Bcl-2). Beta actin was used as a loading control. (Panel B) Relative transcription levels of p21, PARP1, Bcl-2, HIF1-α, Bax and Bid in control and Etn-treated (2 mg/ml for 48 h) PC-3 cells. RNA samples were run on MOPS agarose gel to check integrity and two clear bands were observed for each sample. (Panel C) Immunoblots of control and 40 mg/kg Etn-treated PC-3-luc tumors lysates for p53, p21, Bax, pBcl-2, c-PARP, Bim and Bid. β-actin was used as a loading control. (Panel Di) Micrographs showing immunohistochemical staining of Ki67 and c-PARP in control and Etn-treated PC-3-luc prostate xenografts. (Panel Dii) Quantification of Ki67 staining in control and Etn-treated prostate xenografts. (Panel E) Immunoblot showing effect of Etn treatment on HIF1-α expression level in PC-3 luc prostate xenografts. (Panel F) Effect of HIF1-α stabilization on Etn-induced cell death in PC-3 cells. PC-3 cells were pre-treated with 35 µg/mL DMOG (HIF1-α activator) for 4 h followed by treatment with 1 and 2 mg/ml Etn and DMOG together for 48 h and estimation of cell survival by MTT assay. (Panel G) Effect of Etn treatment on oxygen consumption rate (OCR) in PC-3 cells. PC-3 cells were treated with 2 mg/ml Etn for 48 h at pH 7.4 and cells were suspended at concentrations of $5\times10^5$/ml, $7.5\times10^5$/ml and $1\times10^6$/ml. OCR was measured using an oxygen electrode. Measurements were initiated by adding 500 µl of buffer control and 2 mg/ml Etn-treated cell suspension at various cell concentrations into electrode chamber pre-equilibrated with 500 µl fresh media. The plot shows representative OCRs as a function of cell number for control and Etn-treated cells. (Panels Hi, Hii) show intracellular glucose (Panel Hi) and glutamine (Panel Hii) levels in control and 40 mg/kg Etn-treated PC-3-luc tumors. Glucose and glutamine levels in control and Etn-treated tumors were estimated by LC-MS/MS. (Panels Ji and Jii) Effect of choline kinase inhibition on intracellular levels of glucose and glutamine in Etn-treated cells. Panels Ji and Jii show that treatment of PC-3 cells with 2 mg/ml Etn for 48 h reduced intracellular levels of glucose (Panel Ji) and glutamine (Panel Jii); these reductions were abrogated by inhibiting the activity of choline kinase. Values and error bars shown in the figures represent mean and SE, respectively from three independent experiments (*, $p<0.05$ compared with control; ***, $p<0.0001$ compared with Etn treatment).

Figure 15:
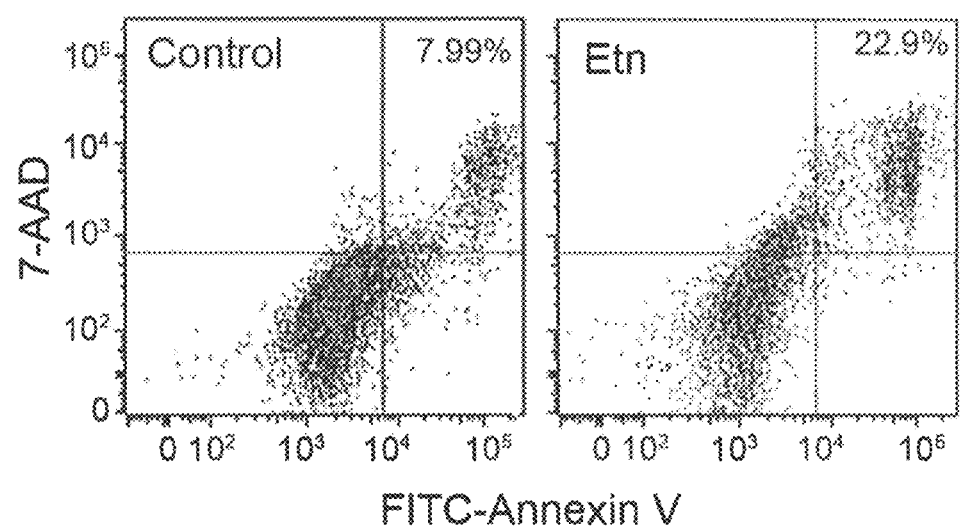

FIG. 15 shows induction of apoptosis by Etn as reflected in annexin V binding to PC-3 cells. Annexin V binding assays were performed for control and 2.0 mg/ml Etn-treated cells along with counterstaining with 7-AAD to distinguish between dead and apoptotic cells. Annexin V positive cells were analyzed using flow cytometry. Representative scatter plots for control and Etn-treated cells stained with 7-AAD and annexin V are shown.

Figure 16:
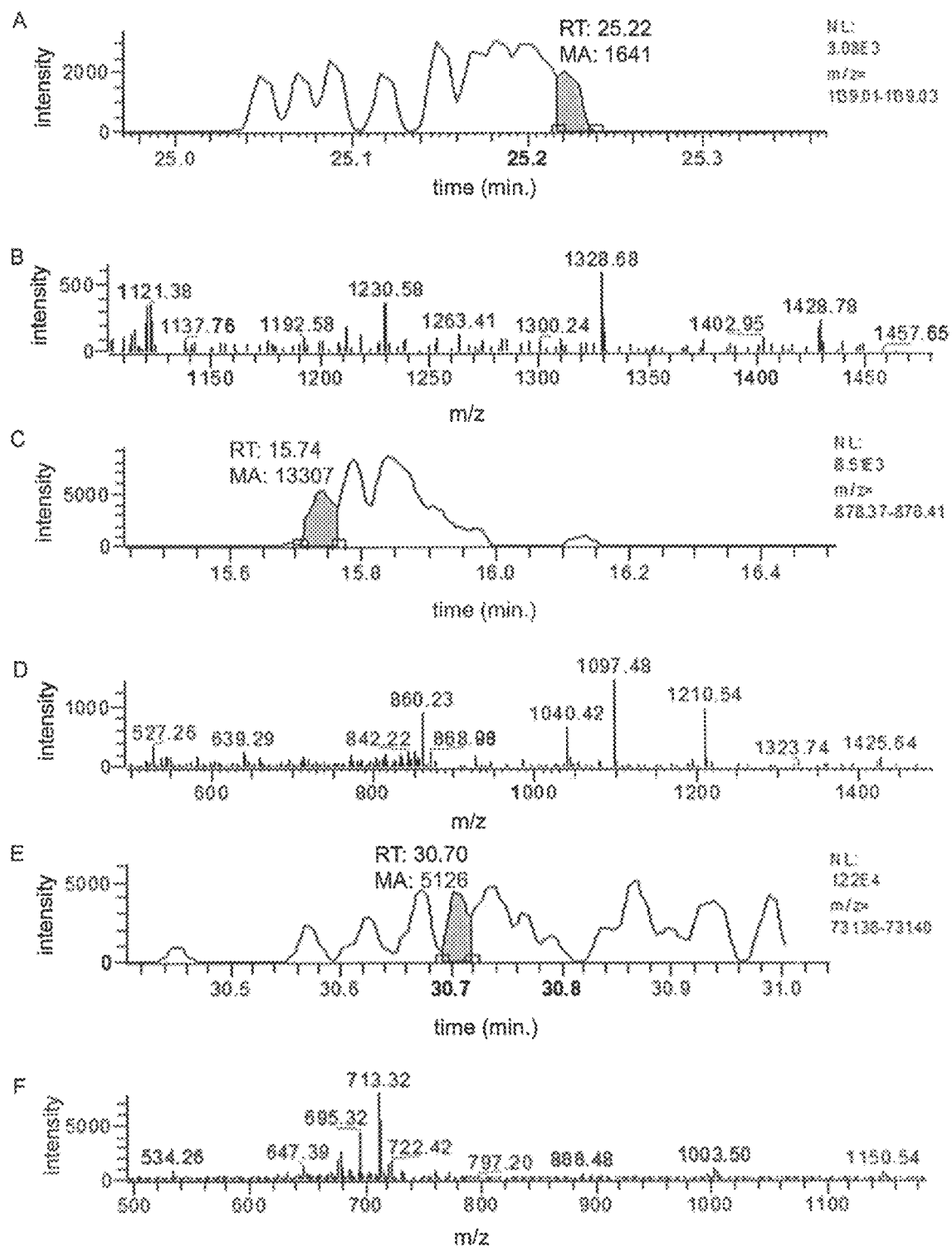

FIG. 16 shows label free LC-MS/MS quantitation of glyceraldehyde 3-phosphate dehydrogenase, phosphoglycerate kinase 1 and delta-1-pyrroline-5-carboxylate synthase. (Panel A) Integration of peptides digested from glyceraldehyde 3-phosphate dehydrogenase at a retention time 25.22 min with the qualitative ion at m/z 1139.02. (Panel B) $MS^2$ spectrum of ion m/z 1139.02. (Panel C) Integration of peptides digested from phosphoglycerate kinase 1 at retention time 15.74 min with the qualitative ion at m/z 878.39. (Panel D) $MS^2$ spectrum of ion m/z 878.39. (Panel E) Integration of peptides digested from Delta-1-pyrroline-5-carboxylate synthase at retention time 30.70 min with the qualitative ion at m/z 731.39. (Panel F) $MS^2$ spectrum of ion m/z 731.39.

Figure 17:
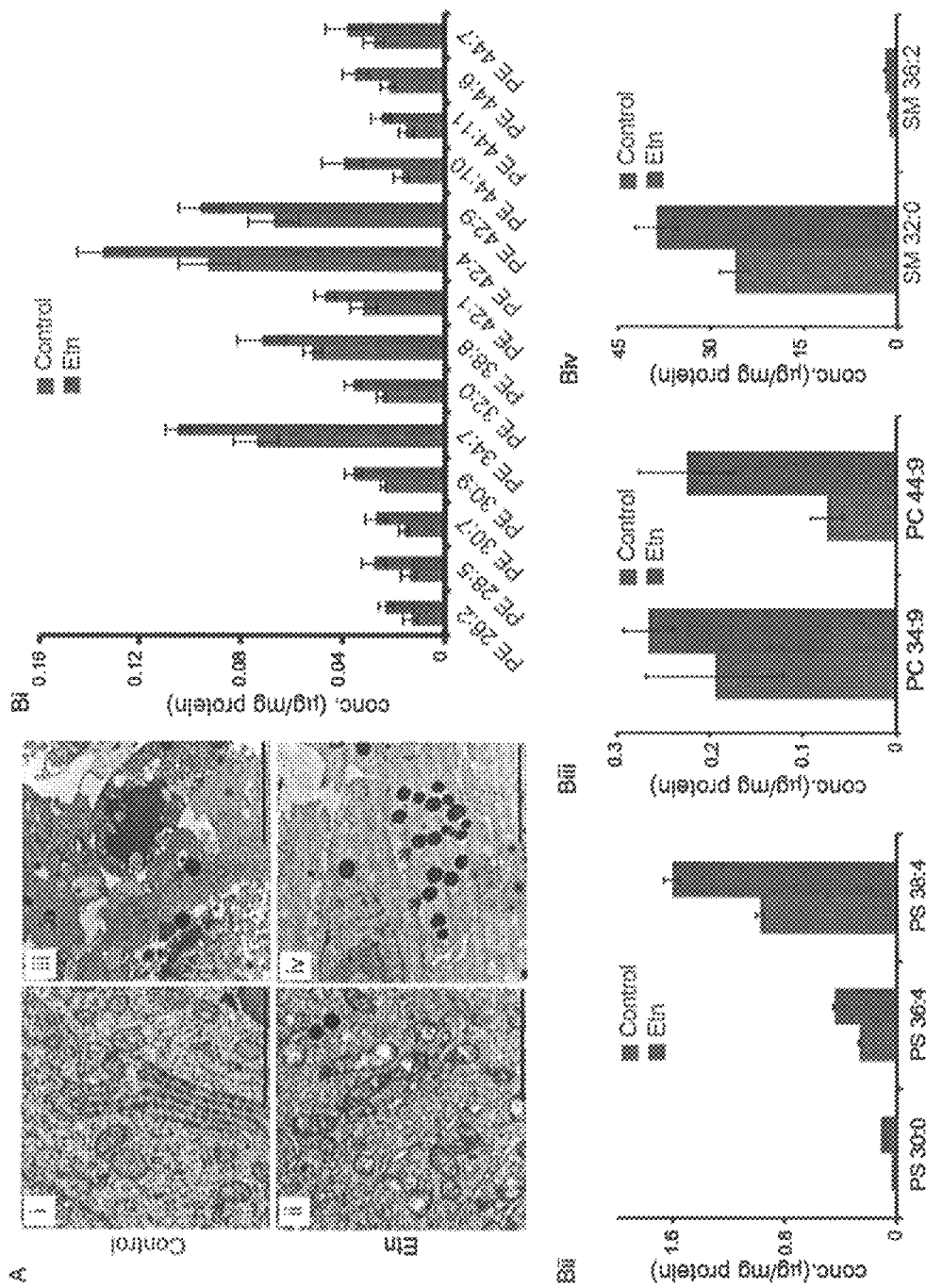
Figure 17:
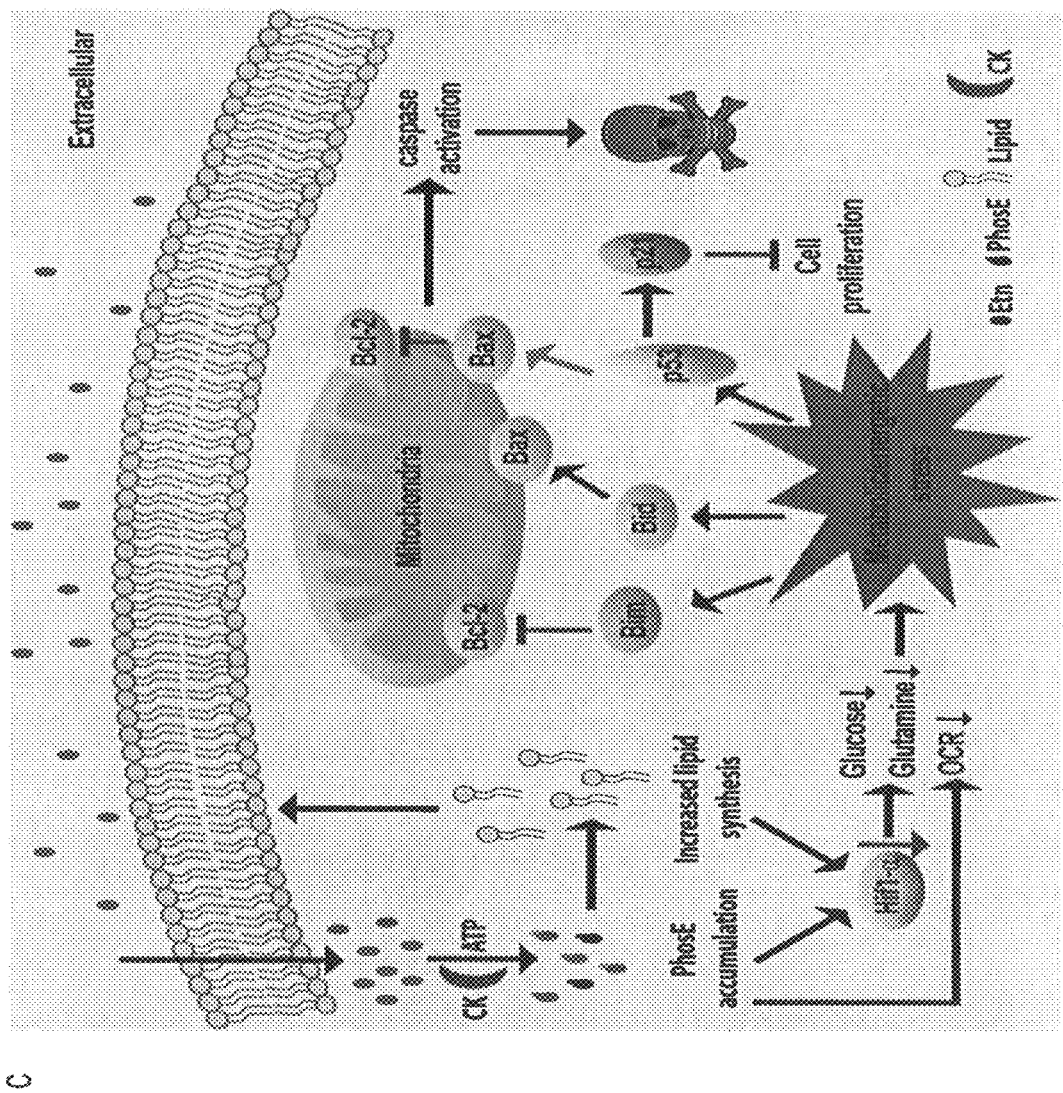
Figure 18A:
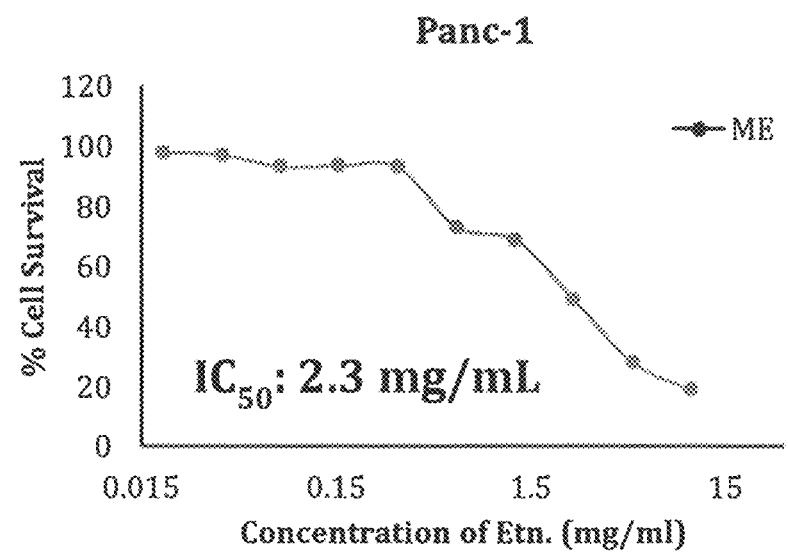
Figure 18B:
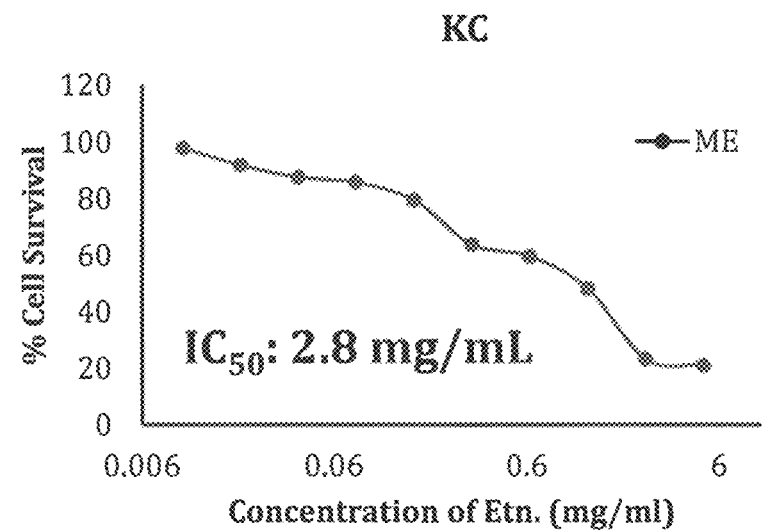
Figure 18C:
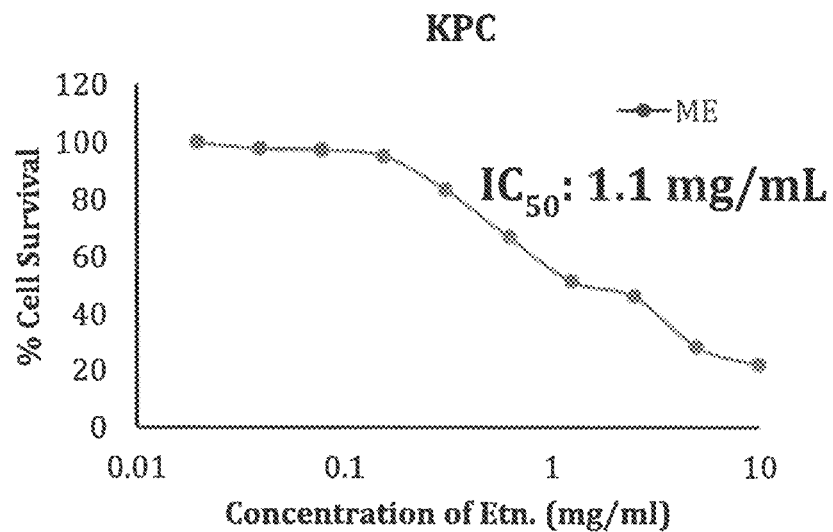
Figure 18D:
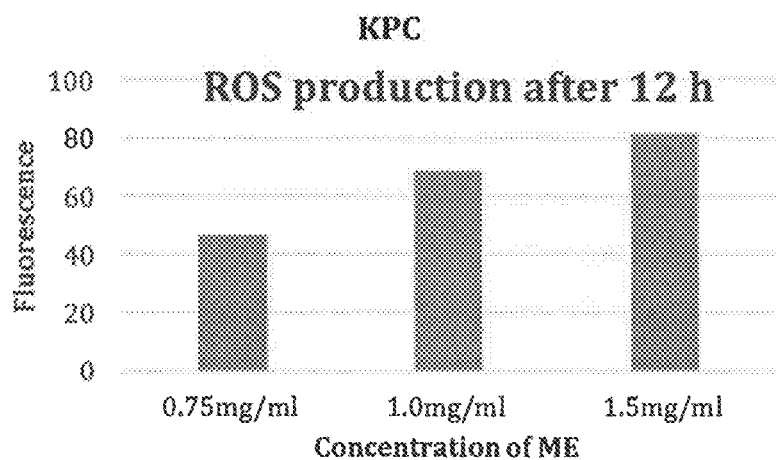

FIG. 17 shows the effects of Etn treatment on mitochondrial integrity and cellular lipids. (Panel A) Representative transmission electron micrographs of control and 40 mg/kg Etn-treated tumors showing changes in mitochondrial morphology and accumulation of lipids upon Etn treatment. Ultrathin sections were cut on Boeckeler MTx ultramicrotome, counterstained with lead citrate, and examined on a LEO 906e transmission electron microscope. Mitochondria and accumulated lipid granules are highlighted by red arrows in the panel. Treated tumors showed elongated mitochondria with degrading mitochondrial matrix (Panel Aii) and abundant lipid rich granules (Panel Aiv) in comparison to untreated control tumors (Panel Ai, Aiii). Left panels, scale bar=2 µM; Right panels, scale bar=5 µM. (Panel B) Etn treatment increases lipid levels in Etn-treated tumors. Levels of PE (Panel Bi), PS (Panel Bii), PC (Panel Biii) and SM (Panel Biv) lipids in control and Etn-treated tumors. In the abbreviation of lipid first and second numbers denote the number of carbon atoms and unsaturated bonds present in the lipid, respectively. Lipid amounts were quantified by LC-MS/MS analysis. Values and error bars shown in the figure represent mean and SE, respectively. (Panel C) Schematic diagram depicting proposed model for anticancer activity of Etn in prostate cancer cells. The model proposes that accumulation of PhosE and phospholipid downregulates HIF1-α, which precipitates a bioenergetics/metabolic crisis leading to activation of p53-mediated signaling cascade culminating into cell death.

FIGS. 18A-18D shows cell proliferation and colony survival after treatment with Etn/PhosE. Proliferation of cells Pane-1, KPC, and KC treated with Etn/PhosE was evaluated with MTT assay. ROS experiment protocol: Seed 20,000 cells/well for KPC and KC and 10,000 cells/well for Panel in a plate. Incubate the cells overnight for cell adherence. Remove media and wash the cells with HBSS. Add 20 µM H2DCFDA dissolved in the empty colorless basal DMEM medium and incubate the plate for 60 min/37° C. Remove the media and wash the cells with HBSS and treat the cells with ME (concentration based on $IC_{50}$). After the treatment remove the media and add HBSS. Read the plate using 492-495 nm excitation and 517-527 nm emission on the fluorescence plate reader.

DETAILED DESCRIPTION

The following detailed description is presented to enable any person skilled in the art to make and use the invention. For purposes of explanation, specific nomenclature is set forth to provide a thorough understanding of the present application. However, it will be apparent to one skilled in the art that these specific details are not required to practice the invention. Descriptions of specific applications are provided only as representative examples. The present application is not intended to be limited to the embodiments shown, but is to be accorded the widest possible scope consistent with the principles and features disclosed herein.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein.

The Kennedy pathway includes two parallel branches, one for phosphatidyl ethanolamine (PE) synthesis and the other for phosphatidylcholine (PC) synthesis. The PE synthesis pathway consists of three enzymatic steps. Ethanolamine kinase (EtnK) catalyzes the ATP-dependent phosphorylation of ethanolamine to form PhosE and ADP. ETnK is specific for ethanolamine; it does not catalyze the phosphorylation of choline. In the second, rate-limiting step, a CTP:phosphoethanolamine cytidyltransferase (ECT) uses PhosE and CTP to form the high-energy donor CDP-ethanolamine with the release of pyrophosphate. CDP-ethanolamine:1,2-diacylglycerol ethanolaminephosphotransferase (EPT) catalyzes the final step in the pathway, using CDP-ethanolamine and a lipid anchor, such as diacylglycerol (DAG) or alkyl-acylglycerol (AAG) to form PE and CMP.

The analogous pathway for PC synthesis uses a series of similar reactions, except for the involvement of choline instead of ethanolamine to form PC. However, in contrast to the PE pathway, the PC pathway includes several mammalian choline kinase (CK) isoforms with a choline/ethanolamine kinase (ChoK/EtnK) domain: ChoKα1 (NP_001268), ChoKα2 (NP_997634) and ChoKβ1 (NP_005189) that are able to phosphorylate both choline and ethanolamine. Previous studies suggest that ChoK acts as a dimeric protein forming different homo- or hetero-dimer isoform combinations resulting in different levels of ChoK activity, whereby the α/α homodimer is the most active choline kinase form, the β/β homodimer the least active, and the α/β heterodimer has an intermediate phenotype.

One aspect of the present application relates to a method for treating cancer, comprising orally administering to a subject in need thereof, an effective amount of a pharmaceutical composition comprising Etn, or a pharmaceutically acceptable salt thereof, and a pharmaceutically effective carrier.

As demonstrated herein below, Etn, the first precursor in Kennedy pathway of PE lipid synthesis (FIG. 1), was found to exhibit remarkable anticancer activity in both in vitro and in vivo models of prostate cancer. In addition, Etn was found to exhibit excellent bioavailability, GI tract stability, and no drug-drug interaction liability, attributes that are desirable in orally-delivered drugs. While not wishing to be bound by theory, it is believed that Etn treatment induces cell death by downregulation of HIF1-α, and is accompanied by depletion in cellular glucose and glutamine levels causing metabolic stress resulting in apoptosis. Etn appears to exploit the intrinsic overexpression of choline kinase enzyme in cancer cells that converts Etn to cytotoxic PhosE, without inflicting any toxicity.

The Etn used in the treatment methods of the present disclosure may be isolated and purified from a natural product or a processed product thereof, or a synthesized product. Ethanolamine can be produced by reacting ethylene oxide and ammonia. Ethanolamine can also be isolated and purified from a natural product or a processed product thereof by known techniques such as solvent extraction, various chromatographic methodologies and the like. Alternatively, ethanolamine may be obtained from commercial sources, for example, Sigma-Aldrich Co., Ltd. and the like.

In other embodiments, the method of treating cancer comprises administering to a subject in need thereof, an effective amount of a pharmaceutical composition comprising an analog of Etn, a prodrug of Etn, an Etn hybrid molecule or a pharmaceutically acceptable salt thereof; and a pharmaceutically effective carrier. In certain embodiments, the pharmaceutical compositions may further include one or more additional anticancer agents. Exemplary anticancer agents include anti-mitotic agents, anti-interphase agents, anti-microtubule agents, anthracycline-based agents, aromatase inhibitor agents, anti-angiogenesis agents, immune checkpoint regulators, and combinations thereof.

In some embodiments, the pharmaceutical composition is administered by oral, intravenous, intraperitoneal, subcutaneous, intranasal or dermal administration. In some embodiment, wherein the pharmaceutical composition is administered as a solid or semi-solid in capsules.

In certain embodiments, the Etn analog is a compound represented by the following formula: X—$CH_2$—$CH_2$—O—Y, where X is $R^1$—N($R^2$)— [$R^1$ and $R^2$ are the same or different and each is a hydrogen atom or an amino-protecting group] or $R^3$—CH—N— [$R^3$—CH is H—CH or a Shiff base type amino-protecting group]; and Y is —P(=O)(OH)—O—$R^4$ [$R^4$ is —$CH_2$—CH(O—$R^5$)—$CH_2$—O—$R^6$' ($R^5$ and $R^6$ are the same or different and each is an acyl group having 2-30 carbon atoms or a hydrogen atom) or a hydrogen atom], a hydrogen atom or a hydroxy-protecting group.

In other embodiments, $R^1$ and $R^2$ are the same or different and each is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms, and $R^3$ is a hydrogen atom, a halogen atom, a hydroxy group, an aryl group, an acyl group having 2-30 carbon atoms, an alkyl group having 1-6 carbon atoms, an alkoxyl group having 1-6 carbon atoms, a hydroxyalkyl group having 1-6 carbon atoms, a haloalkyl group having 1-6 carbon atoms, a haloalkoxyl group having 1-6 carbon atoms or a halohydroxyalkyl group having 1-6 carbon atoms.

Exemplary Etn analogs include phosphoethanolamine, monomethylethanolamine, dimethylethanolamine, N-acylphosphatidylethanolamine, phosphatidylethanolamine, and lysophosphatidylethanolamine and may include any of the Etn analogs described in U.S. Patent Application Publication No. 2015/0329832.

As used herein, the term "Etn prodrug" refers to any compound that when administered to a biological system generates a biologically active Etn compound as a result of spontaneous chemical reaction(s), enzyme catalyzed chemical reaction(s), and/or metabolic chemical reaction(s), or a combination of each. Standard Etn prodrugs may be formed using groups attached to functionality, e.g., HO—, HS—, HOOC—, $HOOPR_2$—, associated with the drug, that cleave in vivo. Table 1 below represents various bonds that can be used to produce Etn pro-drugs or Etn hybrid molecules, as further discussed below.

TABLE 1

Chemical bonds that can be used to produce pro-drugs or hybrid molecules

| Bonds that are labile for hydrolysis Ethanolamine can be linked through these bonds for producing a pro-drug and hybrid molecule | Carbonate |
|---|---|
| | Ester |
| | Urethane |
| | Anhydride |

Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Etn prodrugs undergo a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Exemplary Etn prodrugs are depicted in Table 2 below.

In certain embodiments further exemplified in Table 2 (i.e., molecule numbers x-y), the pharmaceutical composition includes a hybrid molecule of Etn and another chemotherapeutic drug. As used herein, the term "Etn hybrid" refers to For example, Etn hybrids of belinostat, panobinostat and vorinostat are shown in Table 2, molecule numbers 36 to 41, respectively. Any chemotherapeutic drug described herein may be used in a hybrid form with Etn provided that it contains a sufficient reactive group for forming the hybrid molecule with conjugation using an ester, carbonate, urethane, anhydride. The hydroxyl or amino group of Etn may be at the terminal end of the hybrid structure. Exemplary Etn hybrids include compounds listed in Table 2.

TABLE 2
Etn prodrugs and Etn hybrid molecules
1  2-aminoethyl (E)-4-(4-hydroxy-3-methoxy-phenyl)but-2-enoate
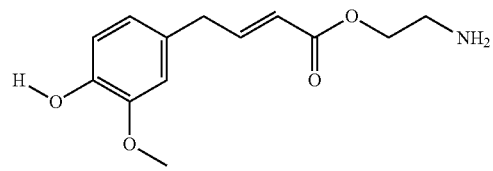
2  2-aminoethyl (E)-3-(4-hydroxy-3-methoxy-phenyl)prop-2-enoate
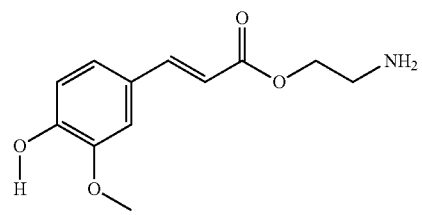
3  2-aminoethyl 4-hydroxy-3-methoxy-benzoate
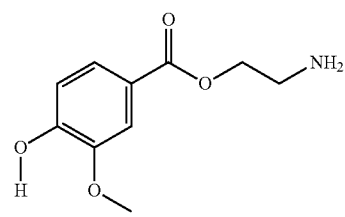
4  2-aminoethyl 5-[(3R)-dithiolan-3-yl]pentanoate
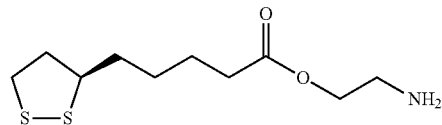
5  2-aminoethyl octanoate
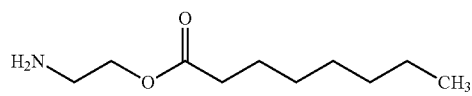
6  2-aminoethyl 4-hydroxy-3-methoxy-benzoate
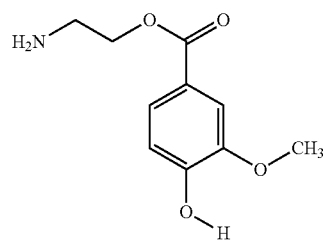
7  2-aminoethyl (5E,8E,11E,14E,17E)-icosa-5,8,11,14,17-pentaenoate
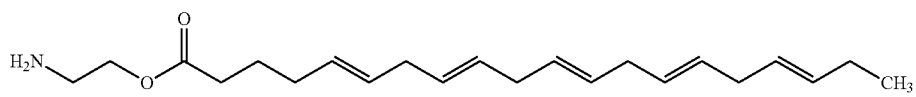

TABLE 2-continued
Etn prodrugs and Etn hybrid molecules
| 8 | 2-aminoethyl decanoate |
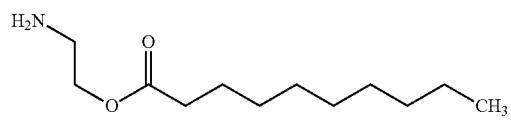
| 9 | 2-aminoethyl 2-acetoxybenzoate |
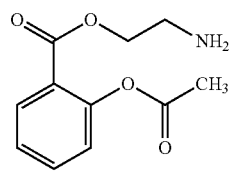
| 10 | 2-aminoethyl 2-(4-isobutylphenyl)propanoate |
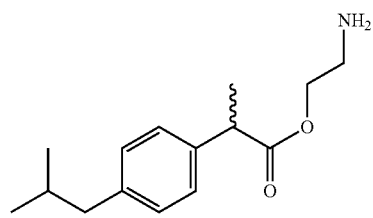
| 11 | 2-aminoethyl (2S)-2-(6-methoxy-2-naphthyl)propanoate |
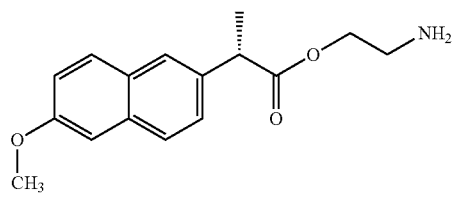
| 12 | 2-aminoethyl 2-[1-(4-chlorobenzyl)-5-methoxy-2-methyl-indol-3-yl]acetate |
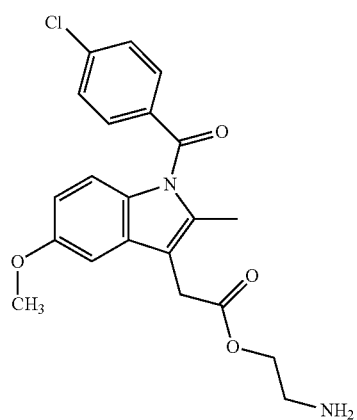
| 13 | 2-aminoethyl dodecanoate |
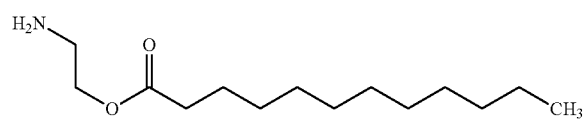

TABLE 2-continued
Etn prodrugs and Etn hybrid molecules
14     2-aminoethyl tetradecanoate
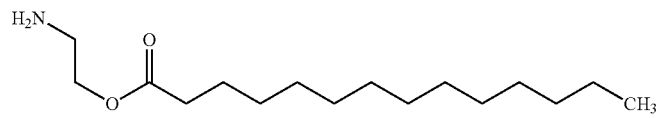
15     2-aminoethyl hexadecanoate
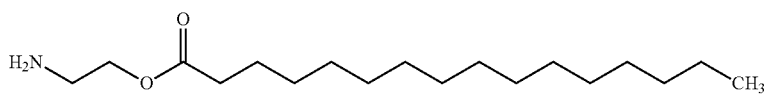
16     bis(2-aminoethyl)hexanedioate
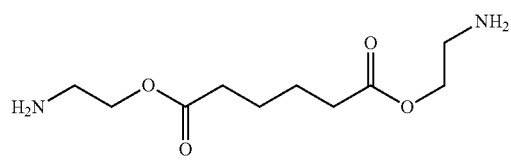
17     2-aminoethyl (3S)-3-amino-4-[(1-benzyl-2-methoxy-2-oxo-ethyl)amino]-4-oxo-butanoate
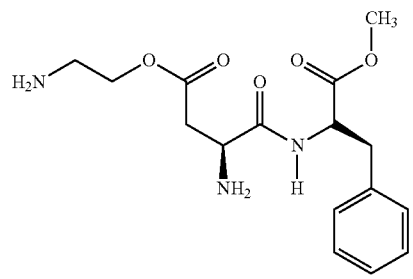
18     2-aminoethyl (E)-octadec-9-enoate
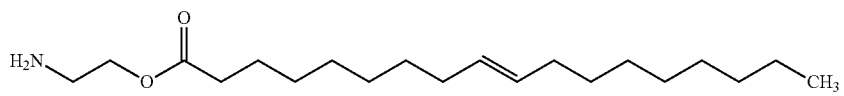
19     2-aminoethyl (9E,11E)-octadeca-9,11-dienoate
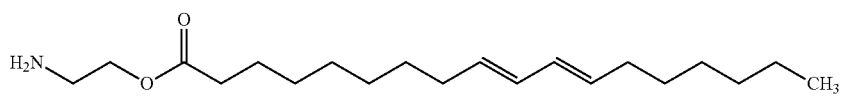
20     2-aminoethyl octadecanoate
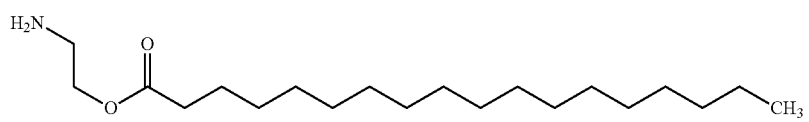
21     2-aminoethyl (9E,11E,13E)-octadeca-9,11,13-trienoate
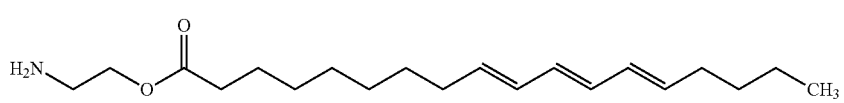

TABLE 2-continued
Etn prodrugs and Etn hybrid molecules
| 22 | 2-aminoethyl (E)-docos-13-enoate |
|---|---|
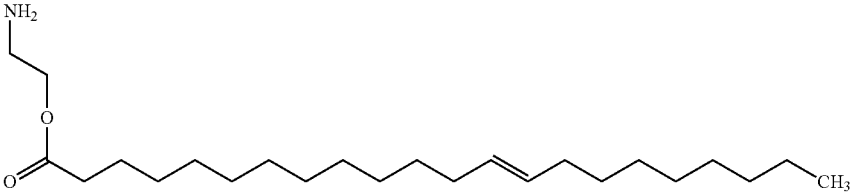
| 23 | 2-aminoethyl icosanoate |
|---|---|
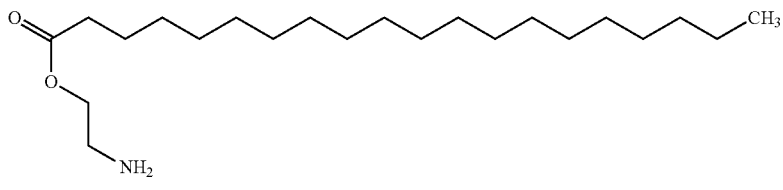
| 24 | 2-aminoethyl docosanoate |
|---|---|
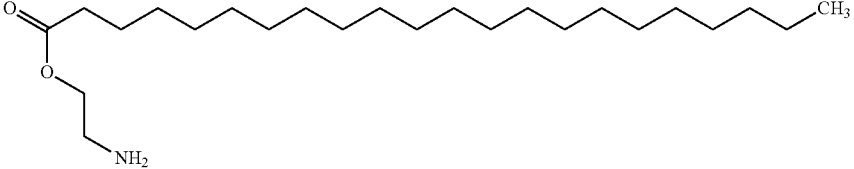
| 25 | 2-aminoethyl tetracosanoate |
|---|---|
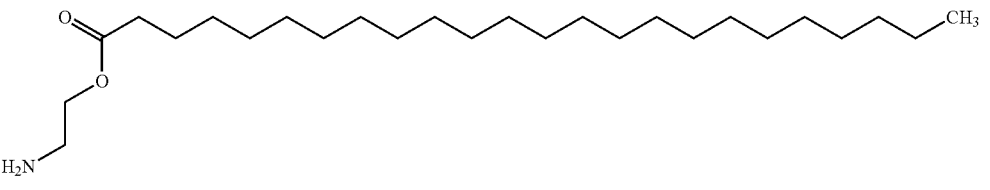
| 26 | 2-aminoethyl (2R)-2-amino-4-methyl-pentanoate |
|---|---|
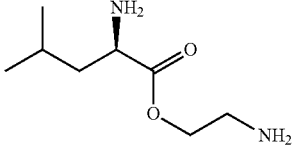
| 27 | 2-aminoethyl (2E,4E)-hexa-2,4-dienoate |
|---|---|
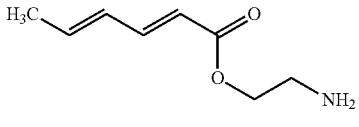
| 28 | 2-aminoethyl 2-amino-4-methylsulfanyl-butanoate |
|---|---|
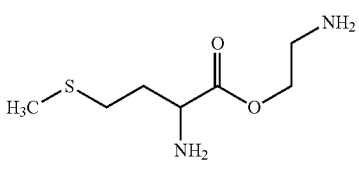

TABLE 2-continued
Etn prodrugs and Etn hybrid molecules
29  2-aminoethyl 4-hydroxy-
3-methoxy-benzoate
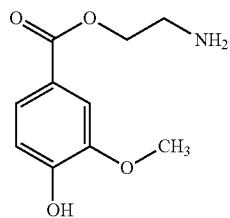
30  2-aminoethyl pyridine-3-
carboxylate
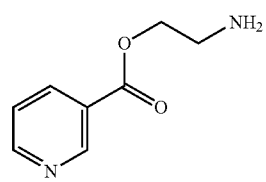
31  2-aminoethyl 3-[(4-tert-butylcyclohexyl)
methyl]-1,4-dioxo-naphthalene-
2-carboxylate
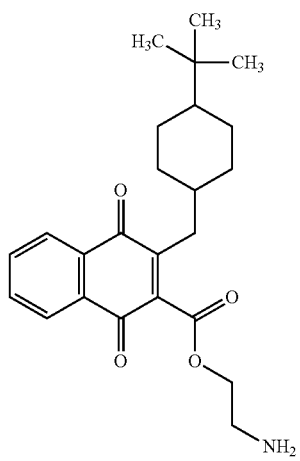
32
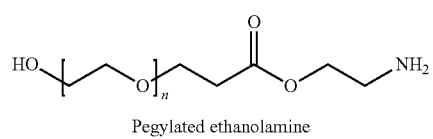
Pegylated ethanolamine TABLE 2-continued
Etn prodrugs and Etn hybrid molecules
33     2-aminoethyl 4-(4-amino-3-hydroxy-5-methyl-tetrahydropyran-2-yl)oxy-2,5,7,12-tetrahydroxy-6,11-dioxo-6a,10a-dihydro-1H-tetracene-2-carboxylate
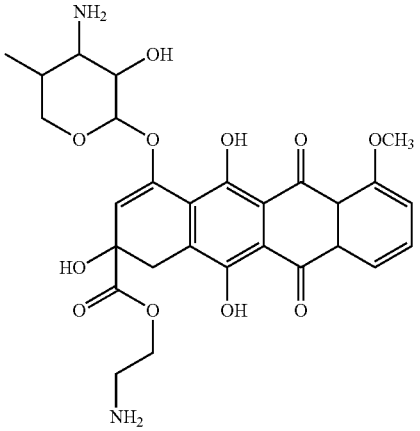
34
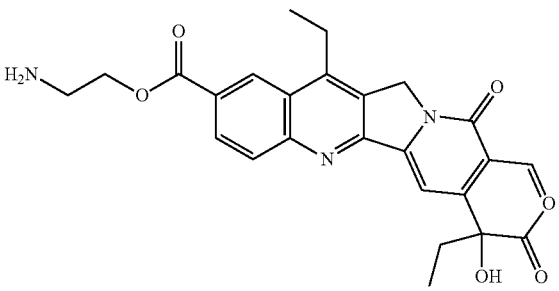
35     2-aminoethyl N-[1-(3,4-dihydroxy-5-methyl-tetrahydrofuran-2-yl)-5-fluoro-2-oxo-pyrimidin-4-yl]carbamate
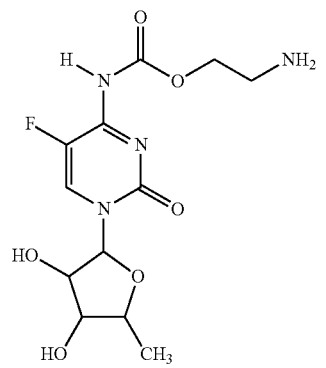
36     2-aminoethyl (E)-3-[3-(phenylsulfamoyl)phenyl]prop-2-enoate
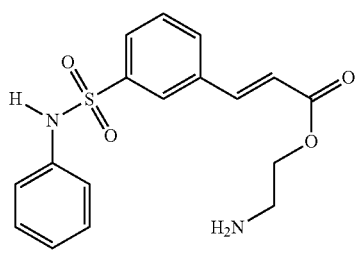

TABLE 2-continued

Etn prodrugs and Etn hybrid molecules

| | |
|---|---|
| 37 | (E)-N-(2-hydroxyethyl)-3-[3-(phenylsulfamoyl)phenyl]prop-2-enamide |
| 38 | 2-aminoethyl (E)-3-[4-[[2-(2-methylindolin-3-yl)ethylamino]methyl]phenyl]prop-2-enoate |
| 39 | 2-aminoethyl (E)-3-[4-[(8b-hydroxy-1,2,3a,4-tetrahydropyrrolo[2,3-b]indol-3-yl)methyl]phenyl]prop-2-enoate |
| 40 | N-(2-hydroxyethyl)-N'-phenyl-butanediamide |
| 41 | 2-aminoethyl 4-anilino-4-oxo-butanoate |

TABLE 2-continued

Etn prodrugs and Etn hybrid molecules

42

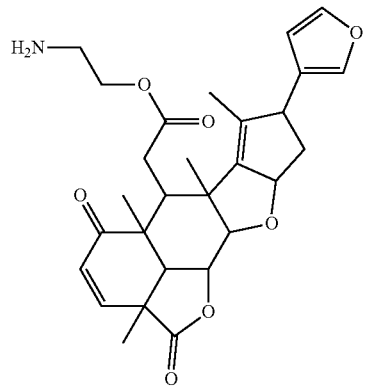 [SMILES: CC1=C2C(CC1c1ccoc1)OC1C3OC(=O)C4(C)C=CC(=O)C(C)(C34)C(CC(=O)OCCN)C21C]

43  2-aminoethyl 3,4,5,6-tetraacetoxytetra-
hydropyran-2-carboxylate

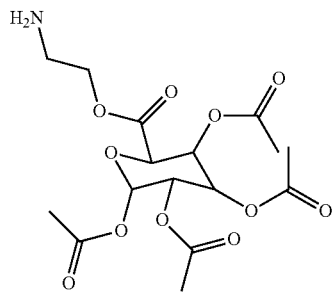

In some embodiments, Etn is conjugated to a polymer. Examples of such polymers include, but are not limited to, polyethylene glycol (PEG), N-2-hydroxypropyl mehtacrylamide (HPMA), polyvinyl pyrrolidone (PVP), polyvinyl alcohol, polyglutamic acid (PGA), polymalic acid, glycylphenylalanylleucylglycine (GFLG)-lysosomal cleavage linker, dendrimers—polyethyleneimine and polyamido amine (PAMAM), polymeric micelles such as propylene oxide, L-lysine, caprolactone, D,L-lactic acid, styrene, aspartic acid, (J-benzoyl-L-aspartate and spermine, biodegradable polymers such as poly (L-lysine), poly (L-glutamic acid) and poly (N-hydroxyalkyl)glutamine), carbohydrate polymers such as dextrins, hydroxyethyl starch (HES) and polysialic acid, smart polymers such as poly (acrylamide), poly (methylacrylic acid), poly (acrylic acid) and poly(2-(dimethylamino)ethyl methacrylate. Table 3 provides a classification of exemplary polymers for conjugation.

TABLE 3

Classification of exemplary polymers.

| Classification | Polymer |
| --- | --- |
| Natural Polymers | |
| Protein based polymers | Collagen, albumin, gelatin |
| Polysaccharides | Agarose, alginate, carrageenan, hyaluronic acid, dextran, chitosan, cyclodextrins |
| Synthetic polymers-Biodegradable | |
| Polyesters | Poly(lactic acid), poly(glycolic acid), poly(hydroxyl butyrate), poly(ε-caprolactone), poly(β-malic acid), poly(dioxanones) |
| Polyanhydrides | Poly(sebacic acid), poly(adipic acid), Poly(terphthalic acid) and various copolymers |
| Polyamides | Poly(imino carbonates), polyamino acids |
| Phosphorous-based polymers | Polyphosphates, polyphosphonates, polyphosphazenes |
| Others | Poly(cyano acrylates), polyurethanes, polyortho esters, polydihydropyrans, polyacetals |

TABLE 3-continued

Classification of exemplary polymers.

| Classification | Polymer |
| --- | --- |
| Synthetic polymers-Non-biodegradable | |
| Cellulose derivatives | Carboxymethyl cellulose, ethyl cellulose, cellulose acetate, cellulose acetate propionate, hydroxypropyl methyl cellulose |
| Silicones | Polydimethylsiloxane, colloidal silica |
| Acrylic polymers | Polymethacrylates, poly(methyl methacrylate), poly hydro (ethyl-methacrylate) |
| Others | Polyvinyl pyrrolidone, ethyl vinyl acetate, poloxamers, poloxamines |

In some embodiments, the pharmaceutical composition comprises Etn or Etn conjugates in the form of nanosomes, liposome, noisome, nanoparticle, nanosphere, microsphere, microparticle, microemulsion, nanosuspension and/or micelles.

Figure 1:
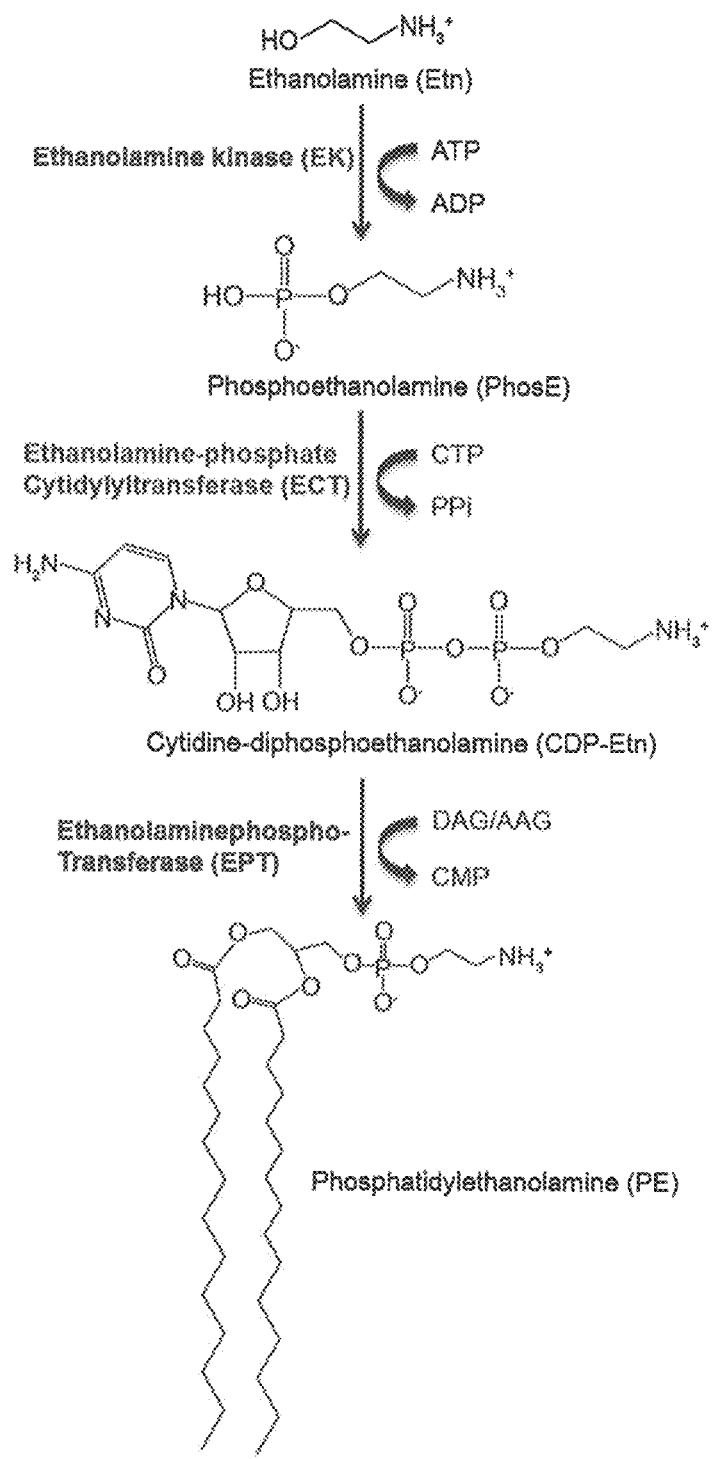
FIG. 1 depicts the Kennedy pathway of PE lipid biosynthesis. This pathway consists of three enzymatic steps. In the first step of the pathway, Etn gets converted into PhosE by ethanolamine kinase. Second step is the rate-limiting step and involves the formation of high energy donor CDP-ethanolamine and this step is catalyzed by ethanolamine-phosphate cytidylyltransferase. In the final step, PhosE is transferred to either diacylglycerol or alkyl-acylglycerol to form PE lipid employing ethanolaminephosphotransferase.

In other embodiments, the composition alternatively or additionally includes one or more substrate or product compounds of the Kennedy pathway of PE lipid biosynthesis (FIG. 1). Exemplary compounds include one or more members selected from the group consisting of PhosE, cytidine-diphosphoethanolamine (CDP-Etn), phosphatidylethanolamine, analogues therefrom, derivatives therefrom, and combinations thereof.

In one embodiment, the composition further includes PhosE. In some embodiments, the composition includes PhosE in an amount that is 5% (w/w) or less, 10% (w/w) or less, 20% (w/w) or less, 30% (w/w) or less, 40% (w/w) or less, 50% (w/w) or less, 60% (w/w) or less, 70% (w/w) or less, 80% (w/w) or less, 90% (w/w) or less, or 100% (w/w) or less of the amount of Etn. In another embodiment, the composition is free of PhosE. As used herein, a composition is "free of PhosE" if the composition does not contain any PhosE, or contains PhosE at levels below 0.1% w/w.

In another embodiment, the composition alternatively or additionally includes one or more substrate or product compounds of the Kennedy pathway of phosphatidylserine, lipid biosynthesis. Exemplary compounds include one or more members selected from the group consisting of choline, phosphocholine, cytidine-diphosphocholine, phosphatidylcholine, analogous therefrom, derivatives therefrom, and combinations therefrom.

In certain embodiments, the patient is also administered one or more centrosome declustering agents, including but not limited to griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, N2-benzyl-5-nitro-2-furamide, an anthracine compound as described in U.S. Patent Application Publication 2008/0051463; a 5-nitrofuran-2-carboxamide derivative as described in U.S. Provisional Application 61/619,780; and derivatives and analogs therefrom.

In others embodiments, the patient is also administered an inhibitor of HSET, a key mediator of centrosome clustering. In some embodiments, the inhibitor of HSET is a small molecule drug inhibiting the activity and/or expression of HSET in the targeted cell. Alternatively, or in addition, the patient may be administered an inhibitor of a protein that is upregulated with HSET or inhibitors of other proteins implicated in centrosome clustering. HSET co-regulated product targets include, but are not limited to Npap60L, CAS, Prc1, Ki67, survivin, phospho-survivin, Hif1α, aurora kinase B, p-Bcl2, Mad1, Plk1, FoxM1, KPNA2, Aurora A and combinations thereof. In other embodiments, the patient is administered one or more agents that block the nuclear accumulation of HSET during interphase.

In certain embodiments, the small molecule drug targets the motor domain of HSET and/or specifically binds to the HSET/microtubule binary complex so as to inhibit HSET's microtubule-stimulated and/or microtubule-independent ATPase activities. In a specific embodiment, the small molecule drug is AZ82 or CW069 or a therapeutically effective derivative, salt, enantiomer, or analog thereof.

AZ82 binds specifically to the KIFC1/microtubule (MT) binary complex and inhibits the MT-stimulated KIFC1 enzymatic activity in an ATP-competitive and MT-noncompetitive manner with a Ki of 0.043 µM. Treatment with AZ82 causes centrosome declustering in BT-549 breast cancer cells with amplified centrosomes.

Alternatively, or in addition, the patient may be administered with a poly(ADP-ribose) polymerase (PARP) inhibitor, an inhibitor of the Ras/MAPK pathway, an inhibitor of the PI3K/AKT/mTOR pathway, an inhibitor of FoxM1, Hif1α, survivin, Aurora, Plk1 or a combination thereof. Exemplary PARP inhibitors include, but are not limited to olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof. Exemplary Ras/MAPK pathway agents include, but are not limited to MAP/ERK kinase (MEK) inhibitors, such as trametinib, selumetinib, cobimetinib, CI-1040, PD0325901, AS703026, RO4987655, RO5068760, AZD6244, GSK1120212, TAK-733, U0126, MEK162, GDC-0973 and combinations thereof. Exemplary PI3K/AKT/mTOR pathway inhibitors include, but are not limited to everolimus, temsirolimus, GSK2126458, BEZ235, PIK90, PI1103 and combinations thereof.

Anti-angiogenesis inhibitors include small molecule agents or antagonists targeting the VEGF pathway, the Tie2 pathway, or both. Exemplary small molecule antagonists of the VEGF pathway include multikinase inhibitors of VEGFR-2, including sunitinib, sorafenib, cediranib, pazonpanib and nintedanib. Tie2 binding antagonists also include the small molecule inhibitors, CGI-1842 (CGI Pharmaceuticals), LP-590 (Locus Pharmaceuticals), ACTB-1003 (Act Biotech/Bayer AG), CEP-11981 (Cephalon/Teva), MGCD265 (Methylgene), Regorafenib (Bayer), Cabozantinib/XL-184/BMS-907351 (Exelixis), Foretnib (Exelixis), MGCD-265 (MethylGene Inc.).

In recent years, a number of immune checkpoint regulators in the form of receptors and their ligands have been identified. Immune checkpoint regulators include, but are not limited to PD-1 and its ligands, PD-L and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; T cell Ig and ITIM domain (TIGIT) and its CD155 ligand; CD122 and its CD122R ligand; CD70, glucocorticoid-induced TNFR family-related protein (GITR), B7H3, B and T lymphocyte attenuator (BTLA), and VISTA (Le Mercier et al., Front. Immunol., (6), Article 418, 2015). In addition, a number of checkpoint regulator inhibitors have been identified and tested in various clinical and pre-clinical models and/or approved by the FDA (Kyi et al., FEBS Letters, 588:368-376 (2014). The concept of inhibitory receptor blockade, also known as immune checkpoint blockade, has been validated in humans with the approval of the anti-CTLA-4 antibody ipilimumab for metastatic melanoma.

Adjuvant chemotherapeutic compositions may also include wide variety of cytotoxic agents with different intracellular targets that can induce apoptosis. This means that the cytotoxic activity of cytotoxic drugs is not solely dependent on specific drug-target interaction, but also on the activity of apoptotic (cell signaling) machinery of the cancer cell. Examples of cytotoxic agents include, but are not limited to, platinum-based drugs (e.g., carboplatin, cisplatin, oxaliplatin, satraplatin, triplatin tetranin, and carboplatin etc.), natural phenols (e.g., cardamom, curcumin, galangal, ginger, melegueta pepper, turmeric, etc.), plant alkaloids and taxanes (e.g., camptothecin, docetaxel, paclitaxel, vinblastine, vincristine, virorelbine, vincristine, etc.), other alkylating agents (e.g., altretamine, busulfan, carmustine, chlorambucil, cyclophosphamide, dacarbazine, ethylenimines, haxmethyl melamine, hydrazines, ifosfamide, lomustine, mechlorethamine, melphalan, nitrosoureas, piperine, procarbazine, streptozocin, temozolomide, thiotepa, triazines, etc.), tumor antibiotics and anthracyclines (e.g., bleomycin, chromomycin, dactinomycin, daunorubicin, doxorubicin, epirubicin, idarubicin, mitomycin, mitoxantrone, plicamycin, etc.), topoisomerase inhibitors (e.g., amsacrine, etoposides, irinotecan, teniposides, toptecan, etc.), antimetabolites (e.g., 5-fluorouracil, 6-thioguanine, 6-mercaptopurine, adenosine deaminase inhibitors, capecitabine, cladribine, cytarabine, foxuridine, fludarabine, gemcitabine, methotrexate, nelerabine, pentaostatin mitotic inhibitor, purine antagonists, pyrimidine antagonists, etc.), miscellaneous anticancer agents (e.g., ixabepilone, asparaginase, bexarotene, estramustine, hydroxyurea, isotretinoin, mitotane, pegaspargase, retinoids, tretinoin, etc.), combinations thereof, and pharmaceutically acceptable salts thereof.

Because of its basic amino group and the hydroxyl group, Etn has properties resembling those of both amines and alcohols. Thus, they can form salts with acids, and the hydroxyl group permits ester formation. When Etn reacts with organic acids, salt formation always takes place in preference to ester formation.

In certain embodiments, the active agent(s), including Etn, may be administered as a pharmaceutically acceptable salt. The active agents may be administered as an inorganic acid salt, organic acid salt or an organic-substituted inorganic acid salt. As used herein, the term "pharmaceutically acceptable salt" means a salt prepared from a base or an acid which is acceptable for administration to a patient, such as a mammal (for example, salts having acceptable mammalian safety for a given dosage regime). Pharmaceutically acceptable salts can be derived from pharmaceutically acceptable inorganic or organic acids or from pharmaceutically acceptable inorganic or organic bases.

Pharmaceutically acceptable acid addition salts may be prepared from inorganic acids, organic acids or organic-substituted inorganic acids. Salts derived from pharmaceutically acceptable inorganic acids include salts of boric acid, carbonic acid, hydrohalic acids (e.g., hydrobromic acid, hydrochloric acid, hydrofluoric acid or hydroiodic acid); nitric acid, phosphoric acid, sulfamic acid, sulfuric acid, and the like.

Salts derived from pharmaceutically acceptable organic acids include salts of aliphatic hydroxyl acids (for example, citric acid, gluconic acid, glycolic acid, lactic acid, lactobionic acid, malic acid, and tartaric acid); aliphatic monocarboxylic acids (for example, acetic acid, butyric acid, formic acid, propionic acid and trifluoroacetic acid); amino acids (for example, aspartic acid and glutamic acid); aromatic carboxylic acids (for example, benzoic, p-chlorobenzoic acid, diphenylacetic acid, gentisic acid, hippuric acid, and triphenylacetic acid), aromatic hydroxyl acids (for example, o-hydroxybenzoic acid, p-hydroxybenzoic acid, 1-hydroxynaphthalene-2-carboxylic acid and 3-hydroxynaphthalene-2-carboxylic acid); ascorbic acid, dicarboxylic acids (for example, fumaric acid, maleic acid, oxalic acid and succinic acid); glucuronic acid, mandelic acid, mucic acid, nicotinic acid, orotic acid, pamoic acid, pantothenic acid; sulfonic acids (for example, benzenesulfonic acid, camphosulfonic acid, edisylic acid, ethanesulfonic acid, isethionic acid, methanesulfonic acid, naphthalenesulfonic acid, naphthalene-1,5-disulfonic acid, naphthalene-2,6-disulfonic acid and p-toluenesulfonic acid); xinafoic acid, and the like.

Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The compositions may be further distinguished by their pH. In some embodiments, the composition is in a liquid form with a pH between 2.0-8.0, between 3.0-7.0, between 4.0-6.0, between 4.0-5.0, between 4.5-5.5, between 5.0-6.0, between 5.5-6.5, between 6.0-7.0, between 6.5-7.5, between 7.0-8.0, between 7.5-8.5, between 8.0-9.0, or between any range defined by any of these pH values. In some embodiments, the composition has a pH of about 4, 5, 6, 7, 8 or 9. In some embodiments, the composition has a pH of about 5. In some embodiments, the composition has pH of about 7.4.

As used herein, the "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In a preferred embodiment, the composition is orally administered. Methods for making formulations for oral administration are found, for example, in "Remington: The Science and Practice of Pharmacy" (20th ed., ed. A. R. Gennaro, 2000, Lippincott Williams & Wilkins). Oral compositions generally include an edible carrier, an inert diluent, or both. Formulations for oral administration include e.g., tablets, pills, caplets, hard capsules, soft capsules, sachets, and liquid dosage forms, and may contain various additives and/or excipients as needed. In addition, liquid-filled capsules can include the active agent(s) of the present disclosure.

When administered in solid form, the composition may include a solid carrier. The carrier may comprise a porous excipient and optionally a binder and/or disintegrant. When the solid carrier is in the form of granules, the median particle size of the granules may range from about 5 microns to about 600 microns, for example from about 10 to about 300 microns. Granules may be compressed to form a tablet which is used as the solid carrier.

The porous excipient typically forms the bulk of the solid carrier. The porous excipient (and the solid carrier) has a porosity of, for example, greater than about 10% v/v, such as greater than about 15% v/v, greater than about 20% v/v, greater than about 30% v/v or greater than about 30% v/v. In a preferred embodiment, the porosity is greater than about 30% v/v, for example, from about 30 to about 50% v/v. In another embodiment, the porosity is up to about 97% (e.g., from about 90 to about 94%) (such as Zeopharm or Aeroperl).

The porous excipient may have a median particle size of from about 5 microns to about 600 microns, for example from about 10 to about 300 microns. In one embodiment, the porous excipient may have a particle size of from about 10 microns to about 150 microns.

The solid carrier may include the porous excipient at a concentration of about 20% w/w or more, such as about 25% w/w or more, about 30% w/w or more, about 35% w/w or more, about 40% w/w or more, about 45% w/w or more, about 50 w/w or more, about 60% w/w or more, about 70% or more, about 80% or more, about 90% or more, about 95% or more, 98% or more, or any range of percentages there between.

Exemplary porous excipients include, but are not limited to, metal oxides, metal silicates, metal carbonates, metal phosphates, metal sulfates, sugar alcohols, sugars, celluloses, cellulose derivatives, and any combination of those. In a preferred embodiment, the porous excipient is a metal silicate, e.g., a silicon dioxide, such as Zeopharm (available from J.M. Huber Corporation) or Aeroperl (available from Evonik industries). In another preferred embodiment, the porous excipient is a metal oxide, such as magnesium aluminometasilicate.

Metal oxides include as examples, but are not limited to, magnesium oxide, calcium oxide, zinc oxide, aluminum oxide, titanium dioxide (such as Tronox A-HP-328 and Tronox A-HP-100), silicon dioxides (such as Aerosil, Cab-O-Sil, Syloid, Aeroperl, Sunsil (silicon beads), Zeofree, Zeopharm, Sipernat), and mixtures thereof. In one embodiment, the metal oxide is titanium dioxide, silicon dioxide or a mixture thereof. Silicon dioxides may be subdivided into porous and nonporous silicas.

Metal silicates include as examples, but are not limited to, sodium silicate, potassium silicate, magnesium silicate, calcium silicate including synthetic calcium silicate such as, e.g., Hubersorp, zinc silicate, aluminum silicate, sodium aluminosilicate such as, e.g., Zeolex, magnesium aluminum silicate, magnesium aluminum metasilicate, aluminium metasilicate. The porous excipient may be a hydrous aluminum silicate or alkaline earth metal silicate, such as magnesium aluminum metasilicate (e.g., Neusilin available from Fuji Chemical Co.).

Suitable metal phosphates include, but are not limited to, sodium phosphate, disodium hydrogen phosphate, sodium dihydrogen phosphate, potassium phosphate, dipotassium hydrogen phosphate, potassium dihydrogen phosphate, calcium phosphate, magnesium phosphate, zinc phosphate, aluminum phosphate, and combinations thereof. For example, the porous excipient can be dibasic anhydrous calcium phosphate, dibasic dihydrate calcium phosphate, tribasic calcium phosphate, or a combination thereof.

Exemplary metal sulfates include, e.g., sodium sulfate, sodium hydrogen sulfate, potassium sulfate, potassium hydrogen sulfate, calcium sulfate, magnesium sulfate, zinc sulfate aluminum sulfate, and mixtures thereof.

Exemplary sugar alcohols include, e.g., sorbitol, xylitol, mannitol, maltitol, inositol, and/or it may be a sugar selected from the group consisting of mono-, di- or polysaccharides including saccharose, glucose, fructose, sorbose, xylose, lactose, dextran, dextran derivatives, cyclodextrins, and mixtures thereof.

Exemplary celluloses and cellulose derivatives include, e.g., cellulose, microcrystalline cellulose, cellulose derivatives including porous cellulose beads: cellulose, hydroxypropyl methylcellulose (HPMC), hydroxypropyl cellulose (HPC), methylcellulose, ethylcellulose, sodium carboxymethylcellulose, hydroxyethyl cellulose etc.

The solid oral dosage form may further comprise one or more pharmaceutically acceptable excipients. Examples of such excipients include, but are not limited to, fillers, diluents, binders, lubricants, glidants, enhancers, wetting agents, surfactants, antioxidants, metal scavengers, pH-adjusting agents, acidifying agents, alkalizing agents, preservatives, buffering agents, chelating agents, stabilizing agents, coloring agents, complexing agents, emulsifying and/or solubilizing agents, absorption enhancing agents, modify release agents, flavoring agents, taste-masking agents, humectants, and sweetening agents.

The amount of solid carrier in the solid oral dosage form may vary depending on its porosity, as the liquid formulation. Since the solid oral dosage form, such as tablet or capsule, is intended for oral ingestion by a mammal, such as a human subject, the solid oral dosage form preferably weighs from about 500 mg to about 5000 mg, such as from about 600 mg to about 2000 mg, or from about 600 mg to about 1500 mg. In one embodiment, the solid oral dosage form weighs from about 700 mg to about 1200 mg.

The solid oral dosage form (e.g., oral tablet) described herein may optionally contain one or more coatings, such as a sub-coating and/or modified release coating (e.g. an enteric coating). The sub-coating may be, e.g., Opadray AMB OY-B. The enteric coating may contain, e.g., Acryl EZE, dimethicone and triethyl citrate.

In one embodiment, the solid oral dosage form does not have a coating. In a preferred embodiment, the solid oral dosage form does not have an enteric coating. In another embodiment, the solid oral dosage form does not have a modified release coating. In certain embodiments, the solid oral dosage form provides for immediate release of the active agent(s). In other embodiments, the solid oral dosage form provides extended release of the active agent(s).

The solid oral dosage form may be in the form of a tablet. In one embodiment, the tablet is a compressed or molded tablet, e.g., having a hardness of from about 20 N to about 150 N. The hardness of the tablet can be from about 30, 40, or 50 N to about 70, 80, 90 or 100 N.

The oral tablet may include one or more excipients, such as those mentioned above including, but not limited to, flavoring agents, lubricants, binders, preservatives, and disintegrants.

In some embodiments, the active agents are adsorbed onto a nanoparticle or solid matrix (e.g., a porous silicate including alkali-metal silicates, alkaline earth metal silicates, or aluminum silicates, or including aluminum silicate, magnesium aluminum silicate, sodium silicate, potassium silicate, magnesium silicate, or calcium silicate), or any other solid matrix described herein. In certain embodiments, the active agent(s) are incorporated into or onto a nanoparticle. As used herein, the term "nanoparticle" refers to a solid particle having a structure including at least one region or characteristic dimension with a dimension of between 1-500 nm and having any suitable shape, e.g., a rectangle, a circle, a sphere, a cube, an ellipse, or other regular or irregular shape. Non-limiting examples of suitable nanoparticles may include liposomes, poloxamers, microemulsions, micelles, dendrimers and other phospholipid-containing systems, and perfluorocarbon nanoparticles. The term "nanoparticle" can include nanospheres, nanorods, nanoshells, and nanoprisms and these nanoparticles can be part of a nanonetwork. Without limitations, the nanoparticles used herein can be any nanoparticle available in the art or available to one of skill in the art.

In some embodiments, the nanoparticle is of size from about 10 nm to about 750 nm, from about 20 nm to about 500 nm, from about 25 nm to about 250 nm, or from about 50 nm to about 150 nm. In some embodiments, the nanoparticle is of size from about 5 nm to about 75 nm, from about 10 nm to about 50 nm, from about 15 nm to about 25 nm. The nanoparticles can be, e.g., monodisperse or polydisperse and the variation in diameter of the particles of a given dispersion can vary. The nanoparticles can be hollow or solid. In some embodiments, the nanoparticles have an average diameter of less than 500 nm, less than 300 nm, less than 100 nm, less than 50 nm, less than 25 nm, less than 10 nm or less than 5 nm.

Nanoparticles can be made, for example, out of metals such as iron, nickel, aluminum, gold, copper, zinc, cadmium, titanium, zirconium, tin, lead, chromium, manganese and cobalt; metal oxides and hydrated oxides such as aluminum oxide, chromium oxide, iron oxide, zinc oxide, and cobalt oxide; metal silicates such as of magnesium, aluminum, zinc, lead, chromium, copper, iron, cobalt, and nickel; alloys such as bronze, brass, stainless steel, and so forth. Nanoparticles can also be made of non-metal or organic materials such as cellulose, ceramics, glass, nylon, polystyrene, rubber, plastic, or latex. In some embodiments, nanoparticles comprise a combination of a metal and a non-metal or organic compound, for example, methacrylate- or styrene-coated metals and silicate coated metals. The base material can be doped with an agent to alter its physical or chemical properties. For example, rare earth oxides can be included in aluminosilicate glasses to create a paramagnetic glass materials with high density (see White & Day, Key Engineering Materials Vol. 94-95, 181-208, 1994). In some embodiments, nanoparticles comprise or consist of biodegradable organic materials, such as cellulose, dextran, and the like. Suitable commercially available particles include, for example, nickel particles (Type 123, VM 63, 18/209A, 10/585A, 347355 and HDNP sold by Novamet Specialty Products, Inc., Wyckoff, N.J.; 08841R sold by Spex, Inc.; 01509BW sold by Aldrich), stainless steel particles (P316L sold by Ametek), zinc dust (Aldrich), palladium particles (D13A17, John Matthey Elec.), and $TiO_2$, $SiO_2$, or $MnO_2$ particles (Aldrich).

In some embodiments, the nanoparticles are freeze-dried to form solid dried nanoparticles. The dried nanoparticles may be loaded in a capsule (such as a two-part hard gelatin capsule) for oral administration in a subject. In addition, the capsule may be further coated with an enteric coating. The freeze-dried nanoparticles can be rehydrated in solution or by contacting fluid so to revert to wet nanoparticles having positive surface charge.

In some embodiments, a liposome delivery vehicle may be utilized. Liposomes, depending upon the embodiment, are suitable for delivery of the active agents in the present disclosure in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tetradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramnethylindocarbocyanine, 3,3'-deheptyloxacarbocyanine iodide, 1,1'-dedodecyl-3,3,3',3'-tetramethylindocarbocyanine perchloarate, 1,1'-dioleyl-3,3, 3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the fatty acids of a phosphoglyceride, or cholesterol, a major component of animal cell membranes. Liposomes may optionally contain pegylated lipids, which are lipids covalently linked to polyethylene glycol (PEG) or derivatives thereof. Exemplary PEGs can have a molecular weight of 200-10,000 kDa (e.g., 400-4000 kDa, 500-1000 kDa, 750-1500 kDa, 800-1200 kDa, 900-1100 kDa, or about 1000 kDa). PEG derivatives include, for example, methylated PEG, polypropylene glycol (PPG), PEG-NHS, PEGaldehyde, PEG-SH, PEG-NH$_2$, PEG-CO$_2$H, PEG-OMe and other ethers, branched PEGs, and PEG copolymers (e.g., PEG-b-PPG-b-PEG-1100, PEG-PPG-PEG-1900, PPG-PEG-MBE-1700, and PPG-PEG-PPG-2000).

Liposomes may further comprise a suitable solvent. The solvent may be an organic solvent or an inorganic solvent. Suitable solvents include, but are not limited to, di methyl-sulfoxide (DMSO), methylpyrrolidone, N-methylpyrrolidone, acetronitrile, alcohols, dimethylformamide, tetrahydrofuran, or combinations thereof.

Liposomes may be prepared by any known method of preparing liposomes for drug delivery, such as, for example, detailed in e.g., U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618. For example, liposomes may be prepared by sonicating lipids in an aqueous solution, solvent injection, lipid hydration, reverse evaporation, or freeze drying by repeated freezing and thawing. In certain preferred embodiments the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, the composition is delivered to a tissue or cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear, but also may appear as a milky colloidal suspension depending on exact composition, storage conditions, pH, temperature, surface charge, shape, and such. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions may optimally comprise phospholipids, although other hydrophobic core components singularly or in mixtures (e.g., perfluorocarbons: see below) may contribute to the composition of the particle. Any of the phospholipids detailed above for liposomes are suitable for embodiments directed to microemulsions. The composition of the invention may be encapsulated in a microemulsion by any method generally known in the art.

In yet another embodiment, the composition may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate or conjugate the active agents of the present disclosure via standard linker chemistries known in the art. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

In certain embodiments, the nanoparticle is a perfluorocarbon nanoparticle. Such nanoparticles are known in the art. For instance, see e.g., U.S. Pat. Nos. 5,690,907; 5,780,010; 5,989,520 and 5,958,371. Exemplary perfluorocarbon emulsions are disclosed in e.g., U.S. Pat. Nos. 4,927,623; 5,077,036; 5,114,703; 5,171,755; 5,304,325; 5,350,571; 5,393,524 and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether. In some embodiments, the perfluorocarbon compound is perfluoro-n-octyl bromide. In other embodiments, the perfluorocarbon compound may be a perfluoroalkylated crown ether.

In some embodiments, the nanoparticle comprises on its surface a biocompatible layer or material. As used herein, the term "biocompatible layer or material" refers to any material or layer that does not deteriorate appreciably and does not induce a significant adverse effect, e.g., toxic reaction, over time when placed adjacent to the biological tissue of a subject, or induce blood clotting or coagulation when it comes in contact with blood. Suitable biocompatible materials can include, but are not limited to, polymers comprising an amino group (e.g., carbohydrate-based amino-polymers, protein-based amino-polymers, or molecules comprising at least one amino group), silk fibroin, derivatives and copolymers of polyimides, polyvinyl alcohol, polyethyleneimine, polyvinylamine, polyacrylates, polyamides, polyesters, polycarbonates, polydimethylsiloxane, polyimide, polyethylene terephthalate, polymethylmethacrylate, polyurethane, polyvinylchloride, polystyrene, polysulfone, polycarbonate, polymethylpentene, polypropylene, a polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ketones), poly(ethylene glycol), styrene-acrylonitrile resin, poly(trimethylene terephthalate), polyvinyl butyral, polyvinylidenedifluoride, poly(vinyl pyrrolidone), polyethylene glycol, natural or synthetic phospholipids, fatty acids, cholesterols, lysolipids, sphingomyelins, and the like, including lipid conjugated polyethylene glycol. Various commercial anionic, cationic, and non-ionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids, including DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethyl-ammonio)butanoyl-sn-glycerol,1,2-diacyl-3-trimethylammonium-propane; 1,2-diacyl-3-dimethylammonium-propane; 1,2-diacyl-sn-glycerol-3-ethyl phosphocholine; and 3.beta.-[N',N'-dimethylaminoethane)-carbamol]cholesterol-HCl, may also be used and any combinations thereof.

In certain preferred embodiments, a nanoparticle can comprise on its surface a biocompatible layer to prolong the circulation time of the nanoparticles in a subject, such as polyethylene gycol (PEG). In some embodiments, the biocompatible layer can be selected to induce antigen-specific immunity in a subject. In other embodiments, the biocompatible layer can be selected to reduce or minimize the exposure of the nanoparticle material to surrounding tissue in a subject.

Exemplary nanoparticle compositions for use in the present methods are described in U.S. Patent Publication Application Nos. 2007/0154559, 2010/0104645 and 2015/0150822.

The pharmaceutical compositions of the present disclosure may further include one or more absorption enhancers to enhance the efficiency of transport through the intestinal mucosa into the blood. In one embodiment, the absorption enhancer includes an oil coating that constitutes a physical barrier providing additional protection against digestive enzymes. Secretion of bile acids typically causes dispersion of the oil suspension into smaller particles, which can be absorbed in the small intestine. While the particle size is reduced after traversing the stomach and entering the small intestine, the particles remain in a size range of 30-1000 nm, too large to be a substrate for lipases and peptidases, preserving the protective effect of the composition. Advantageously, lipid-coating particles of this size are absorbed to chylomicrons by lacteal vessels, which are lymphatic vessels originating in the villi of the small intestine. Particles absorbed in this manner can reach the bloodstream without undergoing first-pass metabolism.

In other embodiments, the absorption enhancer(s) include one or more bile salts, anionic surfactants, medium-chain fatty acids, phosphate esters and sodium N-[8-(2-hydroxybenzoyl)amino]caprylate.

In other embodiments, oral availability of the active agent(s) may be enhanced by including an include an acyl carnitine (e.g., palmitoyl carnitine), optionally in combination with an alcohol, a polysorbate surfactant, a carboxylic acid, an alcohol, a polyethylene glycol, a polyglycolized glyceride, alkyl saccharides, ester saccharides, a TPGS compound, or a sugar, as described in U.S. Patent Publication Application No. 2016/0074322.

In some embodiments, the composition may be further coated, conjugated to or modified with a tumor-specific or cell/tissue specific targeting agent for selective targeting of cancer cells. The targeting agent may be a small molecule (e.g., folate, adenosine, purine, lysine), peptide, ligand, antibody fragment, aptamer or synbody. Such compositions may allow for the use of a lower dose of cytotoxic drugs, reduce adverse events, increase efficacy, and reduce the possibility of the drugs being rapidly cleared from targeted tumors or cancer cells. Targeted compositions according to the present application allow for active agents to be taken up by cancer cells so as to effectively deliver the active agents to intracellular targets in the cancer cells to promote apoptosis and limit the potential of chemoresistance and systemic toxicities.

In some embodiments, the cell targeting agent is directed to tumor associated antigen, preferably a cell surface antigen. Examples of tumor associated antigens include, but are not limited to, adenosine receptors, alpha v beta 3, aminopeptidase P, alpha-fetoprotein, cancer antigen 125, carcinoembryonic antigen, cCaveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, and tyrosine kinases. In certain preferred embodiments, the cell targeting agent is folate or a folate derivative that binds specifically to folate receptors (FRs).

The reduced folate carrier (RFC) system is a low-affinity, high capacity system that mediates the uptake of reduced folates into cancer cells at pharmacologic (M) concentrations. The concentration of physiologic folates is in the range of 5 to 50 nM. Therefore, high affinity human FRs exist and are encoded by a family of genes whose homologous products are termed FR type $\alpha$, $\beta$, $\gamma$, or $\delta$, which are also described as FR1, FR2, FR3, or FR4, respectively. The membrane isoforms FR1, FR2, and FR4 can bind and transport folate or folate derivatives into the cell, while FR3 lacks a membrane anchor and is secreted from the cell. FR1 and FR2 bind folate and 6S 5-formyltetrahydrofolate (i.e., leucovorin) with similar yet different affinities 1.5 nM versus 0.35 nM (folate) and 800 nM versus 7 nM (leucovorin), respectively. 6S 5-methyltetrahydrofolate is the predominate folate in the blood and has similar affinities for FR1 and FR2, 55 nM and 1 nM, respectively. While PC3 human prostate cancer cells do not significantly express FR (e.g., FR1) in culture, FRs are expressed by PC3 tumors. FRs are also expressed by BrCa cells are associated with poor outcomes or transport folate via these receptors despite resistance to methotrexate.

Most nonproliferative tissues lack functional FR expression. FR expression in proliferating normal tissues is restricted to the luminal surface of certain epithelial cells and thus inaccessible to the circulation. However, the presence of high levels of FR2 (high affinity receptor) on malignant tumors and leukemias are exposed to circulation making them an attractive candidate for tumor-specific therapeutics. The kidney, where FR1 (moderate affinity receptor) is expressed in the proximal tubules, is protected from FR-targeted therapies that are excluded from glomerular filtration. Further protection is a result of the renal folate conservation mechanism where after FR-mediated endocytosis by renal tubular cells there is rapid dissociation of the folate and transport across the basolateral membranes into the blood.

In certain compositions, especially those for non-oral delivery, the targeting agent may be an antibody or peptide capable of binding tumor associated antigens consisting of put not limited to: adenosine receptors, alpha v beta 3, aminopeptidase P, alpha-fetoprotein, cancer antigen 125, carcinoembryonic antigen, caveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, tyrosine kinases, etc.

In certain embodiments, the pharmaceutical composition is orally administered as non-toxic anticancer formulation comprising monoethanolamine (Etn), an Etn prodrug, an Etn hybrid molecule, or a combination thereof. In some embodiments, the pharmaceutical composition is orally administered as non-toxic anticancer formulation comprising monoethanolamine (Etn) and phosphoethanolamine (PhosE).

As used herein, the term "cancer" refers to any of the various malignant neoplasms characterized by the proliferation of cells that have the capability to invade surrounding tissue and/or metastasize to new colonization sites, including but not limited to leukemias, lymphomas, carcinomas, melanomas, sarcomas, germ cell tumors and blastomas. Exemplary cancers include cancers of the brain, bladder, breast, cervix, colon, head and neck, kidney, lung, non-small cell lung, mesothelioma, ovary, prostate, stomach and uterus, leukemia and medulloblastoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "leukemia" refers to broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which arises from transformed cells of mesenchymal origin. Sarcomas are malignant tumors of the connective tissue and are generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Neoplastic tissues treatable by the compositions described herein can originate from any cell type or tissue found in a mammal, including, but not limited to hepatic, skin, breast, prostate, neural, optic, intestinal, cardiac, vasculature, lymph, spleen, renal, bladder, lung, muscle, connective, tissue, pancreatic, pituitary, endocrine, reproductive organs, bone, and blood. The neoplastic tissue for analysis may include any type of solid tumor or hematological cancer.

In certain embodiments, the subject has a cancer selected from the group consisting of prostate, breast, lung, kidney, liver, ovarian, pancreatic and gastrointestinal. In a preferred embodiment, the subject has prostate cancer.

As used herein, the term "pharmaceutically acceptable carrier" include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin. In some embodiments, the pharmaceutical composition of the present application comprises Etn, a phosphate salt, salts, and a pharmaceutically acceptable carrier.

The pharmaceutical composition is formulated to be compatible with its intended route of administration. The compounds may be administered to the patient with known methods, such as oral administration, intravenous administration as a bolus or by continuous infusion over a period of time, by intramuscular, intraperitoneal, intracerebrospinal, subcutaneous, intra-articular, intrasynovial, intrathecal, topical, transmucosal and/or inhalation routes. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

In certain embodiments, compositions for oral delivery may include one or more structural elements promoting adherence to the intestinal mucosa after oral administration, thereby significantly increasing the time of intestinal transit of the formulation. In some embodiments, the composition is formulated as a solid or semi-solid formulation in capsules.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Therapeutic efficacy and toxicity of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. In certain embodiments, single dosage contains 0.01 ug to 50 mg of the active compound.

As a general proposition, the therapeutically effective amount of the active compound will be in the range of about 1 ng/kg body weight/day to about 100 mg/kg body weight/day whether by one or more administrations. In a particular embodiments, the active compound is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In certain embodiments, the active compound is administered at a dose of 500 µg to 20 g every three days, or 10 µg to 400 mg/kg body weight every three days. In other embodiments, the active compound is administered in the range of about 10 ng to about 100 ng per individual administration, about 10 ng to about 1 µg per individual administration, about 10 ng to about 10 µg per individual administration, about 10 ng to about 100 µg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The therapeutic agent(s) may be administered daily, or every 2, 3, 4, 5, 6 or 7 days, or every 1, 2, 3 or 4 weeks.

In other particular embodiments, the active compound is administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage(s) will be dependent on the condition, size, age and condition of the patient.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

EXAMPLES

Example 1. Screening of PE Lipid Precursors as Anticancer Candidates

The development of oral drugs for cancer treatment is impeded by toxicity, limited solubility, poor GI-tract stability, low permeability and extensive first-pass metabolism and poor bioavailability. Therefore, it was of interest to evaluate the prospects of PE lipid precursors as chemotherapeutic candidates for oral delivery. Interestingly, Etn and PhosE both satisfy Lipinski's rule of five and Veber's rule that examine the molecular properties and drug likeness, respectively, of a compound, suggesting that these PE lipid precursors (FIG. 1) can induce pharmacological effects in humans upon oral consumption, thus qualifying them as viable candidates for further evaluation.

Figure 2:
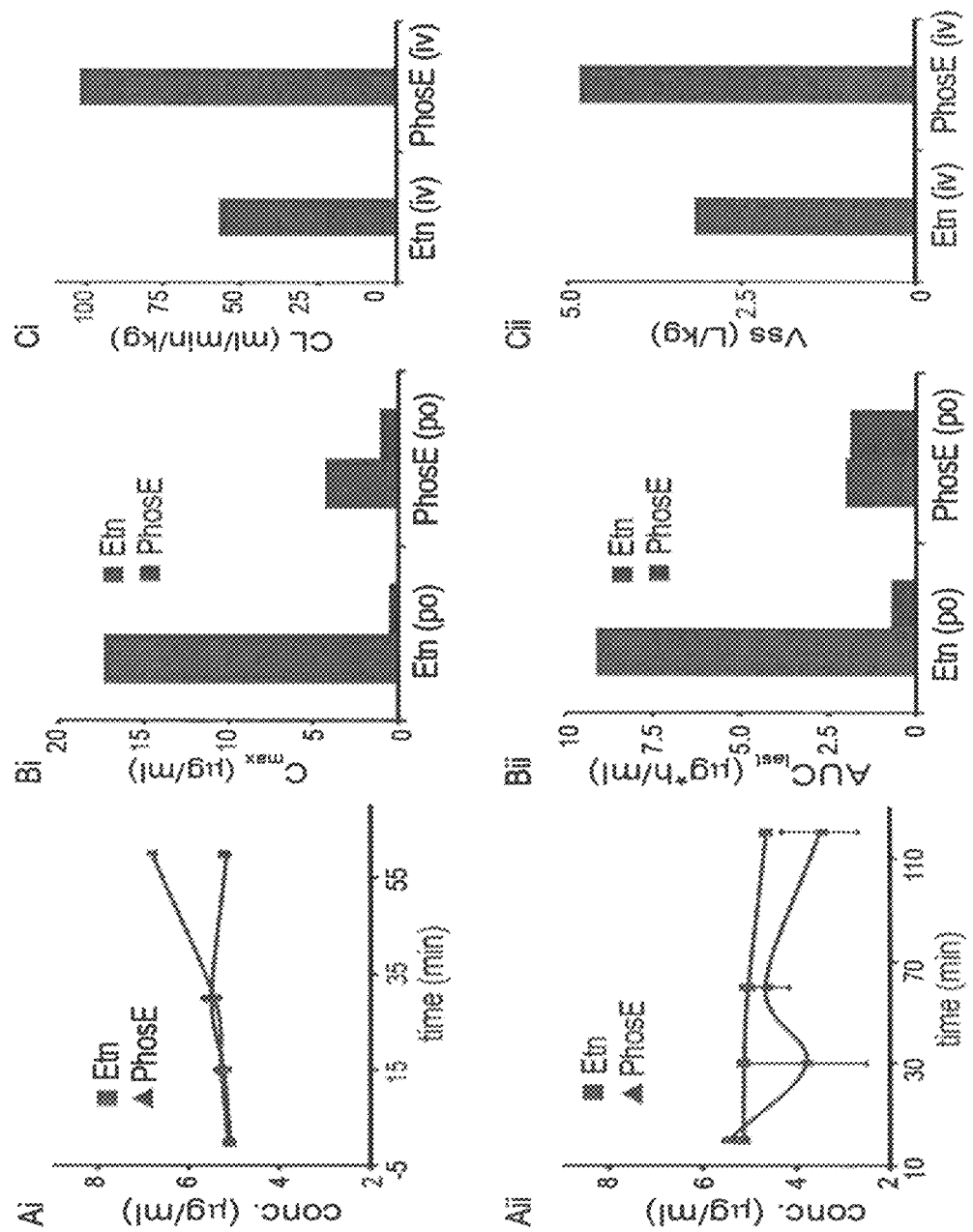
FIG. 2 shows gastrointestinal stability and pharmacokinetic parameters of Etn and PhosE. Stability of Etn and PhosE in (Panel Ai) SGF (pH 1.2) and (Panel Aii) SIF (pH 6.8). Etn (10 µM) and PhosE (10 µM) were spiked into pre-incubated SGF and SIF. Samples (100 µl) were drawn at 0, 15, 30 and 60 min from SGF reaction-vials and at 0, 30, 60 and 120 min from SIF reaction-vials, quenched with acetonitrile, vortex-mixed, and centrifuged before supernatant analysis by LC-MS/MS analysis. (Panel Bi) $C_{max}$ and (Panel Bii) $AUC_{last}$ for Etn and PhosE upon oral administration of Etn and PhosE. (Ci) CL (clearance) and (Cii) Vss (volume of distribution) for Etn and PhosE upon intravenous administration of Etn and PhosE. While PhosE and Etn were orally-fed at 60 mg/kg and 40 mg/kg, respectively, intravenous administration was at 3 mg/kg and 2 mg/kg, respectively. For PK studies, a sparse sampling design with 3 mice per time point was used to collect blood samples at 5, 10, 15, 30 min and 1, 2, 3, 4, 5 and 6 h in $K_2$EDTA-coated tubes. The pharmacokinetic parameters ($AUC_{last}$, $C_{max}$, CL and Vss) were calculated using non-compartmental analysis tool of Phoenix WinNonlin software (version 6.3).

Given the extreme pH and various digestive enzymes, the GI tract presents a harsh environment to any ingested xenobiotic. Thus, many potential drug candidates are degraded in the GI tract, explaining their decreased bioavailability or inability to reach the target at effective concentrations. Simulated gastric fluid (SGF; pH 1.2) and simulated intestinal fluid (SIF; pH 6.8) closely mimic the GI tract environment and are amenable in vitro systems to evaluate degradation of a compound in GI tract (US Pharmacopoia). Etn and PhosE were stable in SGF over 1 h (FIG. 2, panel Ai). While Etn remained unchanged in SIF over time (FIG. 2, panel Aii), PhosE exhibited a ~35% decrease in its concentration after 2 h in SIF suggesting its degradation (FIG. 2, panel Aii). These results demonstrate enhanced stability of Etn compared to PhosE in the GI-tract.

Example 2. Drug-Drug Interactions and Pharmacokinetics of PE Lipid Precursors

During polypharmacy, drug-drug interaction (DDIs) are one of the major causes of toxicity and has led to drug marketing with black box warnings (Caterina Palleria et al., J. Res. Med. Chem. 2013; 18:601-10). Thus, the potential of Etn and PhosE to inhibit major drug metabolizing CYP enzymes was evaluated. Among all the nine tested CYPs (CYP1 A2, CYP2A6, CYP2B6, CYP2C8, CYP2C9, CYP2C19, CYP2D6, CYP2E1 and CYP3A4) Etn and PhosE showed $IC_{50}$ values of more than 100 µM (equivalent to 6.1 µg/ml Etn and 14.1 µg/ml PhosE), consistent with no CYP related drug-drug interaction liabilities (Table 3).

TABLE 3

CYP inhibition $IC_{50}$ values for Etn and PhosE in human liver microsomes

| CYP isoform | Etn $IC_{50}$ (µM) | PhosE $IC_{50}$ (µM) |
| --- | --- | --- |
| 1A2 | >100 | >100 |
| 2A6 | >100 | >100 |
| 2B6 | >100 | >100 |
| 2C8 | >100 | >100 |
| 2C9 | >100 | >100 |
| 2C19 | >100 | >100 |
| 2D6 | >100 | >100 |
| 2E1 | >100 | >100 |
| 3A4-mida | >100 | >100 |
| 3A4-testo | >100 | >100 |

Figure 3:
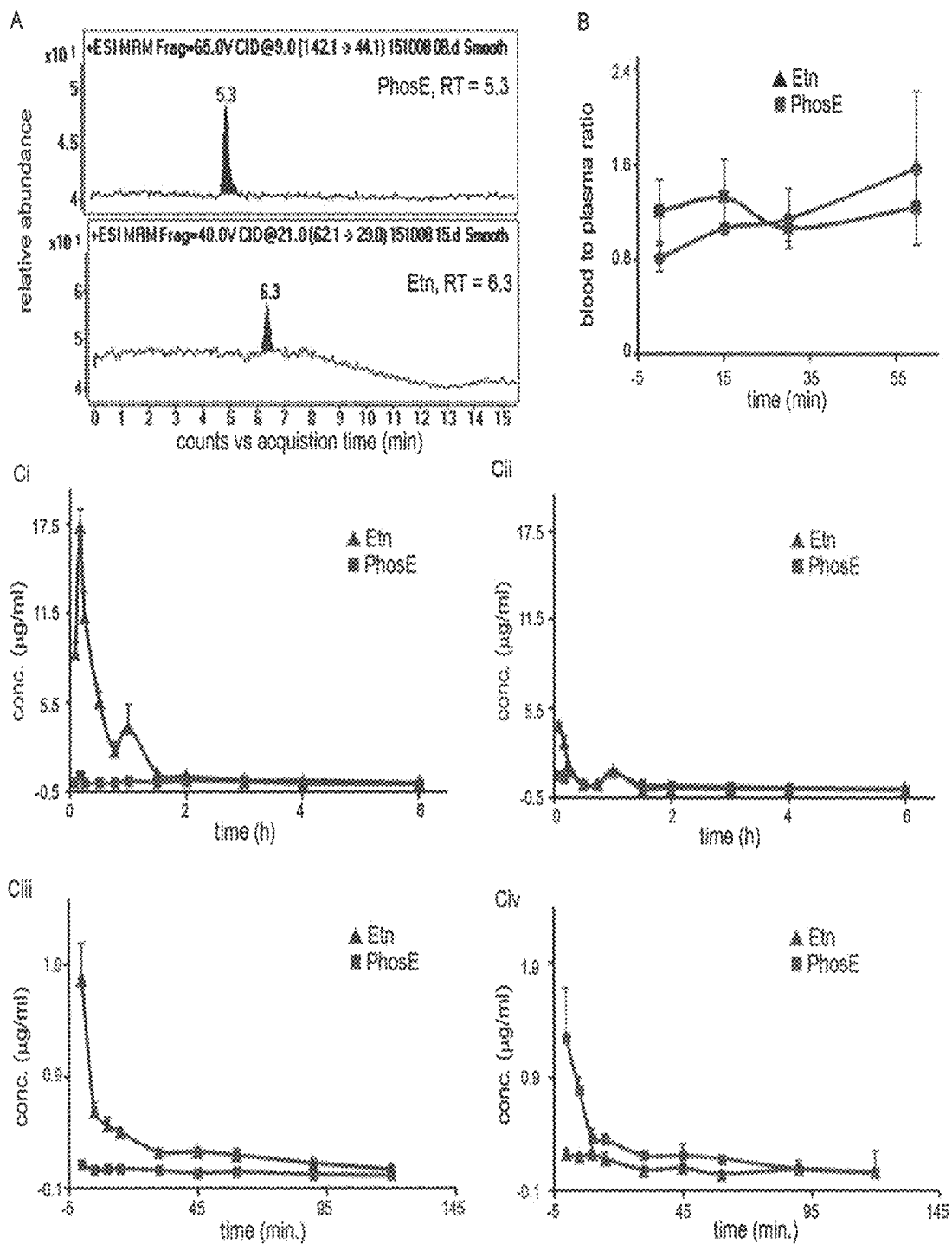
FIG. 3 shows PK profiles and distribution of Etn and PhosE into blood and plasma (Panel A). Representative chromatograms for Etn and PhosE showing relative abundance of Etn and PhosE product ions used for their quantification. (Panel B) Blood to plasma ratio (BPR) of Etn and PhosE. BPR for both PhosE and Etn was lower than 1.5 indicating that these compounds do not accumulate in RBCs preferentially. Etn and PhosE were quantified employing LC-MS/MS with electrospray ionization in positive-ion mode. Pharmacokinetic profiles of Etn and PhosE upon oral (Ci, Cii) and intravenous (Ciii, Civ) administration of Etn (Ci, Ciii) and PhosE (Cii, Civ). For these PK studies, the doses of lipid precursors administered orally were 40 mg/kg Etn and 60 mg/kg PhosE, and intravenously were 2 mg/kg Etn and 3 mg/kg PhosE. Values and error bars shown in the figure represent mean and SE, respectively.
Figure 4:
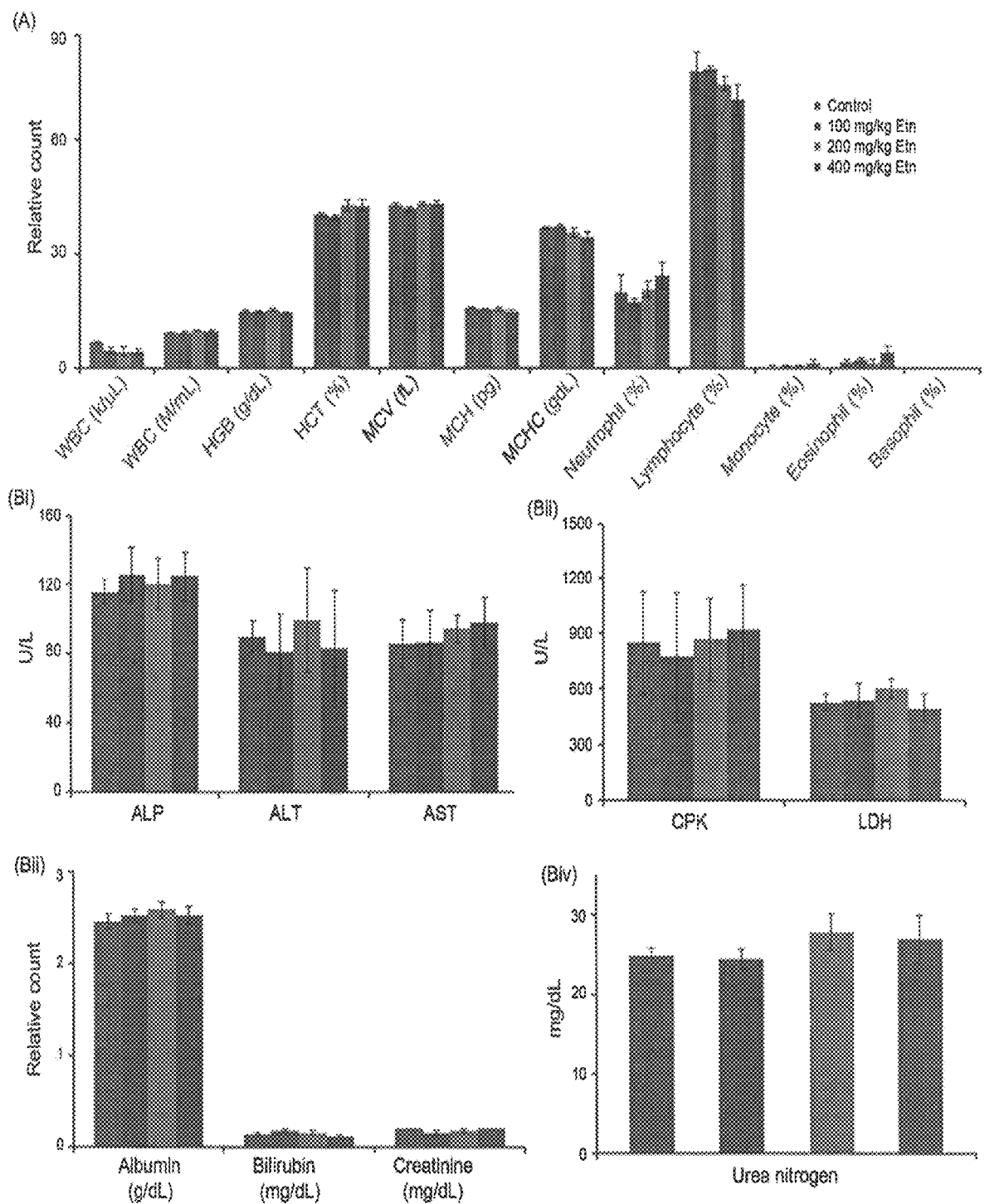
FIG. 4 shows that administration of Etn in BALB/C mice at different doses (100, 200 and 400 mg/kg) did not lead to organ-associated toxicities. (Panel A) Relative values of white blood cells (WBC), red blood cells (RBC), hemoglobin (HGB), hematocrit (HCT), mean corpuscular volume (MCV), mean corpuscular hemoglobin (MCH), mean corpuscular hemoglobin concentration (MCHC), neutrophils, lymphocytes, monocytes, eosinophils, basophils are shown for control and Etn treated groups. Levels of (Panel Bi) biomarkers of liver, alkaline phosphatase (ALP), alanine aminotransferase (ALT) and aspartate aminotransferase (AST) (Panel Bii) creatinine phosphokinase (CPK), lactate dehydrogenase (LDH) (Panel Biii) albumin, total bilirubin, creatinine, (Panel Biv) blood urea nitrogen in serum for control and Etn treated animals. Values and error bars shown in the graphs represent mean and SE, respectively.
Figure 5:
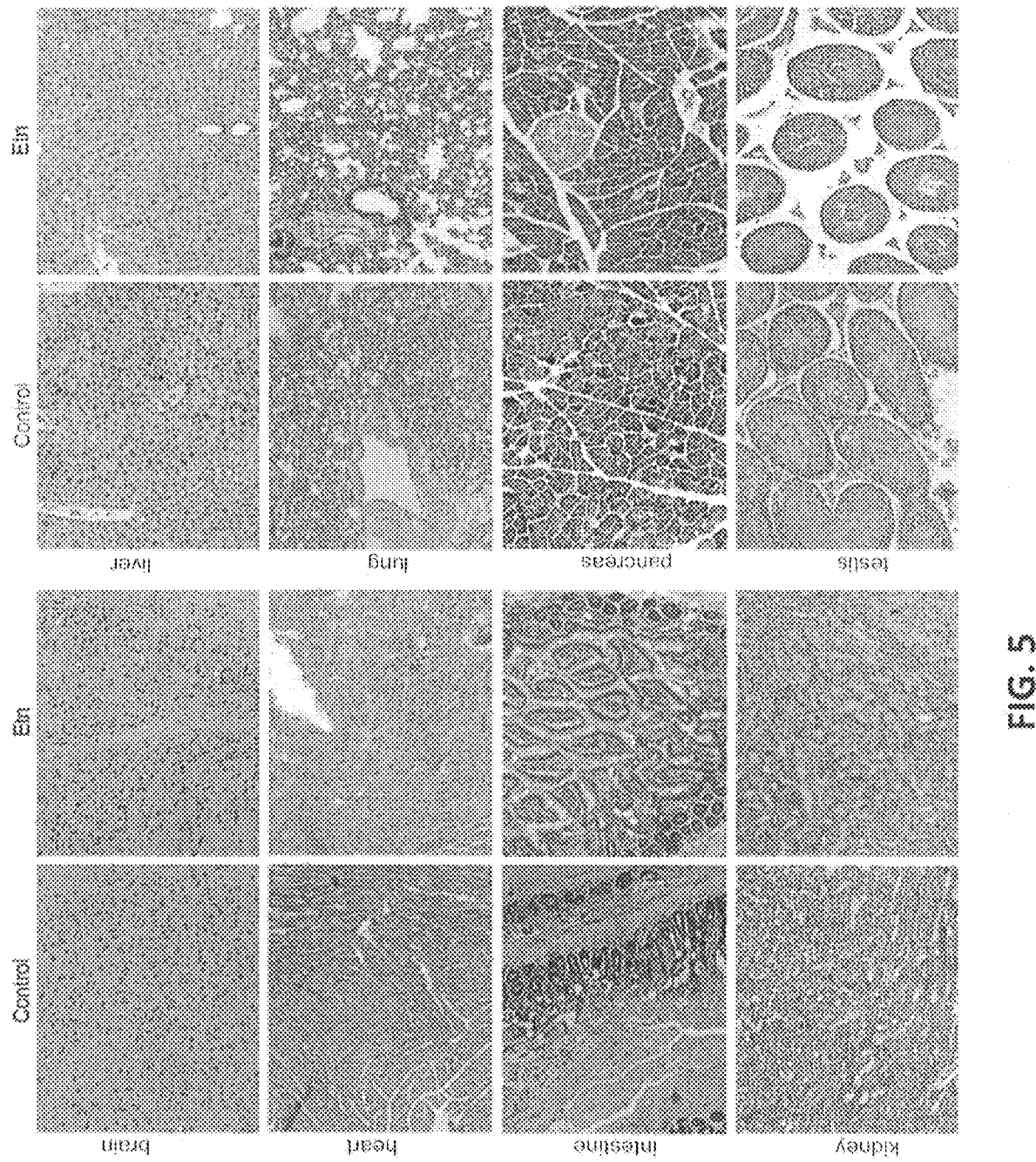
FIGS. 5 and 6 show that the daily dose of Etn did not show any organ-associated toxicity. The panels in FIG. 5 show paraffin embedded 5 µm thick tissue sections of brain, heart, intestine, kidney, liver, lung, pancreas and testis collected from control and 40 mg/kg Etn fed mice for 4 weeks. The sections were stained with hematoxylin and eosin and were observed with a 10× objective. No visible differences were observed in structural organization of these tissues from control and Etn treated mice. The panels in FIG. 6 (Panels Ai, Aii) show relative values of white blood cells (WBC), red blood cells (RBC), hemoglobin (HGB), hematocrit (HCT), mean corpuscular volume (MCV), mean corpuscular hemoglobin (MCH), mean corpuscular hemoglobin concentration (MCHC), neutrophils, lymphocytes, monocytes, eosinophils, basophils and levels of (Panels Bi, Bv) biomarkers of liver, alkaline phosphatase (ALP), alanine aminotransferase (ALT) and aspartate aminotransferase (AST), (Bii, Bvi) creatinine phosphokinase (CPK), lactate dehydrogenase (LDH), (Panels Aiii, Avii) albumin, total bilirubin, creatinine and (Biv, Bviii) blood urea nitrogen were comparable for control and 40 mg/kg Etn treated groups after two (Panel Ai, Panels Bi-iv) and four (Panels Aii, Bv-viii) weeks. Values and error bars shown in the graphs represent mean and SE, respectively.
Figure 6:
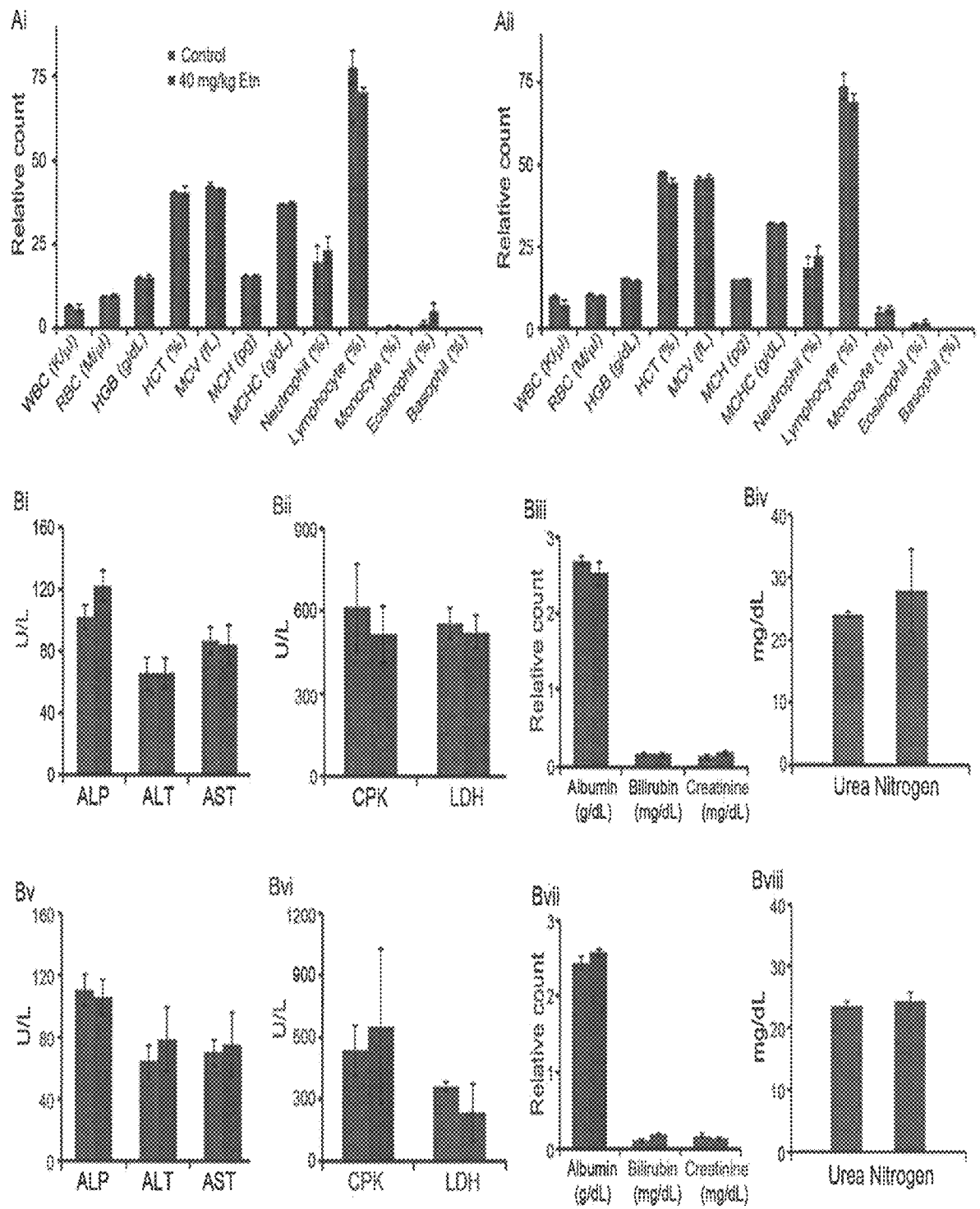
Figure 7:
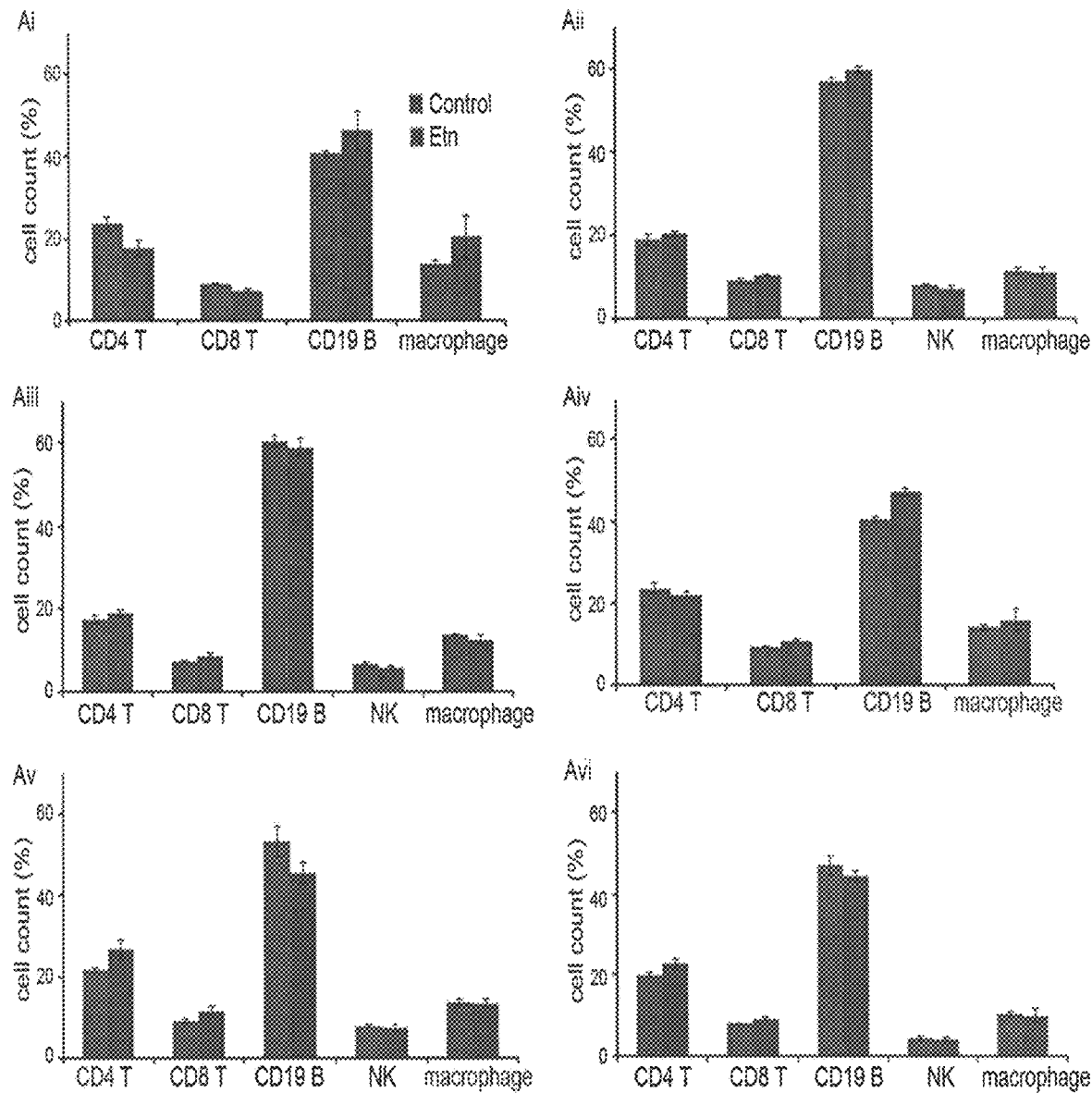
FIG. 7 shows that the daily dosing of Etn does not induce immunotoxicities. Percentages of various immune cells such as CD4 T, CD8 T, CD19B, NK cells and macrophages at time points (Panel Ai) 24 h, (Panel Aii) 48 h, (Panel Aii) 1 week, (Panel Aiv) 2 weeks, (Panel Av) 3 weeks and (Panel Avi) 4 weeks were comparable between control and 40 mg/kg Etn treated groups. Values and error bars shown in the graphs represent mean and SE respectively, from at least three animals.

3A4-mida: reaction in the presence of CYP3A4 substrate midazolam
3A4-testo: reaction in the presence of CYP3A4 substrate testosterone Next, a bioanalytical method was developed to quantify Etn and PhosE using LC-MS analysis. Representative chromatograms for Etn (RT: 6.3 min) and PhosE (RT: 5.3 min) are depicted in FIG. 3, top and bottom panels in A. To select a suitable matrix for pharmacokinetic (PK) studies and to rule out any red blood cell (RBC) accumulation of Etn and PhosE, the blood to plasma concentration ratios (BPR) were determined. These results confirmed lack of preferential partitioning into RBCs; hence plasma was selected as a suitable matrix for conducting PK studies (FIG. 3, panel B).

To evaluate bioavailability, pharmacokinetic (PK) studies in BALB/c mice were performed following oral (Etn: 40 mg/kg; PhosE: 60 mg/kg) and intravenous (Etn: 2 mg/kg; PhosE: 3 mg/kg) dose administration. Representative PK profiles of Etn and PhosE upon oral and intravenous administration of Etn and PhosE are shown in FIG. 3. The results showed that the time to reach peak plasma concentration was 10 min for both Etn and PhosE upon oral Etn administration. Maximum concentration ($C_{max}$) achieved following oral administration of 40 mg/kg Etn was 32-fold higher at 17.37 µg/mL compared to 0.55 µ/mL of PhosE. Similarly, $AUC_{last}$ of Etn was 13-fold higher at 9.10 µg*h/mL compared to 0.72 µg*h/mL of PhosE (FIG. 2, panels Bi and Bii; Table 4). However, oral administration of PhosE gave a similar exposure ($C_{max}$ and $AUC_{last}$) for both PhosE (1.14 µg/mL and 1.89 µg*h/mL) and Etn (4.32 µg/mL and 2.02 µg*h/mL), suggesting that PhosE gets converted into Etn in vivo (FIG. 2, panels Bi and Bii). A similar trend was observed following intravenous administration of PhosE (Table 4). Intravenous Etn administration led to moderate clearance at 57.23 mL/min/kg compared to normal liver blood flow of 90 mL/min/kg (FIG. 2, panel Ci). The volume of distribution of Etn was 4-fold higher compared to normal body water of 0.7 L/kg, thereby confirming its extensive distribution into various tissues (FIG. 2, panel Cii). PhosE showed high clearance of 101.92 mL/min/kg equivalent to normal liver blood flow following intravenous dose administration with a high volume of distribution at 4.82 L/kg (FIG. 2, panels Ci and 2Cii). Both Etn and PhosE showed a plasma half-life of less than 1 h. While oral bioavailability of Etn was excellent at 78%, PhosE was poorly-bioavailable at 19% (Table 4). It appears that the low oral bioavailability of PhosE may be due to its conversion to Etn by alkaline phosphatases present in the intestine and liver. Taken together, the PK data strongly suggest Etn's superiority over PhosE for an orally-deliverable agent.

TABLE 4

Comparison of pharmacokinetic parameters of Etn and PhosE following single oral and intravenous dose administration in C57BL/6J Mice (n = 3 per time point)

| Compound (mg/kg)/Route | Analyte | Pharmacokinetic Parameters | | | | | | | |
|---|---|---|---|---|---|---|---|---|---|
| | | $T_{max}$ (h) | $C_{max}/C_0$ (μg/mL) | $AUC_{last}$ (μg * h/mL) | $T_{1/2}$ (h) | $MRT_{last}$ (h) | CL (mL/min/kg) | Vss (L/kg) | F (%) |
| Etn 2/iv | Etn | — | 1.77 | 0.58 | 0.70 | 0.92 | 57.23 | 3.17 | — |
| | PhosE | — | 0.11 | 0.12 | — | — | — | — | — |
| PhosE 3/iv | Etn | — | 0.23 | 0.34 | — | — | — | — | — |
| | PhosE | — | 1.25 | 0.49 | 0.57 | 0.79 | 101.92 | 4.82 | — |
| Etn 40/po | Etn | 0.17 | 17.37 | 9.10 | — | — | — | — | 78 |
| | PhosE | 0.17 | 0.55 | 0.72 | — | — | — | — | — |
| PhosE 60/po | Etn | 0.08 | 4.32 | 2.02 | — | — | — | — | — |
| | PhosE | 1.00 | 1.14 | 1.89 | — | — | — | — | 19 |

The pharmacokinetic parameters were calculated using non-compartmental analysis tool of Phoenix WinNonlin software (version 6.3). The area under concentration time curve ($AUC_{last}$ and $AUC_{inf}$) was calculated by linear trapezoidal rule. Following oral administration, peak concentration ($C_{max}$) and time for peak concentration ($T_{max}$) were observed. Clearance and volume of distribution ($V_{ss}$) were estimated following intravenous injection. The elimination rate constant value (k) was obtained by linear regression of log-linear terminal phase of concentration-time profile using at least three declining concentrations in terminal phase with a correlation coefficient of >0.8. The terminal half-life value ($T_{1/2}$) was calculated using the equation ln2/k. Oral bioavailability was calculated by taking the ratio of dose normalized AUClast following oral to intravenous administration.
$T_{1/2}$: half-life;
$T_{max}$: time to reach peak plasma concentration;
$C_{max}$: peak plasma concentration;
$AUC_{last}$: area under the curve;
$MRT_{last}$: mean residence time;
CL: Clearance rate;
Vss: Volume of distribution;
F: Fraction absorbed To evaluate the concentration-time profile of Etn and understand its accumulation following repeated oral dosing for 28 days, Phoenix WinNonlin software was used to evaluate the single dose administration data. Simulated data of Etn showed $T_{max}$ of less than 30 min following daily repeated dose confirming rapid absorption (Table 5). No Etn accumulation was predicted on dosing over 28 days. Interestingly, a dose proportional increase in exposure was observed from 40 mg/kg to 200 mg/kg. A two-fold increase in dose (40 mg/kg to 80 mg/kg) elicited a two-fold increase in exposure. Similarly, a five-fold increase (from 40 mg/kg to 200 mg/kg) led to a five-fold increase in exposure on day 1 and day 28. The simulated data profile suggests BID (twice-a-day) dosing regimen for toxicological studies.

TABLE 5

Comparison of Day 1 and Day 28 toxicokinetic constants of Etn at 40, 80 and 200 mg/kg

| Etn (mg/kg) | Day 1 | | | | Day 28 | | | |
|---|---|---|---|---|---|---|---|---|
| | $T_{max}$ (h) | $C_{max}$ (ng/mL) | $AUC_{last}$ (ng · h/mL) | Dose normalized AUC ratio | $T_{max}$ (h) | $C_{max}$ (ng/mL) | $AUC_{last}$ (ng · h/mL) | Dose normalized AUC ratio) |
| 40 | 0.250 | 27101 | 28503 | — | 0.148 | 16610 | 27352 | — |
| 80 | 0.167 | 61369 | 59241 | 2.08 | 0.148 | 56106 | 55985 | 2.05 |
| 200 | 0.167 | 112495 | 138149 | 4.85 | 0.148 | 79388 | 137320 | 5.02 |

$C_{max}$: Maximum plasma concentration;
$AUC_{last}$: Area under the concentration-time curve;
$T_{max}$: Time to reach peak plasma concentration To examine whether Etn is non-toxic, well-tolerated and safe for oral consumption, acute toxicity of Etn in male and female Sprague-Dawley (SD) rats was tested in accordance with FDA guidelines. Five male and five female rats were orally administered a single dose of 5 g/kg Etn and monitored for one week for any sign of distress/sickness. After one week, all rats were alive and did not display any sign of distress or toxicity, thereby indicating that Etn does not induce any acute toxicity even at the limit dose. Organ-related toxicities associated with Etn feeding were further evaluated by histopathological examination of organs obtained from control and Etn-fed animals and by comparative analysis of various blood components and serum chemistry parameters indicative of liver, kidney and cardiac function and muscle integrity in control and Etn-fed groups. Immunotoxicities associated with Etn feeding were evaluated by estimating percentages of CD4-T, CD8-T, CD19-B, NK cells and macrophages in spleens obtained from control and Etn-fed animals. The resulting data show that Etn feeding did not induce any organ-related or immune toxicities and was safe for oral consumption over an extended period (FIGS. 4-7).

Example 3. Anti-Proliferative Activity of PE Lipid Precursors

Figure 8:
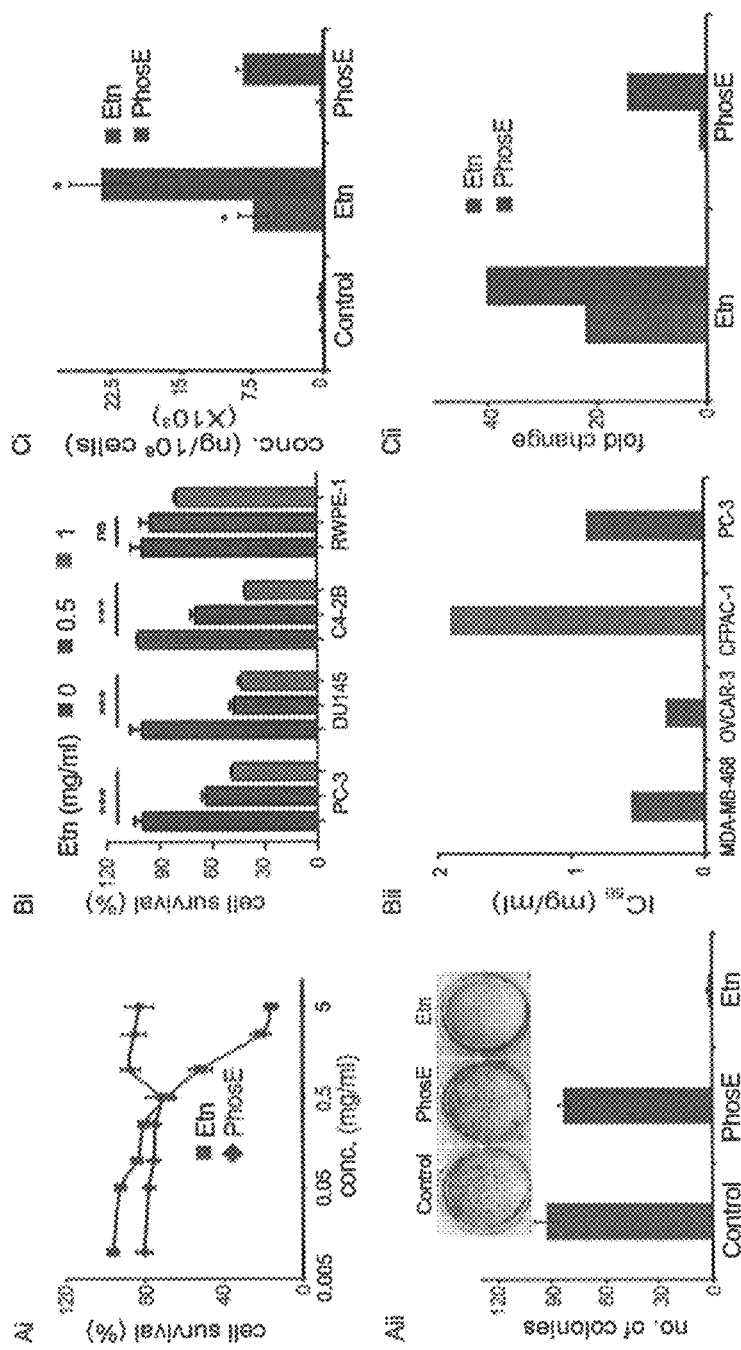
FIG. 8 shows an evaluation of in vitro anticancer efficacy and intracellular levels of PhosE and Etn. (Panel Ai) Representative dose response curve for Etn and PhosE on the proliferation of PC-3 cells. The percentage of cell survival was measured by MTT assay after treating cells with increasing concentrations of Etn and PhosE for 48 h at pH 7.4. (Panel Aii) Bar graph representation and photograph of crystal violet-stained surviving colonies from the control, Etn and PhosE-treated groups. For clonogenic survival assay, PC-3 cells treated with 2 mg/ml Etn/PhosE at pH 7.4. (Panel Bi) Antiproliferative effect of Etn treatment on prostate cancer cell lines (PC-3, DU145 and C42B) and normal cell line (RWPE-1). PC-3, DU145, C42B and RWPE-1 cells were treated with 0.5 and 1 mg/ml Etn for 48 h at pH 7.4 followed by measurement of cell survival by MIT assay. (Panel Bii) $IC_{50}$ values of Etn treatment of cancer cell lines MDA-MB-486, OVCAR-3, CFPAC-1 and PC-3. (Panel Ci) Intracellular levels of Etn and PhosE upon treatment of PC-3 cells with 1 mg/ml Etn and PhosE. PC-3 cells were treated with PhosE or Etn at pH 7.4 for 48 h and 1 million cells were collected for the quantification of PhosE and Etn by LC-MS/MS method. (Panel Cii) Fold change in intracellular levels of Etn and PhosE in Etn and PhosE-treated cells in comparison to control cells. Values and error bars shown in the figure represent mean and SE respectively from three independent experiments (*, p<0.05; ***, p<0.0001 compared with respective controls).

Having comprehensively investigated the druggability of Etn and PhosE as orally-deliverable agents, it was of interest to evaluate the antiproliferative activity of various Etn and PhosE concentrations on human prostate PC-3 cancer cells. Quantitation of cell survival showed that Etn was more effective in inhibiting cell proliferation compared to PhosE (see FIG. 8, panel Ai). The half-maximal concentration ($IC_{50}$) of Etn was ~0.88 mg/ml. Interestingly, PhosE only showed limited inhibition of PC-3 cell proliferation up to 0.5 mg/ml; concentrations greater than 0.5 mg/ml were mostly ineffective (FIG. 8, panel Ai). Next, a clonogenic cell survival assay was performed to assess the reproductive capacity of cells upon drug removal. The resulting data showed that while 2 mg/ml Etn decreased colony numbers by ~97% compared to control cells, 2 mg/ml PhosE was ineffective in decreasing colony numbers (FIG. 8, panel Aii). Representative pictures of surviving crystal violet-stained PC-3 cell colonies from control, Etn and PhosE-treated cells are shown in FIG. 8, panel Aii.

To test the generality of Etn in inhibiting proliferation of representative cancer cell lines from different tissue types, such as breast (MDA-MB-468), ovary (OVCAR-5), and pancreas (CFPAC-1), an MTT assay was performed to obtain dose-response curves of Etn treatment of these cells (FIG. 8, panel Bi). The $IC_{50}$ of Etn was 0.55, 0.29, and 1.9 mg/ml in MDA-MB-468, OVCAR-5 and CFPAC-1, respectively (FIG. 8, panel Bii). The antiproliferative activity of Etn was further tested on other prostate cancer lines (DU145 and C4-2B) and the near-normal prostate cell line, RWPE-1. The results of this analysis showed that 0.5 and 1 mg/ml Etn were more effective in reducing viability of prostate cancer lines (PC-3, DU145 and C4-2B) compared to normal prostate cells (RWPE-1) (FIG. 8, panel Bi). While 0.5 mg/ml Etn reduced survival of PC-3, DU145 and C4-2B cells by ~30-52%, RWPE-1 cells remained unaffected. Taken together, the results of these analyses suggested broad applicability of Etn in inhibiting a variety of cancer cell types.

Figure 9:
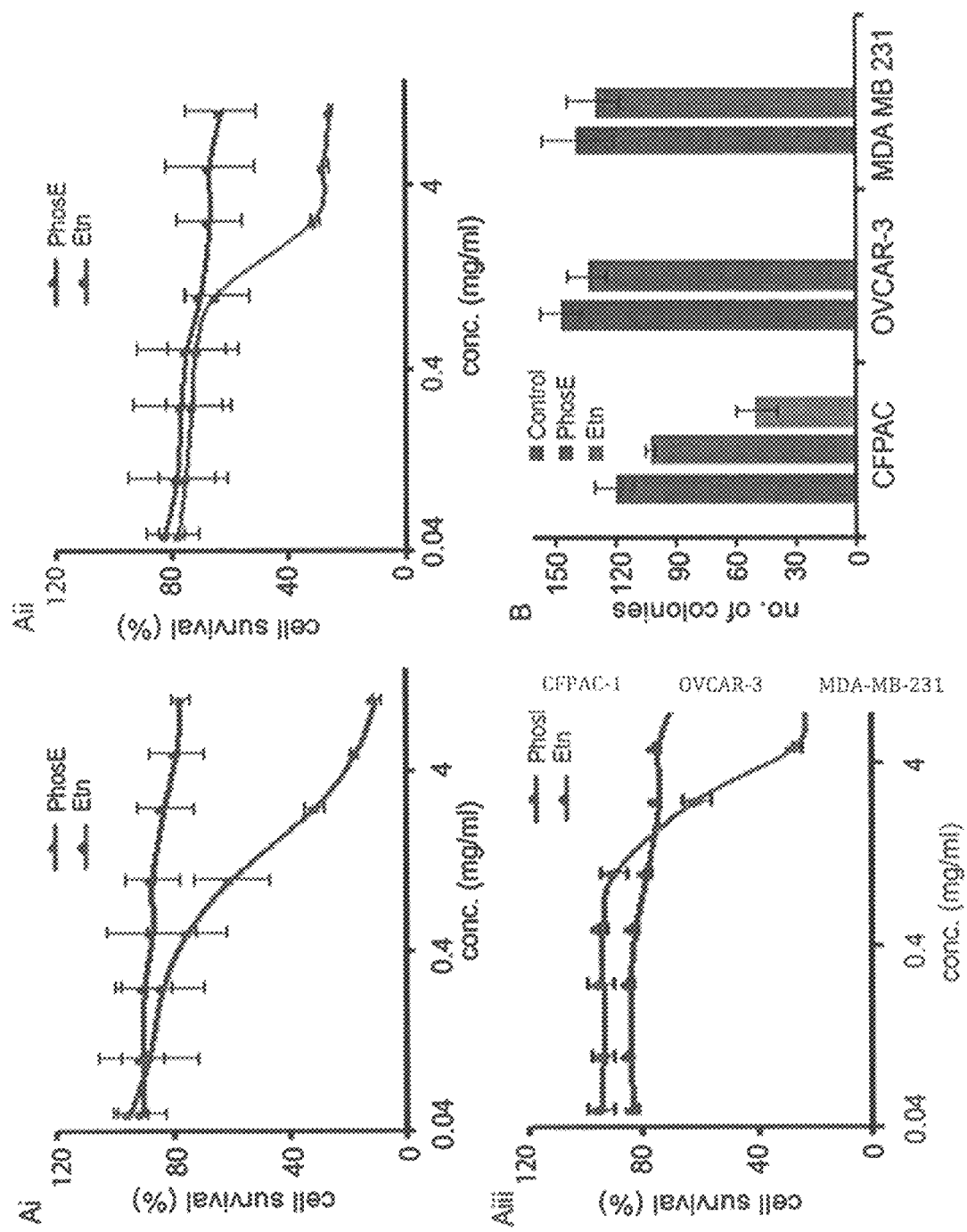
FIG. 9 shows evaluation of antiproliferative activity of PhosE and Etn in cancer cell lines from different tissue types such as breast (MDA-MB-231), ovary (OVCAR-3) and pancreas (CFPAC-1). Representative dose response curve for Etn and PhosE on the proliferation of CFPAC-1 (Ai), OVCAR-3 (Aii) and MDA-MB-231 (Aiii). The percentage of cell survival was measured by MTT assay after treating cells with increasing concentrations of Etn and PhosE for 48 h at pH 7.4. (B) Bar graph representation of crystal violet-stained surviving colonies from the control, Etn and PhosE-treated groups for CFPAC-1, OVCAR-3 and MDA-MB-231.

On the other hand, PhosE was less effective in inhibiting proliferation and colony formation of cancer cells of varying tissue-origin (FIG. 9). To better understand why Etn was more effective than PhosE in inhibiting proliferation of cancer cells, changes in intracellular levels of PhosE and Etn upon treatment with Etn or PhosE were quantified. Given that Etn and PhosE are interconvertible, it was of interest to identify the species responsible for inhibiting cell proliferation. Intriguingly, the results showed that both Etn and PhosE treatment of cells increased intracellular PhosE levels and this effect was remarkably pronounced in Etn-treated cells (FIG. 8, panel Ci). While Etn led to ~40-fold increase in PhosE levels compared to control cells, PhosE increased intracellular PhosE levels by only ~15-fold compared to control cells (FIG. 8, panel Cii). These results clearly suggest that higher intracellular PhosE levels correlated with reduced cell survival and that Etn acts as an easily absorbable pro-drug which gets converted into a cytotoxic PhosE following entry into cells.

Example 4. In Vivo Efficacy of Etn in Prostate Cancer Xenografts

Given its superior absorption, GI tract stability, non-toxicity and antiproliferative activity, Etn is clearly a better candidate than PhosE for the development of an oral anti-cancer formulation. However, keeping in mind that PhosE gets converted into Etn upon oral administration, it was envisaged that formulations containing Etn and PhosE could be potentially developed for cancer treatment. Specifically, the addition of PhosE to the formulation may provide a twofold advantage. First, as PhosE gets converted into Etn in vivo, it can increase Etn plasma levels more than Etn alone. Second, the acidic nature of PhosE can attenuate the basicity of the Etn formulation, making it more suitable for oral administration.

Figure 10:
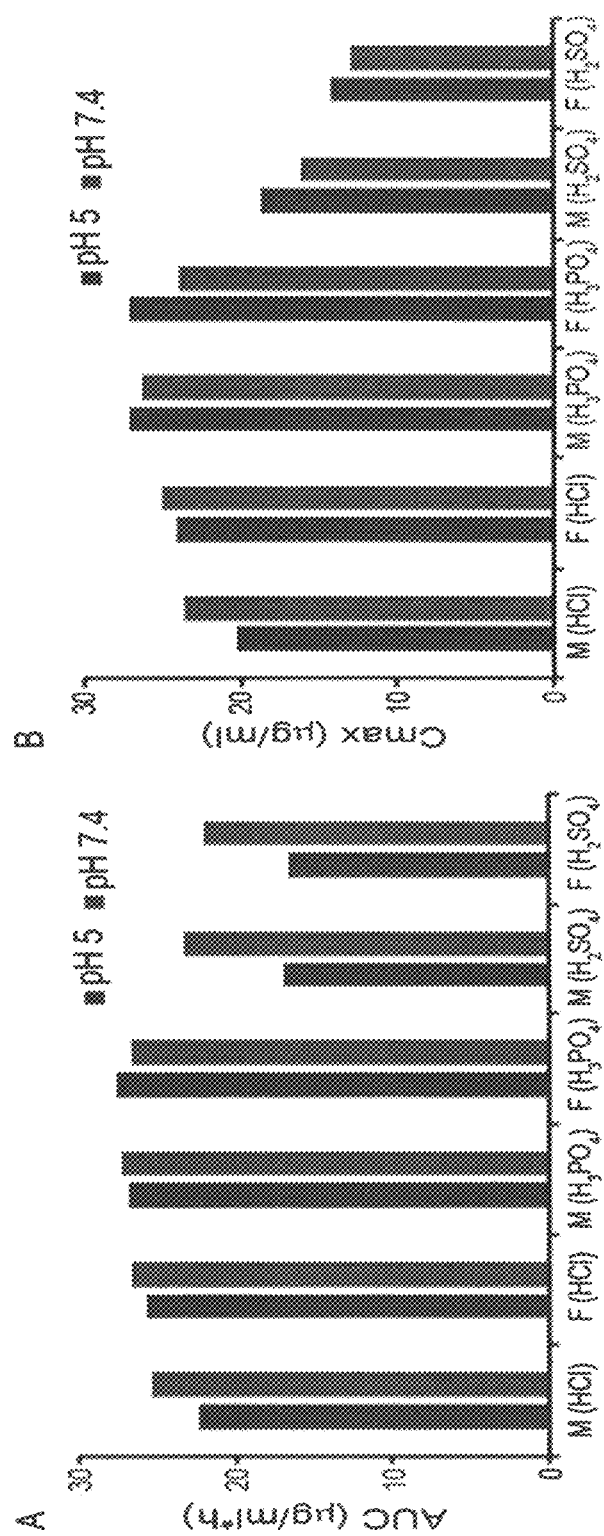
FIG. 10 shows the effect of pH, as well as the acid employed to adjust the pH of Etn formulations, on Etn absorption upon oral administration. (Panel A) $AUC_{last}$ and (Panel B) $C_{max}$ for Etn upon oral administration of different formulations containing 40 mg/kg Etn to male and female rats. These formulations differ in pH and/or acid used to adjust the pH.

To evaluate the in vivo efficacy of a repertoire of formulations containing Etn and PhosE, various formulations were tested in various molar ratios with the pH adjusted to 5.0 or 7.4 using various acids. The results showed that formulations at pH 7.4 and/or containing PhosE were either not as effective in inhibiting tumor growth as Etn at pH 5 or in some cases even accelerated tumor growth (FIG. 10). Etn absorption was independent of pH (5/7.4) or the acid ($H_3PO_4$/HCl/$H_2SO_4$) employed to adjust the pH of the formulation (FIG. 10 and Table 6). These results provided compelling grounds to further investigate formulations containing only Etn with pH adjusted to 5.0 using phosphoric acid.

TABLE 6

Comparison of pharmacokinetic parameters of Etn on day 1 following oral administration of Etn formulations that differ in either pH (5/7.4) or acid used to adjust pH of the formulations ($H_3PO_4$/HCl/$H_2SO_4$) in SD rats

| pH/Acid used/ Dose (mg/kg) | Analyte | Pharmacokinetic Parameters | | |
|---|---|---|---|---|
| | | $T_{max}$ (h) | $C_{max}$ (µg/mL) | $AUC_{last}$ (µg*h/mL) |
| pH 5/HCl/40 | Etn (M) | 0.33 | 20.21 | 24.04 |
| | Etn (F) | 0.33 | 24.13 | 33.82 |
| pH 7.4/HCl/40 | Etn (M) | 0.33 | 23.66 | 27.32 |
| | Etn (F) | 0.33 | 25.04 | 29.03 |
| pH 5/$H_3PO_4$/40 | Etn (M) | 0.33 | 27.11 | 29.49 |
| | Etn (F) | 0.33 | 27.10 | 30.92 |
| pH 7.4/$H_3PO_4$/40 | Etn (M) | 0.33 | 26.34 | 33.25 |
| | Etn (F) | 0.33 | 23.98 | 31.17 |
| pH 5/$H_2SO_4$/40 | Etn (M) | 0.33 | 18.76 | 35.56 |
| | Etn (F) | 0.33 | 14.24 | 32.27 |

TABLE 6-continued

Comparison of pharmacokinetic parameters of Etn on day 1 following oral administration of Etn formulations that differ in either pH (5/7.4) or acid used to adjust pH of the formulations ($H_3PO_4$/HCl/$H_2SO_4$) in SD rats

| pH/Acid used/ Dose (mg/kg) | Analyte | Pharmacokinetic Parameters | | |
| --- | --- | --- | --- | --- |
| | | $T_{max}$ (h) | $C_{max}$ (μg/mL) | $AUC_{last}$ (μg*h/mL) |
| pH 7.4/$H_2SO_4$/40 | Etn (M) | 0.33 | 16.07 | 28.58 |
| | Etn (F) | 0.33 | 12.87 | 41.82 |

Figure 11:
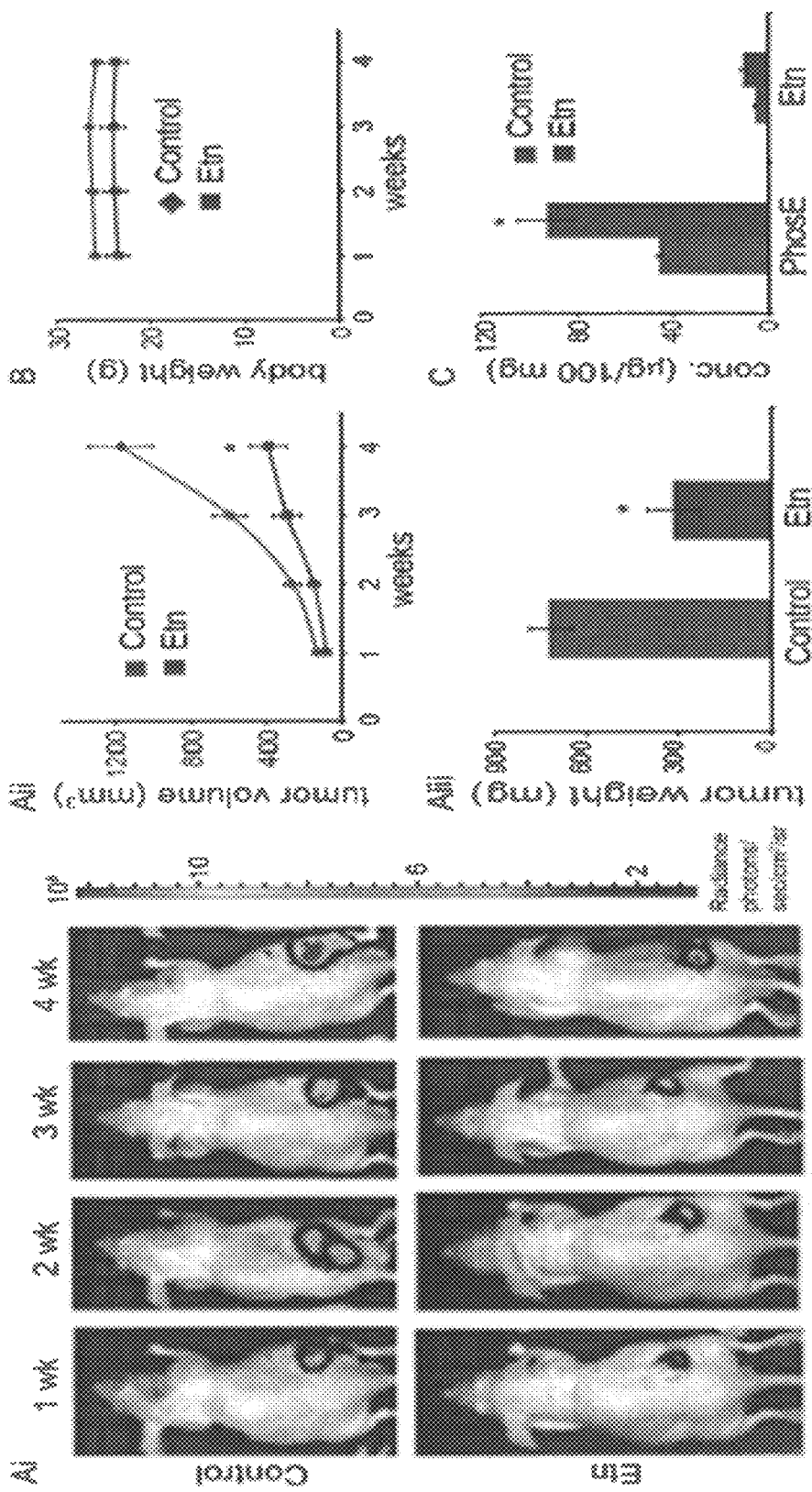
FIG. 11 shows that oral administration of 40 mg/kg Etn inhibited growth of human prostate tumor xenografts (PC-3-luc and DU145, panels Ai-C), human colon tumor xenografts (HCT116, panels Ei, Eii), and human breast (4T1, panels Di, Dii) tumor xenografts in nude mice. Panels Ai-C: PC-3-luc (1 million) or DU145 (2 million) cells in 100 µl PBS containing 25% Matrigel were subcutaneously injected in the right flank of 6-8 weeks old athymic male BALB/c mice to grow tumors. Mice with palpable tumors were randomly sorted in two groups of six mice each. Control group received vehicle (water) and treatment group received 40 mg/kg Etn adjusted to pH 5 with phosphoric acid by oral gavage for 4 weeks. (Panel Ai) Representative bioluminescent images of one animal per group indicating progression of PC-3-luc tumor growth over 4 weeks in control and Etn-treated mice. Graphical representation of the quantitative photon count from control and Etn-treated PC-3-luc tumor bearing mice for 4 weeks. (Panel Aii) PC-3-luc tumor growth monitored (by vernier calipers) over a period of 4 weeks. A ~67% inhibition in tumor volume in comparison to untreated control tumors was observed following oral administration of Etn for 4 weeks. (Panel Aiii) Weight of PC-3-luc tumors from control and Etn-treated mice. Etn treatment resulted in ~55% reduction in tumor weight in comparison to untreated control tumors. (Panel B) Body weight of vehicle and Etn fed PC-3-luc tumor bearing mice over a period of 4 weeks of treatment. (Panel C) Intratumoral levels of PhosE and Etn in vehicle and Etn-fed PC-3-luc tumor bearing mice after 4 weeks. (Panel Di) HCT116 colon tumor growth monitored (by vernier calipers) over a period of 2 weeks. An about 41% inhibition in HCT116 tumor volume in comparison to untreated control tumors was observed following oral administration of Etn for 2 weeks. (Panel Dii) Body weight of vehicle and Etn fed HCT116 tumor bearing mice over a period of 2 weeks of treatment. (Panel Ei) 4T1 breast tumor growth monitored (by vernier calipers) over a period of 2 weeks. An about 30% inhibition in 4T1 breast tumor volume in comparison to untreated control tumors was observed following oral administration of Etn for 2 weeks. (Panel Eii) Macroscopic lung metastatic growth of 4T1 in vehicle (buffer) and Etn fed 4T1 breast tumor bearing mice over a period of 4 weeks of treatment.
Figure 11:
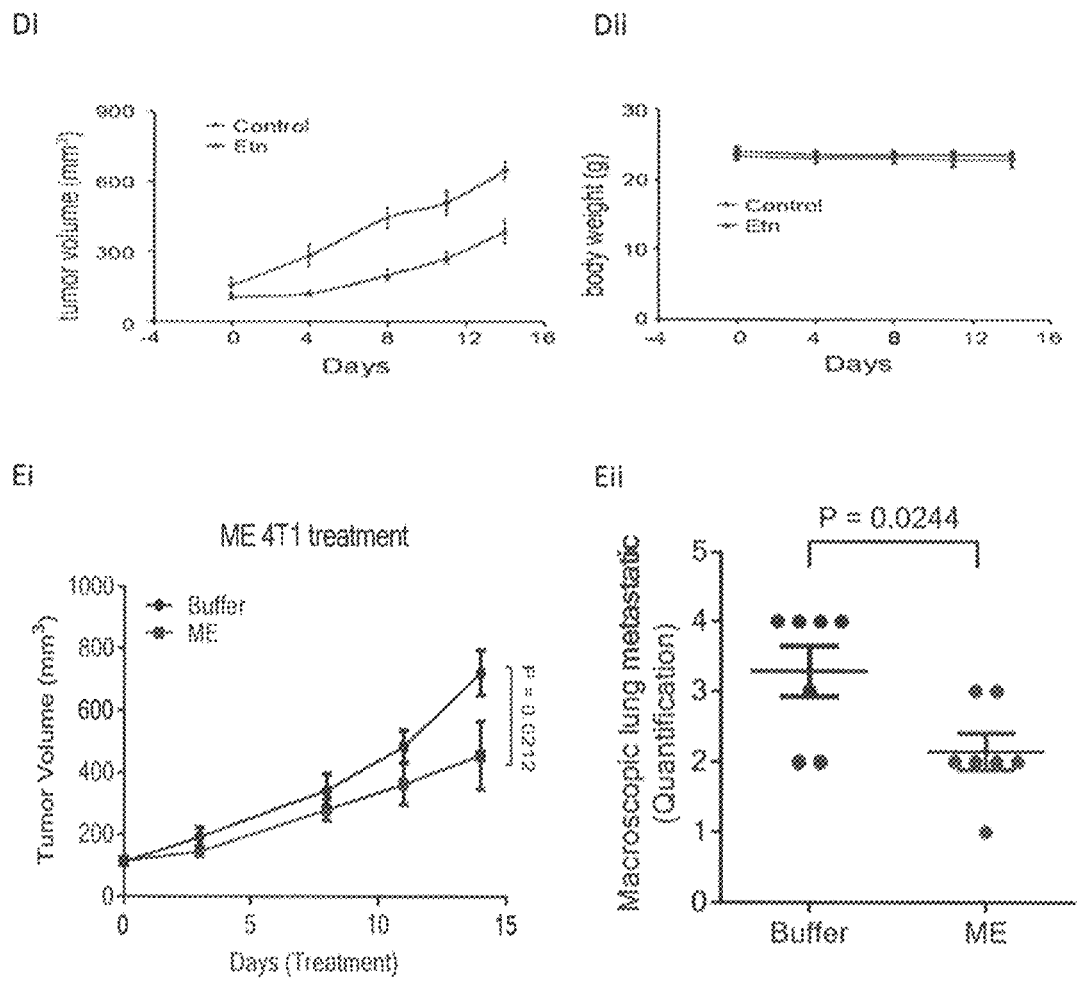

$T_{max}$: time to reach peak plasma concentration;
$C_{max}$: peak plasma concentration;
$AUC_{last}$: area under the curve;
M: Male
F: Female Next, in vivo anticancer efficacy of Etn formulations were examined in prostate (PC-3-luc and DU145), colon (HCT116), and breast (4T1) cancer xenografts (FIG. 11). Tumor bearing mice in untreated control and treatment groups received vehicle (water) or 40 mg/kg Etn, respectively, by oral gavage for 2 weeks (HCT116, 4T1) or 4 weeks (PC-3-luc and DU145). Tumor growth was measured by both vernier calipers (twice/week) and bioluminescence imaging after intraperitoneal injection of luciferin (only PC-3-luc; FIG. 11, panels Ai and Aii) once a week. A ~67% reduction in tumor volume (FIG. 11, panel Aiii) and ~55% reduction in tumor weight (FIG. 11, panel Aiv) was observed after 4 weeks of Etn treatment in the PC-3-luc xenograft model. In DU145 xenografts, a ~42% reduction in tumor volume (FIG. 11, panel Di) and ~29% reduction in tumor weight (FIG. 11, panel Dii) were observed after 4 weeks of Etn treatment. Further, a ~41% decrease in tumor volume in HCT116 xenografts was observed after 2 weeks of Etn treatment. Importantly, no apparent changes in body weight in both control and Etn-treated mice were observed over the course of treatment in both models (FIG. 11, panels B and E; suggesting that Etn is non-toxic. Quantification of intratumoral levels of Etn and PhosE after 4 weeks of Etn treatment showed that the PhosE level in Etn-treated PC-3-luc tumor-bearing mice was ~38% higher than in control mice (FIG. 11, panel C). These data are consistent with the in vitro data and further confirm that the intracellular conversion of Etn into PhosE results in intratumoral accumulation of cytotoxic PhosE, which appears to be crucial for tumor growth inhibition.

As shown in FIG. 11, panel Di, a ~41% inhibition in HCT116 tumor volume in comparison to untreated control tumors was observed following oral administration of Etn for 2 weeks. The body weight of vehicle and Etn fed HCT116 tumor bearing mice did not change significantly over a period of 2 weeks of treatment (FIG. 11, panel Dii).

As shown in FIG. 11, panel Ei, a ~30% inhibition in 4T1 breast tumor volume in comparison to untreated control tumors was observed following oral administration of Etn for 2 weeks. (Panel Eii) Macroscopic lung metastatic growth of 4T1 in vehicle (buffer) and Etn fed 4T1 breast tumor bearing mice over a period of 4 weeks of treatment.

Example 5. Inhibition of Choline Kinase (CK) Activity Attenuates Etn Antiproliferative Activity Having confirmed that Etn gets converted into PhosE intracellularly, it was of interest to identify the enzyme responsible for the conversion of Etn into PhosE. Two enzymes, ethanolamine kinase and choline kinase (CK) are known to catalyze conversion of Etn into PhosE. However, since CK is known to be overexpressed in many types of cancer, including lung, prostate and breast (Ramfrez de Molina A, R. et al., Biochem. Biophys. Res. Commun., 296:580-583 (2002)), it was of interest to examine if CK catalyzes the conversion of Etn into PhosE in PC-3 cells. This was examined by determining the survival of PC-3 cells following Etn treatment in the presence or absence of a CK inhibitor. While Etn treatment alone reduced cell proliferation by ~33% (FIG. 12, panel A), CK inhibition significantly attenuated Etn-induced reduction in cell proliferation to ~17% (FIG. 12, panel A). At this concentration, the CK inhibitor itself did not significantly affect proliferation of PC-3 cells.

PhosE levels in PC-3 cells treated with Etn alone or in combination with CK inhibitor were also quantified. The results of this analysis showed that pharmacological inhibition of CK reduced conversion of Etn into PhosE by ~19% (FIG. 12, panel B). A siRNA approach was further employed to confirm the role of CK in Etn-induced cell death. Knockdown (KD) of CK using siRNA significantly abated Etn-mediated reduction in viability of PC-3 cells (FIG. 12, panel C). While 0.5 mg/ml Etn reduced cell survival of PC-3 cells by ~38%, cell viability in CK KD PC-3 cells was decreased by only ~11% (FIG. 12, panel C). These results underscore CK's role in the conversion of Etn to PhosE in PC-3 cells. It was further found that CK expression is low in normal prostate cell line (RWPE-1) compared to prostate cancer cell lines (PC-3, DU145 and C4-2B) (FIG. 12, panel D), which may underlie the differential sensitivity of normal versus cancer cells to Etn (FIG. 8, panel Bi).

Next, it was of interest to examine why Etn treatment selectively affected cancer cells and spared normal ones. To this end, publicly-available datasets for CK gene expression in prostate cancer patients were explored, as well as detection of CK protein expression by immunohistochemical staining of tumor versus adjacent normal tissue from prostate cancer patients. The results of these analyses showed that CK is highly overexpressed in prostate cancer tissue compared to adjacent normal (FIG. 12, panels E, Fi and Fii). An in-silico analysis further showed that prostate cancer exhibits 2.1-fold higher CK expression compared to normal prostate tissue (FIG. 12, panel E). Quantification of CK immunostaining showed that CK expression was 1.5-fold higher in prostate cancer tissue compared to adjacent normal tissue (FIG. 12, panel Fii). This differential CK expression (both at gene and protein level) is consistent with the notion that cancer cells are more sensitive to Etn treatment than normal cells.

Example 6. Etn Activates Mitochondrially-Mediated Death Pathways and Affects Cellular Respiration and Metabolism To identify the underlying signaling pathways responsive to Etn, expression levels of cell-cycle and apoptosis regulatory molecules in cultured PC-3 cells were examined at the transcriptional and translational levels. In particular, immunoblot analysis showed that while Etn treatment downregulated protein expression of pRb, Cdk4, and Cdk2, and upregulated p21 expression, suggesting that Etn inhibits cell-cycle progression (FIG. 14, panels A and B). Further, in response to Etn treatment, an increase in protein expression of proapoptotic markers (c-PARP and Bim) and a decrease in antiapoptotic molecules (Bcl-2) was observed, thereby implicating a mitochondrially-mediated death pathway (FIG. 14, panel A). This was confirmed at transcriptional level where Etn upregulated p21, PARP1, Bax and Bid, and downregulated Bcl-2 (FIG. 14, panel C).

Extending this analysis to Etn-mediated inhibition of tumor growth in vivo, tumor cell lysates were prepared from control and 40 mg/kg Etn-treated mice and evaluated for expression of cell-cycle regulatory markers, proapoptotic markers and anti-apoptotic markers. The results of this analysis showed that Etn upregulated p21, Bax, pBcl2 c-PARP, Bim and Bid (FIG. 14, panel C). Since p21, Bax and pBcl2 are downstream effectors of p53, p53 expression levels were examined in control and Etn-treated tumors, as well as control and Etn-treated PC-3 cells. The results of this analysis showed that Etn-treated tumors were found to display higher levels of p53 protein than untreated control tumors (FIG. 14, panel B).

Immunohistochemical staining of paraffin-embedded samples for Ki67 (cell proliferation) and c-PARP (apoptotic) showed a decrease in Ki67 and an increase in c-PARP in treated tumors compared to control ones (FIG. 14, panels Di and Dii). While ~62% cells were Ki67-positive in untreated control tumors, Ki67 positivity was reduced to ~40% in Etn-treated tumors (FIG. 14, panel Dii).

The in vitro efficacy dose of Etn ($IC_{50}$: 0.88 mg/ml) was extrapolated to in vivo efficacious dose (140.57 mg/kg; therapeutic index=5) using NIH guidelines. Intriguingly, supraphysiological Etn concentrations were found to be required for in vitro activity. However, Etn was surprisingly found to exhibit remarkable in vivo efficacy with 40 mg/kg Etn which is ~3.5 times lower than the extrapolated dose for in vivo efficacy. This indicates that Etn exploits unknown aspect(s) of cancer physiology in vivo to evoke its anticancer activity, which cannot be mimicked in a cell culture system.

Annexin-V is known to bind to phosphatidylserine (PS) lipids which flip to the outer leaflet of plasma membrane in apoptotic cells (Vermes I. et al., J. Immunol. Methods, 1995, vol. 184, pp. 39-51). Annexin-V binding to PS is therefore a good indicator of cells undergoing apoptosis. Consistent with a role for Etn in inducing apoptosis, flow cytometric analysis of Etn-treated PC-3 cells showed that that ~8% untreated cells were annexin-V positive, which increased to ~25% upon Etn treatment (FIG. 15).

Example 7. Etn Affects Cellular Respiration and Metabolism in Both In Vitro and In Vivo Models of Prostate Cancer It is well-recognized that HIF1-α plays a pivotal role in cancer progression and regulates several survival pathways in cancer cells. For example, HIF1-α regulates glucose metabolism under hypoxia by inducing the expression of glucose transporters to increase glucose uptake to fulfill the energy demands of rapidly proliferating cancer cells through glycolysis. Recently, HIF1-α has also been shown to regulate glutamine metabolism (Marin-Hernandez, A., et al., Mini Rev Med Chem, 9(9), 1084-101 (2009)). In addition, it has been reported that p53 pathway is activated upon energetic/metabolic stress in cells (Munoz-Pinedo, C. et al, Cell Death Dis, 3:e248 (2012)). Reports also indicate that PhosE accumulation in cells affects cellular respiration and that both monoethanolamine (Etn) and phosphoethanolamine (PhosE) impair mitochondrial respiration by altering oxygen consumption rate (OCR) in isolated mitochondria (Gohil, V. M., et al., J Biol Chem, 288(49):35387-95 (2013); Modica-Napolitano, J. S. et al, Biol Psychiatry, 55:273-277 (2004)). In view of these findings, it was hypothesized that accumulation of PhosE alters HIF1-α function so as to impair glucose/glutamine metabolism, thereby leading to bioenergetic/metabolic stress in cells, which activates p53-induced cell death.

To test this hypothesis, HIF1-α expression levels were analyzed in Etn-treated tumors and PC-3 cells. This analysis showed that Etn treatment resulted in 50-fold reduction in HIF1-α transcript levels in PC-3 cells compared to control cells (FIG. 14, panel B). Downregulation of HIF1-α protein expression was also found in Etn-treated tumors relative to untreated control tumors (FIG. 14, panel E). DMOG, an HIF1-α activator, was then employed to test whether Etn-mediated cell death in PC-3 cells was associated with HIF1-α stabilization (active HIF1-α signaling). In this case, Etn was found to be more effective in reducing survival in PC-3 cells (relative to controls) via active HIF1-α signaling due to HIF1-α stabilization by DMOG (FIG. 14, panel F), thereby suggesting a role for the HIF1-α signaling axis in Etn-mediated cell death. These data provide a plausible explanation for the discrepancy between the dosages for in vitro and in vivo efficacy. Specifically, these data suggest the likelihood that Etn is more effective in vivo due to active HIF1-α signaling in hypoxic tumor tissues compared to cultured cells under normoxic condition.

Further, oxygen consumption rates (OCR) in control and Etn-treated cells were measured as a function of cell number, while glucose and glutamine contents were measured in cultured cells and tumors from control and Etn-treated mice. Etn was found to reduce OCR in PC-3 cells, whereby the extent of reduction varied with cell number such that OCR in treated cells was reduced by ~26% compared to controls at a concentration of $1 \times 10^6$ cells/ml (FIG. 14, panel G). In addition, both glucose and glutamine contents were found to be significantly reduced in Etn-treated tumors (FIG. 14, panels Hi and Hii) and cells (FIG. 14, panels J and Jii) relative to untreated control tumors and cultured cells, although the effects were more pronounced in tumors than cultured cells. It is likely that HIF1-α-dependent pathways are not as active in cultured PC-3 cells having an adequate supply of oxygen and nutrients. This provides a likely explanation for the discrepancies in pharmacological effects of Etn observed under in vitro and in vivo conditions. These data underscore the likelihood that Etn employs different cell-cycle and apoptosis regulators to mediate in vivo and in vitro effects due to differential extent of HIF1α signaling under these two conditions. Further, as alluded to earlier, Etn possibly exploits an unknown aspect of the in vive cancer environment which may drive disparate mechanisms in cultured cells versus physiological systems in vivo. Additionally, it was found that CK inhibition abrogates Etn-mediated decreases in cellular glucose and glutamine contents (FIG. 14, panels Ji and Jii). Taken together, these data suggest that Etn altered intracellular glucose and glutamine levels in tumors and cultured prostate cancer cells.

Having identified the effects of Etn on intracellular glucose and glutamine that impact glycolysis and other metabolic pathways, 2-D gel electrophoresis of tumor lysates from control and Etn-treated animals was carried out to identify and characterize differentially-expressed proteins by LC-MS/MS analysis. Two enzymes of glycolysis (glyceraldehyde-3-phosphate dehydrogenase and phosphoglycerate kinase-1) and one enzyme of glutamine metabolism (delta-1-pyrroline-5-carboxylate synthase) were found to be downregulated following Etn treatment, which can exacerbate the metabolic crisis in Etn-treated tumor cells (FIG. 16, Table 7).

TABLE 7

Protein ID and relative quantity of proteins downregulated in
Etn treated tumors in comparison to untreated control tumors

| Protein ID | Protein name | Relative Quantity (AUC: Intensity × Time) |
|---|---|---|
| P 04406 | Glyeeraidehyde 3-phosphate dehydrogenase | 1641 |
| P 00558 | Phosphoglycerate kinase 1 | 13307 |
| P 54886 | Delta-1-pyrroline-5-carboxylate synthase | 5126 |

Example 8. Etn Alters Cellular Lipids and Impairs Mitochondrial Integrity In Vivo Since Etn is a precursor of lipid constituents of membrane bound cellular structures, it was of interest to determine if Etn treatment altered the structural integrity of membrane bound organelles or affected the dynamics of membrane fission fusion events. To explore this, transmission electron microscopy (TEM) of tumors from control and Etn-treated mice was performed. TEM micrographs showed significant structural differences in mitochondria from control and treated groups. Specifically, mitochondria were found to be elongated along with degraded matrix in treated tumors (FIG. 17, panel Aii) compared to control tumors (FIG. 17, panel Ai). In addition, more osmiophilic granules were observed in treated tumors (FIG. 17, panel Aiv) compared to untreated control tumors (FIG. 17, panel Aiii), indicating accumulation of lipids in treated tumor cells. These results suggest that Etn treatment leads to accumulation of lipids in cells, alterations in mitochondrial structure, and lipid-mediated activation of cell death pathways.

Given that TEM micrographs of Etn-treated samples depicted the presence of many lipid granules, it was of interest to examine which lipids are specifically upregulated in Etn-treated tumors by a lipidomics analysis of tumors from control and Etn-treated groups. A total of 402 lipids from various lipid classes such as phosphatidylethanolamine (PE), phosphatidylcholine (PC), phosphatidylserine (PS), lysophospholipids, ceramides, and sphingomyelin (SM) were quantified. The results showed that levels of 22 lipids out of 402 were increased in tumors from Etn-treated group (FIG. 17, panel B). While these lipids mostly belonged to PE class (FIG. 17, panel Bi), other lipids from the PS (FIG. 17, panel Bii), PC (FIG. 17, panel Bii) and SM (FIG. 17, panel Biv) lipid classes were also increased. Based on these data, it was concluded that altered lipid levels may perturb lipid homeostasis upon treatment with Etn, thereby resulting in changes in membrane properties that initiate a cascade of events deleterious for cell survival.

Taken together, the results demonstrate that Etn possesses desirable molecular traits and anticancer attributes for an orally-deliverable broad spectrum cancer therapeutic. Etn exploits intrinsic overexpression of CK in cancer cells to convert into cytotoxic PhosE. Further, Etn treatment through downregulation of HIF1-α precipitates a bioenergetics/metabolic crisis by activating p53-mediated signaling cascade culminating into cell death (FIG. 17, panel C). The results of this study uncover a previously unrecognized molecular link between the Kennedy pathway of lipid biosynthesis and cellular respiration/metabolism in cancer cells, whereby Etn targets glucose metabolism, the indisputable driver of cancer progression.

Example 9. Binding of Ethanolamine to Proteins in Plasma

Plasma from human, dog, rat and mouse were thawed and incubated at 37° C. The pH of the plasma was adjusted to 7.4 using dilute hydrochloric acid. A 5 µL aliquot of ethanolamine (2 mM) was spiked into 995 µL of plasma and incubated at 37° C. for 30 min in $CO_2$ incubator. One mL aliquots of plasma were transferred to ultrafiltration tubes for analysis. All ultrafiltration tubes were centrifuged at 1000 g for 20 min. Samples from top and bottom chamber of ultrafiltration tube were collected. Equal volume of blank plasma and ultrafiltrate were mixed to ultrafiltrate and plasma to make the matrix same. Samples were processed by using acetonitrile containing internal standard and subjected to LC/MS/MS analysis. The results from this analysis showed that ethanolamine exhibits low binding potential to plasma proteins with percent bound values less than 85% (data not shown).

Example 10. Materials and Methods

Cell Lines, Media, Antibody and Reagents:
Prostate (PC-3, PC-3 luc), breast (MDA-MB-468), ovarian (OVCAR 5), pancreatic (CFPAC-1) and colon (HCT116) cancer cell lines and near-normal prostate RWPE-1 cells were used in the present study. PC-3-luc cells were from Perkin Elmer (Waltham, Mass.) and all other cell lines were from ATCC. PC-3 was cultured in RPMI-1640 medium; OVCAR 5 and CFPAC-1 cell lines were cultured in DMEM medium; MDA-MB-468 and luciferase-expressing PC-3 cells were cultured in MEM medium. All cell lines were grown in medium containing 10% FBS and 1% penicillin/streptomycin and maintained in 5% $CO_2$ atmosphere at 37° C. Primary antibodies to Cdk 4, Cdk 2, p-Rb, p21, Bim, Bid, Bcl-2, pBcl-2, cleaved poly (ADP-ribose) polymerase (PARP) and 1a actin were from Cell Signaling (Beverly, Mass., USA). Ki67, HIF1-α and p53 were from BD Bioscience (San Jose, Calif.) and Choline kinase was from Proteintech (Rosemont, Ill.). Bax, GAPDH and horseradish peroxidase (HRP)-conjugated secondary antibodies were from Santa Cruz Biotechnology (Santa Cruz, Calif.). Primary antibodies for Ki67, HIF1-α and p53 were from BD Bioscience (San Jose, Calif.). Choline kinase antibody was from Proteintech (Rosemont, Ill., USA). Phosphoethanolamine, monoethanolamine, luciferin and Dimethyloxalyiglycine, N-(Methoxyoxoacetyl)-glycine methyl ester (DMOG) were from Sigma (St Louis, Mo.). Choline kinase-α inhibitor was from Calbiochem (San Diego, Calif.). siRNA against choline kinase was from GE Dharmacon (Lafayette, Colo.).

Stability of Etn and PhosE in Simulated Gastric (SGF) and Intestinal Fluid (SIF):
Simulated gastric fluid was prepared as per U.S. Pharmacopeia (USP) methods. Sodium chloride (2 g) and pepsin (3.2 g, from porcine stomach mucosa) were dissolved in 7.0 ml hydrochloric acid and Milli-Q water to make up the volume to 1000 ml and the pH was adjusted to 1.2. Simulated intestinal fluid was also prepared as per USP methods, 6.8 g monobasic potassium phosphate was dissolved in 250 ml Milli-Q water. To this, 77 ml 0.2 N sodium hydroxide and 500 ml Milli-Q water was added along with 10 g pancreatin (from porcine pancreas). The pH of the solution was adjusted to 6.8 and the volume was made up to 1000 ml. Etn (10 µM) and PhosE (10 µM) were spiked into pre-incubated SGF and SIF for varying times followed by their quantification using LC-MS/MS analysis. Specifically, samples (100 µL) were withdrawn at 0, 15, 30, 60 min from SGF and at 0, 30, 60, 120 min from SIF; quenched with equal volume of acetonitrile, vortex mixed, centrifuged and supernatant was taken for analysis.

Pharmacokinetic (PK) Studies of PhosE and Etn:

Pk studies (oral and intravenous) were carried out in male BALB/c mice following administration of PhosE or Etn. PhosE and Etn concentrations for oral administration were 60 and 40 mg/kg, respectively and for intravenous administration were 3 and 2 mg/kg, respectively. Nine animals per group were used for PK studies. A sparse sampling design was used to collect blood samples from animals at 5 min, 10 min, 15 min, 30 min, 1, 2, 3, 4, 5, and 6 h in $K_2$EDTA coated tubes. Plasma was collected from blood by centrifugation of samples at 8000 g for 10 min. Plasma samples were stored below −60° C. until further analysis.

Bioanalysis:

All plasma samples were processed using protein precipitation method. An aliquot of sample (100 μL) was added to 200 μL of acetonitrile, containing 0.3 μg/mL 4-amino-1-butanol as an internal standard, and mixed by vortex mixing for 3 min. Samples were centrifuged at 12000 g for 10 min and 250 μl of supernatant was transferred to auto-sampler vials for LC-MS/MS analysis. The stock solutions of PhosE and Etn were prepared in water at 1 mg/mL and 4-amino-1-butanol (internal standard) was prepared at 0.3 μg/ml in acetonitrile. A calibration curve range of 0.1 μg/mL to 50 μg/mL was employed for the quantification of analytes. The calibration curve consisted of blank, blank with internal standard and 6 non-zero calibration standards. The calibration standards were within 15% at the nominal concentration and 20% at LLOQ. All samples were derivatized and analyzed using liquid chromatography tandem mass spectrometric (LC-MS/MS) method (Agilent 6410 series). Auto-sampler temperature was set at 10° C. and 10 μl sample was mixed with 10 μl OPA solution (50 mg/ml OPA in 60% EtOH) and 10 μl 2-mecaptoethanol solution (40 μl/ml 2-mecaptoethanol in 400 μl pH 9.4 buffer (0.1 M Sodium tetra borate decahydrate)). The derivatization reaction time was 2 min and injection volume was 5 μl. A positive ionization mode with multiple reaction monitoring (MRM, m/z Q1/Q3) of PhosE (m/z 142.1/44.1, RT 5.3 min), Etn (m/z 62.1/29.0, RT 6.3 min), glutamine (m/z 147/130, RT 2.5), IS (m/z 90.0/55.0, RT 6.6 min) and a negative ionization with multiple reaction monitoring (MRM, m/z Q1/Q3) of glucose (m/z 179.0/59.0, RT 2.4), was employed. The ion spray voltage was set at 3500 V, ionization temperature set as 300° C. and drying gas flow rate was 10 L/min. Data acquisition and quantitation were performed using Mass Hunter software (Agilent Technologies). Separation was achieved using HP1100 series LC (Agilent Technologies, Wilmington, Del.) equipped with a photodiode array (PDA) detector, using an Agilent Zorbax reversed-phase (SB-C18, 3.0×250 mm, 5.0 μm) column or a Thermo Fisher Acclaim™ Trinity™ P1 (Silica, 2.1×150 mm, 3.0 μm) column. A gradient method was employed to separate the individual components using mobile phase A (20 mM Ammonium acetate in water) and mobile phase B (ACN). The gradient elution method with 10% B at 0 min, 90% B at 20 min, held for 10 min, back to 10% B at 30 min with a flow rate of 0.2 ml/min was employed.

Pharmacokinetic Analysis:

PK parameters were calculated from the concentration-time data using the non-compartmental analysis tool of Phoenix WinNolin® software (version 6.3, Pharsight, St Louis, Mo.). The area under the concentration time curve ($AUC_{last}$) was calculated by the linear trapezoidal rule. Following oral administration, peak concentration ($C_{max}$) and time for the peak concentration ($T_{max}$) were the observed values. The clearance (CL) and volume of distribution (Vss) were estimated following IV dose administration. The elimination rate constant value (k) was obtained by linear regression of the log-linear terminal phase of the concentration-time profile using at least three declining concentrations in terminal phase with a correlation coefficient of >0.8. The terminal half-life value ($T_{1/2}$) was calculated using the equation ln 2/k. Oral bioavailability was calculated by taking the ratio of dose normalized $AUC_{last}$ following oral administration to IV administration.

In Vitro Cell Proliferation and Colony Survival Assays:

Proliferation of PC-3, DU145, C4-2B, RWPE-1, MDA-MB-468, OVCAR-3 and CFPAC-1 cells treated with Etn/PhosE were evaluated using a colorimetric MTT assay. Cells were seeded well in 96 well plates and after 24 h treated with varying concentrations (0.05-5 mg/ml) of Etn/PhosE at pH 7.4. After 48 h, drug containing medium was replaced by medium containing MTT (tetrazolium bromide) at a concentration of 0.5 mg/ml. The yellow tetrazolium salt is reduced to insoluble purple formazan by viable cells. After 4 h of incubation in dark, formazan crystals produced by viable cells were dissolved by 200 μl DMSO and the amount of formazan crystals formed was quantified by recording the absorbance at 570 nm using multi-well plate reader. For the colony assay, PC-3 cells were treated with 2 mg/ml Etn and PhosE for 48 h, washed and replaced with regular RPMI medium. After 10 days, colonies were fixed with 4% formaldehyde, stained with crystal violet and counted.

In Vivo Tumor Growth and Bioluminescent Imaging:

One million PC-3 luc cells expressing luciferase in 100 μl PBS containing 25% Matrigel were subcutaneously injected in the right flank of 6-8 weeks old male BALB/c nude mice. After 15 days, mice with palpable tumors were randomly sorted in two groups of six mice each. Control group was fed with vehicle (water) and the treatment group was fed with 40 mg/kg Etn pH 5.0 adjusted with phosphoric acid by oral gavage for four weeks. In vivo prostate tumor growth was measured twice a week by vernier caliper and once a week by bioluminescent imaging. Tumor volume was calculated after measuring length and breadth of the tumor using vernier caliper. For bioluminescent imaging of tumors, mice anesthetized with isoflurane were intraperitoneally injected with 100 μl of 30 mg/ml luciferin and luciferase activity was measured by real time bioluminescent imaging on the IVIS in vivo imaging system using CCD camera. Images were recorded with an integration of 20 s and four binnings of 100 pixels. Animal experiments were in compliance with GSU IACUC guidelines.

Immunoblot Analysis:

Proteins were resolved by polyacrylamide gel electrophoresis and transferred onto polyvinylidene difluoride membranes (Millipore, Billerica, Mass., USA). The membranes were blocked in Tris-buffered saline containing 0.05% Tween-20 and 5% fat-free dry milk and incubated first with primary antibodies and then with horseradish peroxidase-conjugated secondary antibodies. Specific proteins were visualized with enhanced chemiluminescence detection reagent according to the manufacturer's instructions (Pierce Biotechnology, Rockford, Ill., USA).

Immunohistochemical Staining:

Tumors were formalin-fixed, paraffin-embedded and 5 μm thick prostate tumor sections were stained for Ki67 and c-PARP, and prostate cancer TMA (US Biomax, Derwood, Mass.) was immunostained for choline kinase. All stained slides were examined by a pathologist in a blinded-manner.

In Silico Analysis of Choline Kinase Expression:

Choline kinase A expression levels in prostate cancers were analyzed using Oncomine (https://www.oncomine.org/resource/login.html). Reporter ID and platform for datasets used were as follows: Gene rank 229, 839, 2059, 1589, 8514, 1206, 546 analyzed on a Human Genome U133 Plus 2.0 Array.

RNA, cDNA Preparation and Real Time-PCR:

RNA was extracted from control and 2 mg/ml Etn-treated PC-3 cells using a RNeasy kit from Qiagen (Hilden, Germany), and quantified using NanoDrop. Reverse transcription of RNA was performed for the first strand cDNA synthesis using a first strand synthesis kit (GoScript™ Reverse Transcription System-A5000) from Promega (Madison, Wis.). The quality of synthesized cDNAs was checked on an agarose gel. RT-PCR of cDNA samples (in duplicates) was performed using iQ™ SYBR® Green Supermix from Bio-Rad (Hercules, Calif.) as per manufacturer's instructions. The RT-PCR primers were designed manually, checked with the primer3 software and ordered from Sigma (St Louis, Mo.).

Measurement of Oxygen Consumption Rate (OCR):

OCRs were measured using a computer-interfaced oxygen electrode (Hansatech Instruments, Inc., Norfolk, England) by monitoring the initial rate of oxygen consumption at 37° C. and atmospheric oxygen concentration (230 μM $O_2$). The measurements were initiated by adding 500 μl control and 2.0 mg/ml Etn treated cells at various concentrations into electrode chamber pre-equilibrated with 500 μl fresh media.

Electron Microscopy of Necropsied Tumor Tissue:

Tumors were collected and fixed in 2% paraformaldehyde, 0.1% glutaraldehyde in 0.1 M sodium cacodylate pH 7.2 for 2 h, post-fixed with 1% osmium tetroxide for 1.5 h, washed, and stained en bloc for 1 h in 1% aqueous uranyl acetate (pH 3.3). The samples were then washed again, dehydrated with a graded ethanol series (through 3×100%) and embedded in Spurr epoxy resin (Electron Microscopy Sciences). Ultrathin sections were cut on a Boeckeler MTx ultramicrotome, counterstained with lead citrate, and examined on a LEO 906e transmission electron microscope.

Lipidomics:

Lipidomic analysis of control and Etn-treated tumors was performed by the Lipidomics Core Facility at Wayne State University.

Statistical Analysis:

Results are expressed as mean values of at least three independent experiments. p values (Student's t test) were calculated using Microsoft Excel software.

CYP Inhibition Assay:

Preparation of Stock Solutions: 20 mM stock solutions of Etn and PhosE were prepared in ACN:DMSO (80:20) mixture and subsequent test dilutions of inhibitor (final concentrations of 100, 50, 25, 12.5, 6.25, 3.125, 1.563, 0.781, 0.390, 0.195 and 0.098 mM) were prepared in ACN:DMSO (80:20). Stock solutions for each CYP specific probe substrate were prepared in such a way that the final concentration is below the reported Km value. A microsome-buffer-substrate mixture (MBS mix) was prepared for each isozyme by pre-mixing appropriate volumes of sodium phosphate buffer (pH 7.4, 50 mM), microsomes and substrate. MBS mix (179 μl) was transferred to a 96-well reaction plate wells to which 1 ml of inhibitor stock solution was added to achieve the final target inhibitor concentration. The reaction plate was preincubated for 10 min at 37° C. followed by reaction initiation by addition of 20 ml of 10 mM NADPH solution. The reaction plate was then incubated at 37° C. for a predetermined time period and then quenched with 200 μl ACN for all CYPs and 200 μl 1% formic acid in water:ACN (70:30) for CYP1A2. In all cases, the final incubations after addition of substrate and inhibitor contained 0.1% DMSO (v/v), and the total organic solvent (DMSO and ACN) content was less than or equal to 1% (v/v).

Bioanalysis for CYP Inhibition Samples.

All samples were processed using protein precipitation method and analyzed by employing positive (for all CYPs) and negative (for CYP2A6, 2C19 and 2E1) ionization LC-MS/MS. The peak area ratio of analyte to IS was used for calculations. An isocratic method comprising 5 mM ammonium formate and ACN (40:60) with 0.05% formic acid was used for elution. For CYP2C19, a mobile phase consisting of 5 mM ammonium formate and ACN (30:70) was used. The analytes and internal standards were retained on a BDS Hypersil Phenyl (15×4.6 mm, 5 μm, Thermo, USA) column. A flow rate of 0.5 ml/min (CYP1A2), 0.6 ml/min (CYP2C19, CYP2E1), 0.7 ml/min (CYP2C9), 0.8 ml/min (CYP2A6, CYP3A), 1.0 ml/min (CYP2B6, CYP2C8, CYP2D6) was maintained using Shimadzu Prominence solvent delivery system (LC-20AD). The mobile phase was degassed using degasser (DGU-20A3), samples were loaded into autosampler (SIL-HTc) and the column temperature was maintained at 40° C. by column oven (CTO-20A). Injection volumes for the samples were as follows: 5 ml (CYP1A2, CYP2D6, and CYP3A), 10 ml (CYP2B6, CYP2C8, and CYP2E1) and 20 ml (CYP2A6, CYP2C9, and CYP2C19). Data was collected and processed using Sciex Analyst 1.4.2.

Data Analysis:

The $IC_{50}$ value was estimated from the percentage reduction in CYP activity at eleven inhibitor concentrations with respect to control. The area ratio of the metabolite in the sample without inhibitor was considered as 100%, and the percentage reduction in the CYP activity at each inhibitor concentration was determined relative to the no-inhibitor area ratio using the following equation:

$$\% \ CYP \ \text{activity} = \frac{\text{Area ratio of metabolite at each dilution}}{\text{Area ratio of no} - \text{inhibitor controls}} \times 100$$

The non-linear regression model in GraphPad Prism software was used to analyze the percent CYP activity data at different concentrations and the data were fitted to the following equation and $IC_{50}$ was calculated:

$$Y = \text{Bottom} + \frac{(\text{Top} - \text{Bottom})}{1 + 10^{(logIC_{50} - X)*Hill \ coefficient}}$$

Blood Plasma Concentration Ratio Assay:

In order to evaluate blood-plasma concentration ratio of Etn and PhosE, blood was collected from mice in $K_2EDTA$ coated tubes. Blood (1990 μl) was transferred to separate microfuge tubes and 10 μl of 10 mM stock solutions of Etn or PhosE were added followed by incubation at 37° C. 100 μl and 300 μl aliquots were collected at time points 0, 15, 30 and 60 min. 100 μl water was added to each of the 100 μl aliquots followed by vortexing, centrifugation at 8000 g for 10 min, and collection of the supernatants for bioanalysis. The 300 μL aliquots were centrifuged at 8000 g for 10 min to separate the plasma, followed by collection of the supernatants for bioanalysis. Stock solutions of Etn and PhosE were prepared in water.

Pk Simulation:

Concentration-time (CT) curve prediction following repeated dose administration using single dose administration data was performed using Phoenix WinNonlin 6.3 software. First, sparse sampling CT data (0 to 6 h) for 3 different oral doses were fitted in a first-order one-compartment model to calculate the V/F (volume of distribution), K01 (distribution constant), and K10 (distribution constant). Then, obtained values of V/F, K01, and K10 were applied to predict the 28 days' CT curve by using the same oral first-order one-compartment model, whereby the doses were administered daily for 28 days.

Histopathological Analysis:

Mice were euthanized after four weeks of vehicle or Etn feeding by exposing them to $CO_2$ for 2 min. The organs were immediately collected and formalin fixed. Formalin fixed tissues were then paraffin embedded into 5 μm thick tissue sections that were cut and stained with hematoxylin and eosin and examined with a 10× objective.

Phenotypic Analysis of Immune Cells:

Male BALB/c mice were fed daily with either vehicle or 40 mg/kg Etn for various time periods. Mice were sacrificed after 24, 48 h and 1, 2, 3, 4 weeks and spleens were collected. Total splenocytes were counted after lysis of RBC with RBC lysis buffer. After this, splenocytes where incubated with anti-CD16/CD32 antibody to block Fc receptors and then labeled with anti-CD3-APC, anti-CD4-Alexa488, anti-CD8-Alexa488, anti-DX5-FITC, or anti-CD19-FITC antibodies according to the manufacturer's instructions. Labeled cells were analyzed by flow cytometry using an LSRFortessa Flow cytometer (BD Biosciences, CA). Data from this analysis was analyzed using FlowJo software (TreeStar, OR).

Sample Preparation for 2D-Gel Electrophoresis:

Tumor lysates were prepared from control and Etn-treated tumors and were used for 2D gel electrophoresis after 2D-clean up. For 2D-clean-up, 150 μg of protein was cleaned by a 2D-clean-up kit (GE Healthcare) according to manufacturer's instructions. Protein pellets were finally suspended in 50 μl of S/R buffer (7 M urea, 2 M thiourea, 4% CHAPS).

Sample Labeling and Two-Dimensional Gel Electrophoresis:

25 μg of cleaned control and Etn treated protein samples were labeled with 200 pmol of N-hydroxysuccinimidyl-ester of cyanine dyes Cy3 and Cy5, respectively (GE Healthcare Life Science, Piscataway, N.J.). Samples were quenched with 10 mM lysine and the labeled proteins were mixed. Sample buffer (7 M urea, 4 M thiourea, 4% CHAPS, 2% DTT, 2% IPG buffer, pH 3-10 NL (GE Healthcare Life Science, Piscataway, N.J.)) and Rehydration Solution (7 M urea, 4 M thiourea, 4% CHAPS, 1% DTT, 1% IPG) were added to protein samples to a final volume of 440 μl for each gel. First-dimension IsoElectric Focusing (IEF) was performed using 24 cm IPG strips (pH 3-10, GE Healthcare Life Science, Piscataway, N.J.) in Ettan IPGphor (GE Healthcare Life Science, Piscataway, N.J.). After IEF, the strips were equilibrated by sequential incubation in equilibration buffer (50 mM Tris-HCl (pH 8.8), 6 M urea, 30% glycerol, and 2% SDS) with 1% DTT and equilibration buffer with 4.5% iodoacetamide for 20 min each in dark. After equilibration, the gel strip was placed on top of 10% polyacrylamide and the second-dimension SDS-polyacrylamide gel electrophoresis was conducted in the Ettan DALT II system separation unit (GE Healthcare Life Science, Piscataway, N.J.). After two-dimensional electrophoresis, gel images were acquired on a Typhoon Trio (GE Healthcare) for Cy3 and Cy5 dyes and analyzed using the DeCyder image analysis software (v. 7.0, GE Healthcare Life Science, Piscataway, N.J.). The gels were then stained with Coomassie Brillian Blue (SimplyBlue, Invitrogen, Carlsbad, Calif.) and scanned with a Typhoon Trio scanner to identify proteins spots, which are differentially expressed in control and treated tumors. A list of spots were manually picked from Coomassie stained gels which were more than 1.5 fold increased or decreased and subsequent MS/MS analysis was performed.

Mass Spectrometric Analysis of Proteins:

In-gel digestion of picked gel pieces was performed as described above before mass spectrometric analysis of proteins. RP-HPLC-MS/MS experiments were performed on a LTQ-Orbitrap Elite mass spectrometer (Thermo Fisher) equipped with an EASY-spray source and a nano-LC Ultimate 3000 high-performance liquid chromatography system (Thermo Fisher). EASY-Spray PepMap C18 Columns (50 cm; particle size, 2 μm; pore size, 100 Å; Thermo Fisher) were used for separation. Separation was achieved with a linear gradient from 3% to 40% solvent B for 80 min at a flow rate of 300 nL/min (mobile phase A, 2% ACN, 98% $H_2O$, 0.1% FA; mobile phase B, 80% ACN, 20% $H_2O$, 0.1% FA). The LTQ-Orbitrap Elite mass spectrometer was operated in the data-dependent mode. A full-scan survey MS experiment (m/z range from 375 to 1500; automatic gain control target, 1,000,000 ions; resolution at m/z 200, 60,000; maximum ion accumulation time, 50 ms) was acquired by the Orbitrap mass spectrometer, and the 10 most intense ions were fragmented by HCD in the octopole collision cell. HCD fragment ion spectra were acquired in the Orbitrap analyzer with a resolution of 15,000 at m/z 200 (automatic gain control target, 10,000 ions; maximum ion accumulation time, 200 ms). The MS/MS scan model was set as the centroid. The other conditions used were temperature of 200° C., S-lens rf level of ~60%, ion selection threshold of 50,000 counts for HCD. As a comparison, prior ions were also fragmented by CID and acquired in the ion trap.

Data Filtering and Database Searches:

Raw data was converted to mgf files by Proteome Discoverer 1.3. All of selected spectra were searched with pFind (version 2.1) database searching software. The human proteome sequence database was extracted from Uniprot_swissprot plus Uniprot_TrEMBL (release on April 2012, human, 65,493 entries), concatenated with reversed versions of all sequences. The mass tolerance was set to 20 ppm for the precursor ions and 100 ppm for the fragment ions. A false discovery rate (FIR) of 1% was estimated, respectively, and applied to all data sets at the peptide-spectrum match (PSM) level. The mgf data were compared to the target and decoyed human Uniprot database with static modification of carbamidomethyl (Cys, +57.0214), dynamic modification of oxidation (Met, +15.9949), and acetylation (N-Terminal). The enzyme was set to trypsin, with two missed cleavages allowed. Redundant protein entries were removed by pBuild software to form group entries.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present application as defined by the embodiments described herein.

What is claimed is:
1. A composition consisting of:
monoethanolamine (Etn);
water; and
an acid in an amount effective to achieve a pH value between 2.0-8.0, wherein the composition is formulated in a liquid filled capsule.

2. The composition of claim 1, wherein the composition has a pH value of about 5.

3. The composition of claim 1, wherein the composition has a pH value of between 4.5-5.5.

* * * * *